United States Patent
Darrow et al.

(10) Patent No.: US 6,372,743 B1
(45) Date of Patent: Apr. 16, 2002

(54) CERTAIN ALKYLENE DIAMINE-SUBSTITUTED PYRAZLO (1,5-A)-1,5-PYRIMIDINES AND PYRAZOLO (1,5-A) 1,3,5-TRIAZINES

(75) Inventors: James W. Darrow, Wallingford; Stephane De Lombaert, Madison; Charles Blum, Westbrook; Jennifer Tran, Guilford; Mark Giangiordano, Branford; David Andrew Griffith, Old Saybrook; Philip Albert Carpino, Groton, all of CT (US)

(73) Assignees: Neurogen Corporation, Branford, CT (US); Pfizer Inc., New York, NY (US)

( * ) Notice: Subject to any disclaimer, the term of this patent is extended or adjusted under 35 U.S.C. 154(b) by 0 days.

(21) Appl. No.: 09/676,970

(22) Filed: Sep. 29, 2000

Related U.S. Application Data

(60) Provisional application No. 60/156,869, filed on Sep. 30, 1999.

(51) Int. Cl.[7] ...................... A61K 31/53; A61K 31/505; C07D 251/00; C07D 251/18; C07D 487/00
(52) U.S. Cl. ................ 514/246; 514/245; 514/258; 544/194; 544/197; 544/198; 544/204; 544/206; 544/209; 544/211; 544/212; 544/263; 544/281
(58) Field of Search .............................. 514/245, 246, 514/258; 544/194, 197, 198, 204, 206, 209, 211, 212, 263, 281

(56) References Cited

U.S. PATENT DOCUMENTS 6,060,478 A * 5/2000 Gilligan et al. .............. 514/258

FOREIGN PATENT DOCUMENTS

| WO | 9729109 | 8/1997 |
| WO | 9803510 | 1/1998 |
| WO | 9808847 | 3/1998 |
| WO | 9938868 | 8/1999 |
| WO | 9940091 | 8/1999 |
| WO | 0123388 | 4/2001 |

OTHER PUBLICATIONS

Britton, T.C., et al. "Structure–Activity Relationships of a Series of Benzothiophene–Derived NPY Y1 Antagonists: ... Chain"*Bioorganic & Medicinal Chemistry Letters*, vol. 9, pp. 475–480, (1999).
Hipskind, P.A., et al. "Potent and Selective 1,2,3–Trisubstituted Indole NYP Y–1 Antagonists"*J. Med. Chem.*, vol. 40, pp. 3712–3714, (1997).
Murakami, Y., et al. "1,2–Disubstituted Benzazepines as Novel, Potent, Selective Neuropeptide Y Y1 Receptor Antagonists"*J. Med. Chem.*, vol. 42, pp. 2621–2632, (1999).
Tatemoto, K., et al. "Neuropeptide Y–a novel brain peptide with structural similarities to peptide YY and pancreatic polypeptide"*Nature*, vol. 296, pp. 659–660, (1982).
Wustrow, D.J., et al. "Pyrazolo [1, 5–a]pyrimidine CRF–1 Receptor Antagonists"*Bioorganic & Medicinal Chemistry Letters*, vol. 8, pp. 2067–2070, (1998).
Zarrinmayeh, H., et al. "Synthesis and Evaluation of a Series of Novel 2–[(4–Chlorophenoxy)methyl]–benzimidazoles ... Antagonists", J. Med. Chem, vol. 41, pp. 2709–2719, (1998).
Zarrinmayeh, H., et al. "Structure–activity Relationship of a Series of Diaminoalkyl Substituted Benzimidazole ... Antagonist"*Bioorganic & Medicinal Chemistry Letters*, vol. 9, pp. 647–652, (1992).
Zimmerman, D. M., et al. "Structure–activity Relationships of a Series of 1–Substituted–4–...Antagonists"*Bioorganic & Medicinal Chemistry Letters*vol. 8, pp. 473–476, (1998).

* cited by examiner

Primary Examiner—Richard L. Raymond
Assistant Examiner—Tamthom N. Truong
(74) Attorney, Agent, or Firm—Ladas & Parry

(57) ABSTRACT

Disclosed are compounds of the formula:

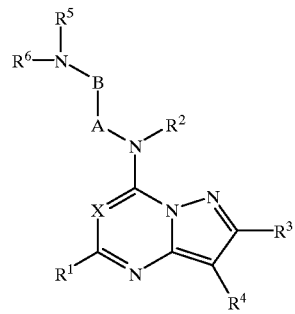

where $R^1$, $R^2$, $R^3$, $R^4$, $R^5$, $R^6$, and X are defined herein. These compounds are selective modulators of NPY1 receptors. These compounds are useful in the treatment of a number of CNS disorders, metabolic disorders, and peripheral disorders, particularly eating disorders and hypertension. Methods of treatment of such disorders and well as packaged pharmaceutical compositions are also provided.

Compounds of the invention are also useful as probes for the localization of NPY1 receptors and as standards in assays for NPY1 receptor binding. Methods of using the compounds in receptor localization studies are given.

50 Claims, No Drawings

CERTAIN ALKYLENE DIAMINE-SUBSTITUTED PYRAZLO (1,5-A)-1,5-PYRIMIDINES AND PYRAZOLO (1,5-A) 1,3,5-TRIAZINES

CROSS REFERENCE TO RELATED APPLICATION

This application claims priority from Provisional Application 60/156,869, filed on Sep. 30, 1999, which is incorporated herein by reference.

FIELD OF THE INVENTION

This invention relates to certain alkylene diamine-substituted pyrazolo[1,5,-a]-1,5-pyrimidines and pyrazolo [1,5-a]-1,3,5-triazines which selectively and potently bind mammalian neuropeptide Y (NPY) receptors. This invention also relates to pharmaceutical compositions comprising such compounds. It further relates to the use of such compounds in treating physiological disorders associated with an excess of neuropeptide Y, especially feeding disorders, some psychiatric disorders, and certain cardiovascular diseases.

BACKGROUND OF THE INVENTION

Neuropeptide Y (NPY) is a 36 amino acid peptide first isolated in 1982 [K. Tatemoto, M. Carlquist, V. Mutt, *Nature*, 296, 659, (1982)] and subsequently found to be largely conserved across species. It belongs to a large family of peptides which includes, among others, peptide YY (PYY) and pancreatic peptide (PP). NPY is the most abundant peptide in the mammalian brain, but is also localized in sympathetic neurons and NPY-containing fibers have been found in peripheral tissues, such as around the arteries in the heart, the respiratory tract, the gastrointestinal tract, and the genitourinary tract. Central injection of NPY elicits a multitude of physiological responses, such as stimulation of feeding, increase in fat storage, elevation of blood sugar and insulin, anxiolytic behaviors, reduction in locomotor activity, hormone release, increase in blood pressure, reduction in body temperature, and catalepsy. In the cardiovascular system, NPY is believed to be involved in the regulation of coronary tone, while in the gastrointestinal tract, PYY is reported to cause inhibition of gastric acid secretion, pancreatic exocrine secretion, and gastroinestinal motility. These effects are selectively mediated by various NPY receptors which currently include the $Y_1$, $Y_2$, $Y_3$, $Y_4$, and $Y_6$ subtypes, in addition to the hypothetical $Y_{1\text{-like}}$ subtype [C. Wahlestedt, D. Reis, *Ann. Rev. Pharmacol. Toxicol.*, 33, 309 (1993); D. Gehlert, P. Hipskind, *Curr. Pharm. Design*, 1, 295 (1995); M. C. Michel et al., *Pharmacol. Rev.*, 50, 143 (1998)]. Selective peptidic agonists and antagonists have been identified for most of the subtypes, but few selective non-peptidic antagonists have been reported [B. A. Zimanyi, Z. Fathi, G. S. Pointdexter, *Curr. Pharm. Design*, 4, 349 (1998)]. The $Y_1$ and $Y_5$ receptor subtypes appear to be involved in appetite regulation, but their relative contribution to the modulation of food intake and energy expenditure remains unclear [D. R. Gehlert, P. A. Hipskind, *Exp. Opin. Invest. Drugs*, 6, 1827, (1997)]. The discovery of non-peptidic antagonists of the $Y_1$ and/or $Y_5$ receptor, would provide novel therapeutic agents, devoid of the shortcomings of the peptide antagonists, namely, for example, poor metabolic stability, low oral bioavailability, poor brain permeability, for the treatment of obesity and cardiovascular diseases. Recently, a few of those agents have been reported [D. R. Gehlert, P. A. Hipskind, *Exp. Opin. Invest. Drugs*, 6, 1827, (1997); P. Hipskind et al., *J Med. Chem.*, 40, 3712 (1997); M. Müller et al., *Arch. Pharm. Pharm. Med. Chem.*, 330, 333 (1997); H. Zarrinmayeh, et al., *J Med. Chem.*, 41 2709 (1998); H. A. Wieland et al., Br. *J. Pharmacol.*, 125, 549 (1998); Y. Shigeri et al., *Pharmacol. Letters*, 63, PL 151 (1998); D. M Zimmerman et al., *Bioorg. Med. Chem. Letters*, 8, 473, (1998); L. Criscione, *J Clin. Invest.*, 102 12, 2136 (1998); Y. Murakami, et al., *J. Med. Chem.*, 42, 2621 (1999); T. C. Britton et al., *Bioorg. Med. Chem. Letters*, 9, 475, (1999); H. Zarrinmayeh, et al., *Bioorg. Med. Chem. Letters*, 9, 647, (1999)], some of which having demonstrated pharmacological efficacy in pre-clinical animal models. The present invention provides a novel class of potent non-peptidic antagonists of the NPY receptors, in particular, the Y1 receptor.

Insofar as is known, aminoalkyl substituted pyrazolo[1, 5,-a]-1,5-pyrimidines and pyrazolo[1,5-a]-1,3,5-triazines have not been previously reported as NPY receptor(s) antagonists useful in the treatment of feeding and cardiovascular disorders. However, this general class of compounds has been described for other uses by virtue of different mechanisms of action. For instance, WO 98/03510 and WO 99/38868 (Du Pont Pharmaceuticals) discloses pyrazolo[1,5,-a]-1,5-pyrimidines and pyrazol[1,5-a]-1,3,5-triazines as antagonists of the corticotropin releasing factor (CRF). Therein, other prior art relative to pyrazolo[1,5,-a]-1,5-pyrimidines and pyrazolo[1,5-a]-1,3,5-triazines is also described. Similar compounds have also been described in WO 97/29109, 98/08847, and D. J. Wustrow et al., *Bioorg. Med. Chem. Lett.* 8, 2067 (1998).

SUMMARY OF THE INVENTION

Compounds that interact with the $Y_1$ receptor and inhibit the activity of neuropeptide Y at those receptors are useful in treating physiological disorders associated with an excess of neuropeptide Y, including eating disorders, such as, for example, obesity and bulimia, and certain cardiovascular diseases, for example, hypertension.

This invention relates to novel compounds, compositions, and methods for the treatment of physiological disorders associated with an excess of neuropeptide Y. The novel compounds encompassed by the present invention are those of formula I

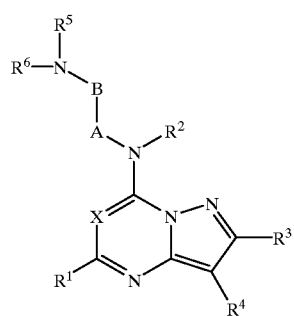

I wherein:
  X is N or $CR^{14}$;
  $R^1$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, $C_1$–$C_6$ alkyl-$NR^8R^9$;
  $R^2$ is H, $C_1$–$C_6$ alkyl which optionally forms a $C_3$–$C_6$ aminocarbocycle or a $C_2$–$C_5$ aminoheterocycle with A or B, each optionally substituted at each occurrence with $R^7$, $C_3$–$C_{10}$ cycloalkyl, or ($C_3$–$C_{10}$ cycloalkyl) $C_1$–$C_6$ alkyl; or $R^2$ and $R^6$ jointly form with the 2 nitrogen atoms to which they are bound a $C_2$–$C_5$ aminoheterocycle optionally substituted at each occurrence with $R^7$;

A is $(CH_2)_m$ where m is 1,2 or 3 and is optionally mono- or di-substituted on each occurrence with $C_1$–$C_6$ alkyl, $C_3$–$C_{10}$ cycloalkyl, ($C_3$–$C_{10}$ cycloalkyl) $C_1$–$C_6$ alkyl, $C_1$–$C_6$ alkenyl, $C_1$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, $C_1$–$C_6$ alkyl-$NR^8R^9$, or A and B jointly form a $C_3$–$C_6$ carbocycle, optionally substituted at each occurrence with $R^7$, or, as mentioned above, A and $R^2$ jointly form a $C_3$–$C_6$ aminocarbocycle or a $C_2$–$C_5$ aminoheterocycle optionally substituted at each occurrence with $R^7$;

B is $(CH_2)_n$ where n is 1,2 or 3 and is optionally mono- or di-substituted on each occurrence with $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, $C_1$–$C_6$ alkyl-$NR^8R^9$, or, as mentioned above, B and A jointly form a $C_3$–$C_6$ carbocycle, optionally substituted at each occurrence with $R^7$ or, as mentioned above, B and $R^2$ jointly form a $C_3$–$C_6$ aminocarbocycle or a $C_2$–$C_5$ aminoheterocycle optionally substituted at each occurrence with $R^7$;

$R^3$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$, $C_1$–$C_6$ cyanoalkyl, $NR^8R^9$, $C_1$–$C_6$ alkyl-$NR^8R^9$;

$R^4$ is selected from aryl or heteroaryl, each optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, $C_1$–$C_6$ alkynyl, halogen, $C_1$–$C_6$ haloalkyl, trifluromethylsulfonyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$ alkyl-$CONR^8R^9$, $COOR^7$, $C_1$–$C_6$ alkyl-$COOR^7$, CN, $C_1$–$C_6$ alkyl-CN, $SO_2NR^8R^9$, $SO_2R^7$, aryl, heteroaryl, heterocycloalkyl, 3-, 4-, or 5-(2-oxo-1,3-oxazolidinyl), with the proviso that at least one of the positions ortho or para to the point of attachment of the aryl or heteroaryl ring to the pyrazole is substituted;

$R^5$ is selected from:

$C_1$–$C_6$ alkyl, ($C_3$–$C_{10}$ cycloalkyl) $C_1$–$C_6$ alkyl, $C_2$–$C_6$ alkenyl, $C_2$–$C_6$ alkynyl, each of which is substituted with 1 to 5 groups independently selected at each occurrence from halo, $C_1$–$C_2$ haloalkyl, $OR^7$, cyano, $NR^8R^9$, $CONR^8R^9$, $COOR^7$, $SO_2NR^8R^9$, $SO_2R^7$, $NR^{11}COR^{12}$, $NR^{11}SO_2R^7$;

$C_1$–$C_6$ arylalkyl, $C_1$–$C_6$ heteroarylalkyl, $C_5$–$C_8$ arylcycloalkyl, or $C_5$–$C_8$ heteroarylcycloalkyl, where aryl is phenyl or naphthyl, and heteroaryl is 2-,3-, or 4-pyridyl, 2-, 4- or 5-pyrimidinyl, triazinyl, 1-, 2- or 4-imidazolyl, 2-, 4-, or 5-oxazolyl, isoxazolyl, indolyl, pyrazolyl, quinolyl, isoquinolyl, 2-, 4-, or 5-thiazolyl, benzothiadiazolyl, 1-, 3- or 4-pyrazolyl, 1-, 3- or 4-triazolyl, 2-triazinyl, 2-pyrazinyl, 2-, or 3-furanyl, 2-, or 3-thienyl, 2-, or 3-benzothienyl, or 1-, 2- or 5-tetrazolyl, each of which is optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, trifluromethylsulfonyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), with the proviso that 2 adjacent substituents can optionally form together a $C_3$–$C_{10}$ cycloalkyl ring, a $C_3$–$C_{10}$ cycloalkenyl ring or a heterocycloalkyl ring;

$C_3$–$C_{10}$ cycloalkyl substituted with 1 to 6 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, $OR^7$, $NR^8R^9$, with the proviso that when two $OR^7$ or $NR^8R^9$ substituents are geminally located on the same carbon $R^7$ is not H and they can form together a $C_2$–$C_4$ ketal, oxazoline, oxazolidine, imidazoline, or imidazolidine heterocycle, $C_1$–$C_6$ alkyl-$OR^7$, $C_1$–$C_6$ alkyl-$NR^8R^9$, $CONR^8R^9$, $COOR^7$, CN, oxo, hydroximino, $C_1$–$C_6$ alkoximino, $SO_2NR^8R^9$, $SO_2R^7$, heterocycloalkyl, aryl, heteroaryl, where aryl or heteroaryl is optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, tkifluromethylsulfonyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), with the proviso that 2 adjacent substituents can optionally form together a $C_3$–$C_{10}$ cycloalkyl ring, a $C_3$–$C_{10}$ cycloalkenyl ring or a heterocycloalkyl ring;

aryl or heteroaryl, optionally substituted with 1 to 5 substituents independently selected at each occurrence from halogen, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, trifluromethylsulfonyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), with the proviso that 2 adjacent substituents can optionally form together a $C_3$–$C_{10}$ cycloalkyl ring, a $C_3$–$C_{10}$ cycloalkenyl ring or a heterocycloalkyl ring; or 3- or 4-piperidinyl, 3-pyrrolidinyl, 3- or 4-tetrahydropyranyl, 3-tetrahydrofuranyl, 3- or 4-tetrahydropyranyl, 3-tetrahydrofuranyl, 3- or 4-tetrahydrothiopyranyl, 3- or 4-(1,1-dioxo) tetrahydrothiopyranyl, 1-azabicyclo[4.4.0]decyl, 8-azabicyclo[3.2.1]octanyl, norbomyl, quinuclidinyl, indolin-2-one-3-yl, 2-(methoximino)- perhydroazepin-6-yl, each optionally substituted with 1 to 5 substituents independently selected at each occurrence from $R^7$, $C_1$–$C_6$ alkyl-$OR^7$, $C_1$–$C_6$ alkyl-$NR^8R^9$, $CONR^8R^9$, CN, $COOR^7$ $SO_2NR^8R^9$, $SO_2R^7$;

$R^6$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, $C_1$–$C_6$ arylalkyl, $C_1$–$C_6$ heteroarylalkyl where aryl or heteroaryl are optionally substituted with 1 to 5 substituents independently selected at each occurrence from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^7$, CN, $SO_2NR^8R^9$, $SO_2R^7$, or $R^6$ and $R^2$, as mentioned above, jointly form, with the 2 nitrogen atoms to which they are bound, a $C_2$–$C_5$ aminoheterocycle optionally substituted at each occurrence with $R^7$;

$R^7$ is H, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl each optionally substituted with 1 to 5 substituents independently selected at each occurrence from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^{13}$, CN, $SO_2NR^8R^9$, $SO_2R^{13}$, with the proviso that for $SO_2R^{13}$, $R^{13}$ cannot be H;

$R^8$ and $R^9$ are independently selected at each occurrence from H, $C_1$–$C_6$ alkyl, $C_3$–$C_{10}$ cycloalkyl, $C_2$–$C_6$ alkenyl, $C_3$–$C_{10}$ cycloalkenyl, $C_2$–$C_6$ alkynyl, heterocycloalkyl, $C_1$–$C_8$ alkanoyl, aroyl, heteroaroyl, aryl, heteroaryl, $C_1$–$C_6$ arylalkyl or $C_1$–$C_6$ heteroarylalkyl, or $R^8$ and $R^9$, taken together, can form a $C_3$–$C_6$ aminocarbocycle or a $C_2$–$C_5$ aminoheterocycle each optionally substituted at each occurrence with $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl;

$R^{11}$ is selected from H, $C_1$–$C_6$ alkyl, $C_3$–$C_{10}$ cycloalkyl, ($C_3$–$C_{10}$ cycloalkyl) $C_1$–$C_6$ alkyl;

$R^{12}$ is selected from H, aryl, heteroaryl, $C_1$–$C_6$ alkyl, $C_3$–$C_{10}$ cycloalkyl, ($C_3$–$C_{10}$ cycloalkyl) $C_1$–$C_6$ alkyl, optionally substituted with $OR^7$, $NR^8R^9$, $C_3$–$C_6$ aminocarbocycle, or $C_2$–$C_5$ aminoheterocycle;

$R^{13}$ is independently selected at each occurrence from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, $C_1$–$C_6$ haloalkyl, with the proviso that when $R^7$ is $SO_2R^{13}$, $R^{13}$ cannot be H;

$R^{14}$ is H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, $C_2$–$C_4$ alkynyl, halo, or CN;

or a pharmaceutically acceptable salt, hydrate, or prodrug thereof.

One embodiment encompassed by the present invention is a compound in accordance with formula 1

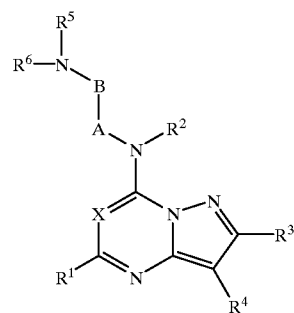

wherein:

X is N or $CR^{14}$;

$R^1$ is selected from H, $C_1$–$C_6$ alkyl, $C_3$–$C_6$ cycloalkyl, ($C_3$–$C_{10}$cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$alkyl-$OR^7$; $C_1$–$C_6$ cyanoalkyl, $NR^8R^9$, $C_1$–$C_6$ alkyl-$NR^8R^9$;

$R^2$ is H, $C_1$–$C_6$ alkyl which optionally forms a $C_3$–$C_6$ aminocarbocycle or a $C_2$–C5 aminoheterocycle with A or B, each of which is optionally substituted at each occurrence with $R^7$, $C_3$–$C_{10}$ cycloalkyl, or ($C_3$–$C_{10}$ cycloalkyl) $C_1$–$C_6$ alkyl; or $R^2$ and $R^6$ jointly form with the 2 nitrogen atoms to which they are bound, to form a $C_2$–$C_5$ aminoheterocycle optionally substituted at each occurance with $R^7$;

A is $(CH_2)_m$, where m is 1, 2 or 3 and is optionally mono- or di-substituted on each occurrence with $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, $C_1$–$C_6$ alkyl-$NR^8R^9$, or A and B jointly form a $C_3$–$C_6$ carbocycle, optionally substituted at each occurrence with $R^7$; or A and $R^2$ jointly form a $C_3$–$C_6$ aminocarbocycle or a $C_2$–$C_5$ aminoheterocycle optionally substituted at each occurrence with $R^7$;

B is $(CH_2)_n$, where n is 1, 2 or 3 and is optionally mono- or di-substituted on each occurrence with $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl $C_2$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, and $C_1$–$C_6$ alkyl-$NR^8R^9$; or as mentioned above, B and A jointly form a $C_3$–$C_6$ carbocycle, optionally substituted at each occurrence with $R^7$; or, as mentioned above, B and $R^2$ jointly form a $C_3$–$C_6$ aminocarbocycle or a $C_2$–$C_5$ aminoheterocycle optionally substituted at each occurrence with $R^7$;

$R^3$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ cyanoalkyl, $NR^8R^9$, $C_1$–$C_6$ alkyl-$NR^8R^9$;

$R^4$ is selected from aryl or heteroaryl, each of which is substituted with 1 to 5 substituents independently selected from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, $C_1$–$C_6$ alkynyl, halogen, $C_1$–$C_6$ haloalkyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$ alkyl-$CONR^8R^9$, $COOR^7$, $C_1$–$C_6$ alkyl-$COOR^7$, CN, $C_1$–$C_6$ alkyl-CN, $SO_2NR^8R^9$, $SO_2R^7$, aryl, heteroaryl, heterocycle 3-, 4-, or 5-(2-oxo-1,3-oxazolidinyl), wherein at least one of the positions ortho or para to the point of attachment of the aryl or heteroaryl ring to the pyrazole is substituted;

$R^5$ is selected from:

$C_1$–$C_6$ alkyl, ($C_3$–$C_{10}$ cycloalkyl) $C_1$–$C_6$ alkyl, $C_2$–$C_6$ alkenyl, $C_2$–$C_6$ alkynyl, each of which is substituted with 1 to 5 groups independently selected at each occurrence from halo, $C_1$–$C_2$ haloalkyl, oxo, $OR^7$, cyano, $NR^8R^9$, $CONR^8R^9$, $COOR^7$, $SO_2NR^8R^9$, $SO_2R^7$, $NR^{11}CORR^{12}$, $NR^{11}SO_2R^7$; or Aryl($C_1$–$C_6$)alkyl, heteroaryl($C_1$–$C_6$)alkyl, aryl($C_5$–$C_8$)cycloalkyl, or heteroaryl($C_5$–$C_8$)cycloalkyl, where aryl is phenyl or naphthyl, and heteroaryl is 2-, 3- or 4-pyridyl, 2-, 4-, 5-pyrimidinyl, triazinyl, 1-, 2-, or 4-imidazolyl 2-, 4-, or 5-oxazolyl, isoxazol-indolyl, pyrazolyl, quinolyl, isoquinolyl, 2-, 4-, or 5-thiazolyl, benzothiadiazolyl, 1-, 3- or 4-pyrazolyl, 1-, 3- or 4-triazolyl, 2-triazinyl, 2-pyrazinyl, 2-, or 3-furanyl, 2-, or 3-thienyl, 2-, or 3-benzothienyl, or 1-, 2- or 5 tetrazolyl, each of which is optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), wherein any 2 adjacent substituents may be take together to form a $C_3$–$C_{10}$ cycloalkyl ring, a $C_3$–$C_{10}$ cycloalkenyl ring or a heterocycloalkyl ring; or $C_3$–$C_{10}$ cycloalkyl optionally substituted with 1 to 6 substituents independently selected from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, oxo, halogen, $C_1$–$C_6$ haloalkyl, $OR^7$, $NR^8R^9$, (with the proviso that when two $OR^7$ or $NR^8R^9$ substituents are geminally located on the same carbon $R^7$ is not H and the geminally located $OR^7$ or $NR^8R^9$ substituents can be taken together to form a $C_2$–$C_4$ ketal, oxazoline, oxazolidine, imidazoline, or imidazolidine heterocycle), $C_1$–$C_6$ alkyl-$OR^7$, $C_1$–$C_6$ alkyl-$NR^8R^9$, $CONR^8R^9$, $COOR^7$, CN, oxo, hydroximino, $C_1$–$C_6$ alkoximino, $SO_2NR^8R^9$, $SO_2R^7$, heterocycloalkyl, aryl, heteroaryl, where aryl or heteroaryl is optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN,$SO_2NR^8R^9$, $SO_2R^7$, aryl, heteroaryl, heterocycloalkyl, 3-, 4-, or 5-(2-oxo-1,3-oxazolidinyl), with the proviso that 2 adjacent substituents can optionally form together a $C_3$–$C_{10}$ cycloalkyl ring, a $C_3$–$C_{10}$ cycloalkenyl ring or a heterocycloalkyl ring; or aryl or heteroaryl, optionally substituted with 1 to 5 substituents independently selected at each occurrence from halogen, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), wherein any 2 adjacent substituents may be taken together to form a $C_3$–$C_{10}$ cycloalkyl ring, a $C_3$–$C_{10}$ cycloalkenyl ring or a heterocycloalkyl ring; or 3- or 4-piperidinyl, 3-pyrrolidinyl, 3- or 4-tetrahydropyranyl, 3-tetrahydrofuranyl, 3- or 4-tetrahydropyranyl, 3-tetrahydrofuranyl, 3- or 4-tetrahydrothiopyranyl, 3- or 4-(1,1-dioxo)tetrahydrothiopyranyl, 1-azabicyclo[4.4.0]decyl, 8-azabicyclo[3.2.1]octanyl, norbornyl, quinuclidinyl, indolin-2-one-3-yl, 2-(methoximino)-perhydroazepin-6-yl, each optionally substituted with 1 to 5 substituents independently selected at each occurrence from $R^7$, $C_1$–$C_6$ alkyl-$OR^7$, $C_1$–$C_6$ alkyl-$NR^8R^9$, $CONR^8R^9$, CN, $COOR^7$ $SO_2NR^8R^9$, and $SO_2R^7$;

$R^6$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, aryl($C_1$–$C_6$)alkyl, heteroaryl($C_1$–$C_6$)alkyl each of which is optionally substituted with 1 to 5 substituents independently from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^7$, CN, $SO_2NR^8R^9$, and $SO_2R^7$; or $R^6$ and $R^2$ jointly form with the two nitrogens to which they are bound a $C_2$–$C_5$ aminoheterocycle optionally substituted at each occurrence by $R^7$;

$R^7$ is independently selected at each occurrence from H, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl each optionally substituted with 1 to 5 substituents independently selected from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^{13}$, CN, $SO_2NR^8R^9$, and $SO_2R^{13}$, with the proviso that when $R^7$ is $SO_2R^{13}$, $R^{13}$ cannot be H;

$R^8$ and $R^9$ are independently selected at each occurrence from H, $C_1$–$C_6$ alkyl, $C_3$–$C_{10}$ cycloalkyl, $C_2$–$C_6$ alkenyl, $C_3$–$C_{10}$ cycloalkenyl, $C_2$–$C_6$ alkynyl, heterocycloalkyl, $C_1$–$C_8$ alkanoyl, aroyl, heteroaroyl, aryl, heteroaryl, $C_1$–$C_6$ arylalkyl or $C_1$–$C_6$ heteroarylalkyl, or $R^8$ and $R^9$, taken together, can form a $C_3$–$C_6$ aminocarbocycle or a $C_2$–$C_5$ aminoheterocycle each of which is optionally substituted with $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl;

$R^{11}$ is selected from H, $C_1$–$C_6$ alkyl, $C_3$–$C_{10}$ cycloalkyl, ($C_3$–$C_{10}$ cycloalkyl) $C_1$–$C_6$ alkyl;

$R^{12}$ is selected from H, aryl, heteroaryl, $C_1$–$C_6$ alkyl, $C_3$–$C_{10}$ cycloalkyl, ($C_3$–$C_{10}$ cycloalkyl) $C_1$–$C_6$ alkyl, optionally substituted with $OR^7$, $NR^8R^9$, $C_3$–$C_6$ aminocarbocycle, or $C2$–$C_5$ aminoheterocycle;

$R^{13}$ is independently selected at each occurrence from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, $C_1$–$C_6$ haloalkyl, with the proviso that when $R^7$ is $SO_2R^{13}$, $R^{13}$ cannot be H; and $R^{14}$ is H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, $C_2$–$C_4$ alkynyl, halo, or CN or a pharmaceutically acceptable salt, hydrate or prodrug thereof.

Another embodiment encompassed by the present invention is a compound in accordance with formula 1

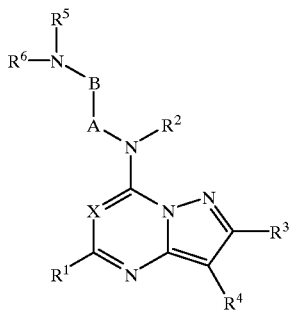

or a pharmaceutically acceptable salt, hydrate or prodrug thereof wherein:

X is N or $CR^{14}$;

$R^1$ is selected from H, $C_1$–$C_6$ alkyl, $C_3$–$C_6$ cycloalkyl, ($C_3$–$C_{10}$cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$; $C_1$–$C_6$ alkyl-$OR^7$;$C_1$–$C_6$ cyanoalkyl, $NR^8R^9$, $C_1$–$C_6$ alkyl-$NR^8R^9$;

$R^2$ is H, $C_1$–$C_6$ alkyl, $C_3$–$C_{10}$ cycloalkyl, or ($C_3$–$C_{10}$ cycloalkyl) $C_1$–$C_6$ alkyl, wherein each alkyl or cycloalkyl group may be optionally substituted with 1 to 3 $R^{7a}$ groups;

$R^2$ may optionally join with $R^5$ and the two and the 2 nitrogen atoms to which they are bound to form a 6 to 10 membered heterocyclic ring optionally substituted at each carbon with $R^{7a}$; or $R^2$ and A may optionally join to form a 3 to 8 membered heterocyclic ring optionally substituted at each carbon with $R^{7a}$; or $R^2$ and B optionally join to form a 4 to 10 membered heterocyclic ring optionally substituted at each carbon with $R^{7a}$;

A represents an alkyl chain of 1, 2 or 3 carbon atoms which is optionally mono- or di-substituted at each carbon with substituents independently selected from $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, $C_1$–$C_6$ alkyl-$NR^8R^9$, or A and B jointly form a $C_3$–$C_6$ carbocycle, optionally substituted at each occurrence with $R^{7a}$;

B represents an alkyl chain of 1, 2 or 3 carbon atoms, which is optionally mono- or di-substituted at each carbon with substituents independently selected from $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, and $C_1$–$C_6$ alkyl-$NR^8R^9$, or B and $R^5$ may jointly form a 4 to 7 membered heterocyclic ring, which is optionally substituted at each atom with $R^{7a}$;

$R^3$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$, $C_1$–$C_6$ cyanoalkyl, $NR^8R^9$, $C_1$–$C_6$ alkyl-$NR^8R^9$;

$R^4$ is selected from aryl or heteroaryl, each of which is substituted with 1 to 5 substituents independently selected from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, $C_1$–$C_6$ alkynyl, halogen, $C_1$–$C_6$ haloalkyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$ alkyl-$CONR^8R^9$, $COOR^7$, $C_1$–$C_6$ alkyl-$COOR^7$, CN, $C_1$–$C_6$ alkyl-CN, $SO_2NR^8R^9$, $SO_2R^7$, aryl, heteroaryl, heterocycloalkyl, 3-, 4-, or 5-(2-oxo-1,3-oxazolidinyl), $C_2$–$C_4$ alkynyl wherein at least one of the positions ortho or para to the point of attachment of the aryl or heteroaryl ring to the pyrazole is substituted;

$R^5$ is selected from:

$C_1$–$C_6$ alkyl, ($C_3$–$C_{10}$ cycloalkyl) $C_1$–$C_6$ alkyl, each of which is substituted with 1 to 5 groups independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_2$–$C_6$, alkenyl, halogen, $C_1$–$C_6$ haloalkyl, $OR^7$, $NR^8R^9$, (with the proviso that when two $OR^7$ or $NR^8R^9$ substituents are geminally located on the same carbon $R^7$ is not H and the geminally located $OR^7$ or $NW^8R^9$ substituents can be taken together to form a $C_2$–$C_4$ ketal, oxazoline, oxazolidine, imidazoline, or imidazolidine heterocycle), $C_1$–$C_6$ alkyl-$OR^7$, $C_1$–$C_6$ alkyl-$NR^8R^9$, $CONR^8R^9$, $COOR^7$, CN, oxo, hydroximino, $C_1$–$C_6$ alkoximino, $SO_2NR^8R^9$, $SO_2R^7$, heterocycloalkyl, aryl, heteroaryl, where aryl or heteroaryl is optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl), $C_1$–$C_6$ alkyl, $C_2$–$C_6$ alkenyl, halogen, $C_1$–$C_6$ haloalkyl, $OR^7$, $NR^8R^9$, $C_1$–$C_6$ alkyl-$OR^7$, $C_1$–$C_6$ alkyl $NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), with the proviso that 2 adjacent substituents can optionally form together a $C_3$–$C_{10}$, cycloalkyl ring, a $C_3$–$C_{10}$ cycloalkenyl ring or a heterocycloalkyl ring; with the proviso that $C_1$–$C_6$ alkyl group is substituted with a $C_1$–$C_6$ alkyl group to give a $C_7$–$C_{10}$ alkyl group; or Aryl($C_1$–$C_6$)alkyl, heteroaryl($C_1$–$C_6$)alkyl, aryl ($C_5$–$C_8$)cycloalkyl, or heteroaryl($C_5$–$C_8$) cycloalkyl, each of which is optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), wherein any 2 adjacent substituents may be take together to form a $C_3$–$C_{10}$ cycloalkyl ring, a $C_3$–$C_{10}$ cycloalkenyl ring or a heterocycloalkyl ring; or $C_2$–$C_6$ alkenyl, $C_2$–$C_6$ alkynyl, $C_3$–$C_{10}$ cycloalkenyl, or a 3 to 10 membered mono- or bicyclic heterocycle containing 1-3 O, S or N atoms, each of which is optionally substituted with 1 to 6 substituents independently selected from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_2$–$C_6$ alkenyl, halogen, $C_1$–$C_6$ haloalkyl, $OR^7$, $NR^8R^9$, (with the proviso that when two $OR^7$ or $NR^8R^9$ substituents are geminally located on the same carbon $R^7$ is not H and the geminally located $OR^7$ or $NR^8R^9$ substituents can be taken together to form a $C_2$–$C_4$ ketal, oxazoline, oxazolidine, imidazoline, or imidazolidine heterocycle), $C_1$–$C_6$ alkyl-$OR^7$, $C_1$–$C_6$ alkyl-$NR^8R^9$, $CONR^8R^9$, $COOR^7$, CN, oxo, hydroximino, $C_1$–$C_6$ alkoximino, $SO_2NR^8R^9$, $SO_2R^7$, $COR^7$, heterocycloalkyl, aryl, $C_1$–$C_6$ alkylaryl, heteroaryl, $C_1$–$C_6$ alkylheteroaryl where aryl or heteroaryl is optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_1$-cycloalkyl) $C_1$–$C_6$ alkyl, $C_2$–$C_6$ alkenyl, halogen, $C_1$–$C_6$ haloalkyl, $OR^7$, $NR^8R^9$, $C_1$–$C_6$ alkyl-$OR^7$, $C_1$–$C_6$ alkyl-$NR^8R^9$, $CONR^8R^9$, $COOR^7CN$, $SO_2NR^8R^9$, $SO_2R^7$, aryl, heteroaryl, heterocycloalkyl, 3-, 4-, or 5-(2-oxo-1,3-oxazolidinyl), with the proviso that 2 adjacent substituents can optionally form together a $C_3$–$C_{10}$ cycloalkyl ring, a $C_3$–$C_{10}$ cycloalkenyl ring or a heterocycloalkyl ring; or aryl or heteroaryl, optionally substituted with 1 to 5 substituents independently selected at each occurrence from halogen, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_2$–$C_6$ alkenyl, halogen, $C_1$–$C_6$ haloalkyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), wherein any 2 adjacent substituents may be taken together to form a $C_3$–$C_{10}$ cycloalkyl ring, a $C_3$–$C_{10}$ cycloalkenyl ring or a heterocycloalkyl ring;

$R^6$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, aryl ($C_1$–$C_6$)alkyl, heteroaryl($C_1$–$C_6$)alkyl each of which is optionally substituted with 1 to 5 substituents independently from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^7$, CN, $SO_2NR^8R^9$, and $SO_2R^7$;

$R^7$ is independently selected at each occurrence from H, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, aryl, heteroaryl, $C_1$–$C_6$ arylalkyl or $C_{1-6}$ heteroarylalkyl each optionally substituted with 1 to 5 substituents independently selected from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^{13}$, CN, $SO_2NR^8R^9$, and $SO_2R^{13}$;

$R^{7a}$ is independently selected at each occurrence from H, $C_1$–$C_6$ alkyl, $C_3$–$C_{10}$ cycloalkyl, $C_3$–$C_{10}$, cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl each optionally substituted with 1 to 5 substituents independently selected from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^{13}$, CN, $SO_2NR^8R^9$, and $SO_2R^{13}$, with the proviso that when $R^{7a}$ is $SO_2R^{13}$, $R^{13}$ cannot be H;

$R^8$ and $R^9$ are independently selected at each occurrence from H, $C_1$–$C_6$ alkyl, $C_3$–$C_{10}$ cycloalkyl, $C_2$–$C_6$ alkenyl, $C_3$–$C_{10}$ cycloalkenyl, $C_2$–$C_6$ alkynyl, heterocycloalkyl, $C_1$–$C_8$ alkanoyl, aroyl, heteroaroyl, aryl, heteroaryl, $C_1$–$C_6$ arylalkyl or $C_1$–$C_6$ heteroarylalkyl, or $R^8$ and $R^9$ taken together can form a $C_3$–$C_6$ aminocarbocycle or a $C_2$–$C_5$ aminoheterocycle each of which is optionally substituted with $C_1$–$C_6$ alkyl, $C_3$–$C_{10}$ cycloalkyl, $C_3$–$C_{10}$, cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl;

$R^{11}$ is selected from H, $C_1$–$C_6$ alkyl, $C_3$–$C_{10}$, cycloalkyl, ($C_3$–$C_{10}$ cycloalkyl) $C_1$–$C_6$ alkyl;

$R^{12}$ is selected from H, aryl, heteroaryl, $C_1$–$C_6$ alkyl, $C_3$–$C_{10}$ cycloalkyl, ($C_3$–$C_{10}$ cycloalkyl) $C_1$–$C_6$ alkyl, optionally substituted with $OR^7$, $NR^8R^9$, $C_3$–$C_6$ aminocarbocycle, or $C_2$–$C_5$ aminoheterocycle;

$R^{13}$ is independently selected at each occurrence from H, $C_1$–$C_6$ alkyl, $C_3$–$C_{10}$ cycloalkyl, ($C_3$–$C_{10}$, cycloalkyl) $C_1$–$C_6$ alkyl, $C_2$–$C_6$ alkenyl, $C_2$–$C_6$ alkynyl, $C_1$–$C_6$ haloalkyl, with the proviso that when $R^7$ is $SO_2R^{13}$, $R^{13}$ cannot be H; and $R^{14}$ is H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl $C_2$–$C_4$ alkynyl, halo, or CN.

Preferred compounds of the present invention are those of formula I where X is N or CH, $R^1$ is H, $C_1$–$C_6$ alkyl, $C_3$–$C_{10}$ cycloalkyl, or ($C_3$–$C_{10}$ cycloalkyl) $C_1$–$C_6$ alkyl; $R^6$ is H, $C_1$–$C_6$ alkyl, $C_3$–$C_{10}$ cycloalkyl, or ($C_3$–$C_{10}$ cycloalkyl) $C_1$–$C_6$ alkyl.

This invention also encompasses, in additional embodiments, the novel compounds of formula I, and the salts and solvates thereof, as well as pharmaceutical formulations comprising a compound of formula I, or a pharmaceutically acceptable salt or solvate thereof, in combination with one or more pharmaceutically acceptable carriers, excipients, or diluents therefor.

This invention also encompasses methods to treat physiological disorders associated with an excess of neuropeptide Y, such as eating and cardiovascular disorders, which method comprises administering to a mammal in need of said treatment an effective amount of a compound of the formula I.

This invention also encompasses methods of selectively inhibiting binding of $NPY_1$ receptor s, which comprises contacting a compound of formula I with neuronal cells, wherein the compound is present in an amount effective to produce a concentration sufficient to inhibit binding of $NPY_1$ receptors in vitro.

DETAILED DESCRIPTION OF THE INVENTION

The current invention concerns the discovery that a select group of aminoalkyl substituted 4-amino pyrazolopyrimidines and 7-amino pyrazolo triazines, those of formula I, which are novel and useful neuropeptide Y receptor antagonists.

In certain situations, the compounds of formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by formula I, include, but are not limited to the compounds in Examples 1–306 and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, fornic, toluenesulfonic, methanesulfonic, nitric, benzoic, citric, tartaric, maleic, hydroiodic, alkanoic such as acetic, HOOC—$(CH_2)n$—COOH where n is 0–4, and the like. Those skilled in the art will recognize a wide variety of non-toxic pharmaceutically acceptable addition salts.

The present invention also encompasses the acylated prodrugs of the compounds of formula I. "Prodrugs" are considered to be any covalently bonded carriers which release the active parent drug of formula I in vivo when such prodrug is administered to a mammalian subject. Prodrugs of the compounds of the invention are prepared by modifying functional groups present in the compounds in such a way that the modifications are cleaved, either in routine manipulation or in vivo to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, and benzoate derivatives of alcohol and amine functional groups in the compounds of formula 1; and the like. Those skilled in the art will recognize various synthetic methodologies which may be employed to prepare non-toxic pharmaceutically acceptable addition salts and acylated prodrugs of the compounds encompassed by formula I.

Where a compound exists in various tautomeric forms, the invention is not limited to any one of the specific tautomers. The invention includes all tautomeric forms of a compound.

By "heteroatom" in the present invention is meant oxygen or sulfur, or a nitrogen atom optionally substituted by $C_1$–$C_6$ lower alkyl, $C_1$–$C_6$ arylalkyl, $C_1$–$C_{10}$ cycloalkyl, ($C_3$–$C_{10}$ cycloalkyl) $C_1$–$C_6$ alkyl, $C_2$–$C_8$ alkanoyl, $C_1$–$C_6$ sulfonyl.

By "alkyl", "lower alkyl", or "$C_1$–$C_6$ alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "cycloalkyl", or "$C_3$–$C_{10}$ cycloalkyl" in the present invention is meant alkyl groups having 3–10 carbon atoms forming a mono-, bi-, or polycyclic ring system, such as, for example, cyclopropyl, cyclobutyl, cyclopentyl, cyclohexyl, cycloheptyl, norbornyl, and the like.

By "(cycloalkyl)alkyl", "lower (cycloalkyl)alkyl", or ($C_3$–$C_{10}$ cycloalkyl) $C_1$–$C_6$ alkyl in the present invention is meant a straight or branched alkyl substituent formed of 1 to 6 carbon atoms attached to a mono-, bi, or polycyclic ring system having 3–10 carbon atoms, such as, for example, cyclopropylmethyl, cyclobutylmethyl, cyclopentylmethyl, cyclohexylmethyl, cycloheptylmethyl, and the like.

The term "$C_2$–$C_6$ alkenyl" in the present invention means hydrocarbon chains having 2 to 6 carbons in a straight or branched arrangement and containing one or more unsaturated carbon-carbon double bonds which may occur in any stable point along the chain, such as, for example, ethenyl, allyl, isopropenyl, and the like.

By "cycloalkenyl" or "$C_3$–$C_{10}$ cycloalkenyl" in the present invention is meant alkyl groups having 3–10 carbon atoms forming a mono-, bi, or polycyclic ring system having 3–10 carbon atoms and containing one or more carbon-carbon double bonds which may occur in any stable point in the ring, such as, for example, cyclopentenyl, cyclohexenyl, or cycloheptenyl.

The term "$C_2$–$C_6$ alkynyl" in the present invention means hydrocarbon chains having 2 to 6 carbons in a straight or branched arrangement and containing one or more unsaturated carbon-carbon triple bonds which may occur in any stable point along the chain, such as, for example, ethynyl, propargyl, and the like.

The term "aryl" in the present invention means a monocyclic or bicyclic aromatic group having preferably 6 to 10 carbon atoms, such as, for example, phenyl or naphthyl.

The term "heteroaryl" in the present invention means an aryl group in which one or more of the ring(s) carbon atoms have been replaced with a heteroatom. Such groups preferably have 4 to 10 carbon atoms and 1 to 4 heteroatoms, such as, for example, pyridyl, pyrimidinyl, triazinyl, imidazolyl, oxazolyl, isoxazolyl, indolyl, pyrrolyl, pyrazolyl, quinolinyl, isoquinolinyl, thiazolyl, benzothiadiazolyl, triazolyl, triazinyl, pyrazinyl, furanyl, thienyl, benzothienyl, benzofuranyl, tetrazolyl.

The term "heterocycle", "heterocycle" or "heterocycloalkyl" in the present invention means a saturated or partially saturated heteroaryl group.

By "$C_1$–$C_6$ arylalkyl" or "$C_1$–$C_6$ heteroarylalkyl" in the present invention is meant a branched or straight-chain alkyl group having 1–6 carbon atoms and substituted on one of the carbon atoms by an optionally substituted aryl or heteroaryl ring, such as, for example, benzyl, phenethyl, methylpyridyl, ethylpyridyl, and the like.

By "$C_5$–$C_8$ arylcycloalkyl" in the present invention is meant cycloalkyl groups having 5–8 carbon atoms and fused to an aryl group, such as, for example, 1,2,3,4 tetrahydronaphthalenyl, 2,3-dihydrobenzothienyl, or 2,3-dihydobenzofuranyl.

By "$C_5$–$C_8$ heteroarylcycloalkyl" in the present invention is meant cycloalkyl groups having 5–8 carbon atoms fused to a heteroaryl group, such as, for example, 1,2,3,4 tetrahydroquinolyl, 2,3-dihydrobenzothienyl, 2,3-dihydobenzofuranyl, or indolinyl.

By "alkoxy", "$C_1$–$C_6$ alkoxy", or "$C_1$–$C_6$ alkyloxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By "cycloalkoxy", "$C_3$–$C_{10}$ cycloalkoxy", or "$C_3$–$C_{10}$ cycloalkyloxy" in the present invention is meant a group formed by an oxygen atom attached to a mono-, bi, or polycyclic ring system having 3–10 carbon atoms, such as, for example, cyclopropoxy, cyclobutoxy, cyclopentoxy, cyclohexoxy, or cycloheptoxy.

By "(cycloalkyl)alkyloxy", "($C_3$–$C_{10}$ cycloalkyl) $C_1$–$C_6$ alkoxy", or "($C_3$–$C_{10}$ cycloalkyl) $C_1$–$C_6$ alkyloxy" in the present invention is meant a group formed by an oxygen atom attached to a 1–6 carbon chain linked to a mono-, bi, or polycyclic ring system having 3–10 carbon atoms, such as, for example, cyclopropylmethyloxy, cyclobutylmethyloxy, cyclopentylmethyloxy, cyclohexylmethyloxy, cycloheptylmethyloxy, and the like.

By "$C_3$–$C_6$ aminocarbocycle" is meant a cyclic amino group formed by a nitrogen contained in a ring having 3 to 6 carbon atoms, such as, for example, azetidino, pyrrolidino, piperidino, perhydroazepino.

By "$C_2$–$C_5$ aminoheterocycle" is meant a cyclic amino group formed by a nitrogen contained in a ring having 2 to 5 carbon atoms and one other heteroatom, such as, for example, morpholino, thiomorpholino, piperazino.

By the terms "halo" or "halogen" in the present invention is meant fluoro, chloro, bromo, and iodo. "Haloalkyl" is intended to include both branched and straight-chain alkyl having the specified number of carbon atoms substituted with 1 or more halogens.

The term "$C_2$–$C_8$ alkanoyl" means an acyl group with 2 to 8 carbon atoms in a linear, branched, or $C_3$–$C_{10}$ cycloalkyl arrangement, optionally substituted with 1 to 5 substituents independently selected at each occurrence from halogen, trifluoromethyl, $OR^7$, $NR^8R^9$, $CONR^8R^9$, $COOR^7$, or CN.

The term "$C_1$–$C_6$ alkyl sulfonyl" means an alkylsulfonyl group containing 1 to 6 carbon atoms in a linear, branched, or $C_3$–$C_7$ cycloalkyl arrangement.

The term "substituted" means that one or more hydrogen on the designated atom is replaced by the specified group, provided that the valence on the designated atom is not exceeded, and that a chemically stable compound results from the substitution.

A stable compound is defined herein as one that can be isolated, characterized, and tested for biological activity.

The term "oxo" (i.e. =O) indicates that two geminal hydrogen atoms are replaced by a double-bond oxygen group.

The term "hydroximino" (i.e. =N—OH) ) indicates that two geminal hydrogen atoms are replaced by a double-bond nitrogen atom substituted with a hydroxyl group.

The term "$C_1$–$C_6$ alkoximino" (i.e. =N—O-Alkyl) indicates that two geminal hydrogen atoms are replaced by a double-bond nitrogen atom substituted with a $C_1$–$C_2$ alkoxy group, such as, for example, methoximino (=N—OMe).

In the present invention, some of the groups specifically mentioned above are defined as follows:

2-one-1,3-oxazolidinyl is

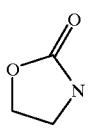

1-aza-bicyclo[4.4.0]decyl is

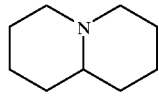

8-azabicyclo[3.2.1]octanyl is

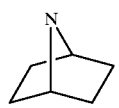

-continued (1,1-dioxo) tetrahydrothiopyranyl is

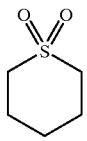

norbornyl is

quinuclidinyl is

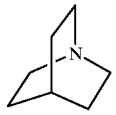

2-one-indolinyl is

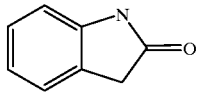

2-(methoximino)-perhydroazepin-6-yl is

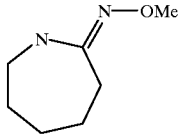

Unless specified, the point of attachment may occur in any stable point along the above-mentioned rings.

In the present invention, the term "potent" in the context of $NPY_1$ receptor antagonists qualifies a binding affinity with a Ki of less than 10 micromolar, preferably less than 1 micromolar, and more preferably less than 100 nanomolar in the human $NPY_1$ binding assay.

In the present invention, the term "selective" in the context of $NPY_1$ receptor antagonists qualifies a binding affinity with a Ki in the human $NPY_1$ binding assay that is 10-fold, preferably 100-fold, and more preferably 1000-fold, less than the Ki of the same compound measured in another receptor binding assay, in particular the $NPY_5$ and the $CRF_1$ receptor binding assays. Binding assays for the $NPY_5$ and $CR_1F$ receptors have been described, for example, in *J. Clin. Invest.*, 102, 2136 (1998) and in *Endocrinology* 116, 1653 (1985), respectively.

As the compounds of formula I are selective antagonists of the $Y_1$ receptor, they are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a compound of formula I or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present locally. These physiological disorders may include: disorders or diseases pertaining to the heart, blood vessels or the renal system, such as vasospasm, heart failure, shock, cardiac hypertrophy increased blood pressure, angina, myocardial infarction, sudden cardiac death, arrhythmia, peripheral vascular disease, and abnormal renal conditions such as impaired flow of fluid, abnormal mass transport, or renal failure; conditions related to increased sympathetic nerve activity for example, during or after coronary artery surgery, and operations and surgery in the gastrointestinal tract; cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, and dementia; conditions related to pain or nociception; diseases related to abnormal gastrointestinal motility and secretion, such as different forms of ileus, urinary incontinence, and Crohn's disease; abnormal drink and food intake disorders, such as obesity, anorexia, bulimia, and metabolic disorders; diseases related to sexual dysfunction and reproductive disorders; conditions or disorders associated with inflammation; respiratory diseases, such as asthma and conditions related to asthma and bronchoconstriction; and diseases related to abnormal hormone release, such as leutinizing hormone, growth hormone, insulin, and prolactin.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachid oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachid oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 50 mg per kilogram of body weight per day are useful in the treatment of the above-indicated conditions (about 0.5 mg to about 3 g per patient per day), although higher amounts for example up to 140 mg/kg/day may be appropriate in some circumstances. The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

In appropriate cases, the compounds of the invention may be employed in combination with other active agents. The invention therefore also - provides pharmaceutical combination compositions comprising a therapeutically effective amount of a composition comprising: (a) first compound, said first compound being a compound of the type described above a prodrug thereof, or a pharmaceutically acceptable salt of said compound or of said prodrug; and (b) a second compound, said second compound being a agonist, a thyromimetic, an eating behavior modifying agent or a NPY antagonist; and a pharmaceutical carrier, vehicle, diluent. Combinations may, for example comprise (a) first compound, said first compound being a compound as described above a prodrug thereof, or a pharmaceutically acceptable salt of said compound or of said prodrug; (b) a second compound, said second compound being an aldose reductase inhibitor, a glycogen phosphorylase inhibitor, a sorbitol dehydrogenase inhibitor, insulin metfornin, acarbose, a thiazolidinedione, a glitazone, rezulin, trogitalazone, a sulfonylurea, glipazide, glyburide, or chlorpropamide; (c) a pharmaceutical carrier, vehicle, or diluent. In other cases, a kit may be appropriate comprising: (a) first compound, said first compound being a compound of claim 24 or 25, a prodrug thereof, or a pharmaceutically acceptable salt of said compound or of said prodrug; (b) a second compound, said second compound being a $\beta_3$ agonist, a thyromimetic, an eating behavior modifying agent or a NPY antagonist; and a pharmaceutical carrier, vehicle, diluent; and (c) means for containing said first and second unit dosage forms wherein the amounts of the first and second compounds result in a therapeutic effect.

Preparation of Aminoalkyl Substituted Pyrazolo[1, 5,-a]-1,5-Pyrimidines and Pyrazolo[1,5-a]-1,3,5- Triazines Derivatives One general approach is to convert a heterocyclic core A and or a heterocyclic core B

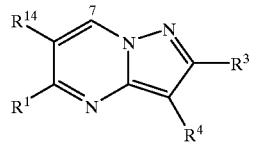

A

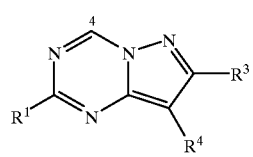

B to a compound that exhibits a $K_i$ of 5 micromolar or less in an assay of NPY receptor binding, wherein the substituents are as defined above by substituting the 7-position of the heterocyclic core A or the 4-position of the heterocyclic core B with a diamine group —N[$R^2$]—A—B—N[$R^6$]—$R^5$.

An illustration of preparation methods of compounds of the present invention is given in the Schemes below. In particular displacement of a leaving group Z, as in formula 10 (Scheme 1) by the appropriate substituted amine provides a method to convert the heterocyclic cores of the present invention, i.e. aryl or heteroaryl substituted pyrazolo[1,5,-a]-1,5-pyrimidines and pyrazolo[1,5-a]-1,3,5-triazines, into compounds that potently interact with the NPY1 receptor. Such transformations may require several consecutive chemical steps. Those having skill in the art will recognize that the starting materials may be varied and additional steps employed to produce compounds encompassed by the present invention. The disclosures of all articles and references mentioned in this application, including patents, are incorporated herein by reference.

SCHEME 1

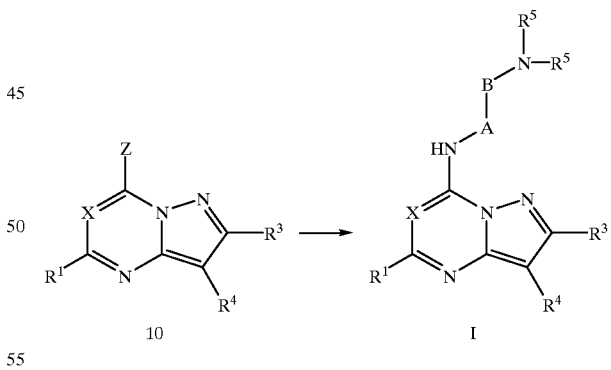

As illustrated in Scheme 1, compounds of formula I can be prepared from intermediate compounds of formula 10, where Z is halogen (preferably chloro or bromo), alkane sulfonyloxy, aryl sulfonyloxy or haloalkane sulfonyloxy, and X, $R^1$, $R^3$ and $R^4$ are defined above, using the procedures outlined below.

Compounds of formula 10 react with an amine of formula $H_2N$—A—B—N[$R^6$]—$R^5$, where A,B, $R^5$ and $R^6$ are defined as above, in the presence or absence of a base in the presence or absence of an inert solvent at reaction temperatures ranging from −78° C. to 250° C. to generate compounds of formula I. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal bicarbonates, alkali metal bis-(trialkylsilyl)amides (preferably lithium or sodium (trimethylsilyl)amide), trialkylamines (preferably N,N-di-isopropyl-N-ethyl amine or triethylamine), arylamines (preferably 4-dimethyl aniline), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes (1–10 carbons and 1–10 halogens) (preferably dichloromethane). Preferred reaction temperatures range from 0° C. to 140° C.

SCHEME 2

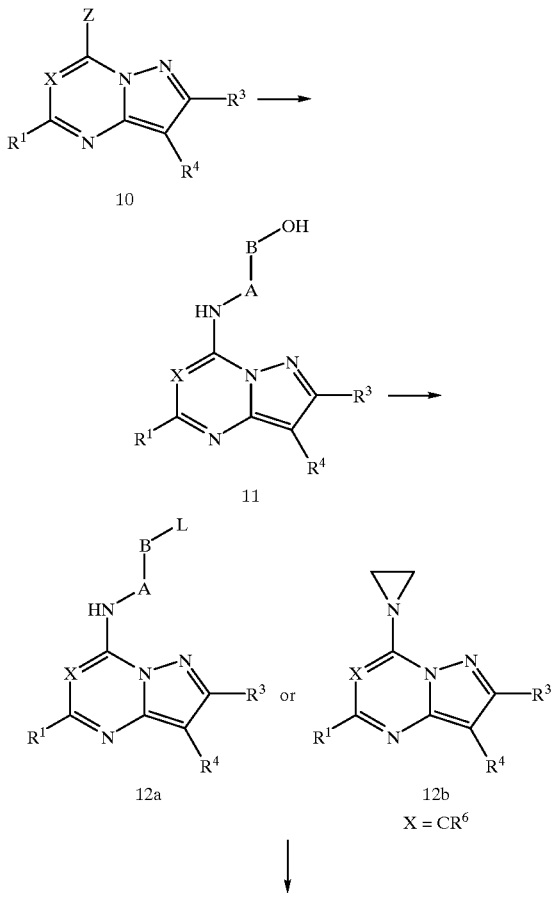

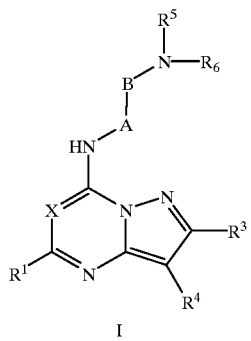

Alternatively, as shown in Scheme 2, compounds of formula I can be obtained by first reacting a compound of formula 10 with an amino alcohol of formula $H_2N$—A—B—OH, where A and B are defined as above, in the presence or absence of a base in the presence or absence of an inert solvent at reaction temperatures ranging from −78° C. to 250° C. to generate intermediates of formula 11. Reacting a compound of formula 11 with a halogenating agent or sulfonylating agent in the presence or absence of a base in the presence or absence of an inert solvent at reaction temperatures ranging from −78° C. to 250° C. to afford products of formula 12a (where Z is halogen, alkane sulfonyloxy, aryl sulfonyloxy or haloalkane sulfonyloxy) or 12b when A and B are both $CH_2$ and X is $CR^{14}$. Halogenating agents include, but are not limited to, $SOCl_2$, $POCl_3$, $PCl_3$, $PCl_5$, $POBr_3$, $PBr_3$, $PBr_5$., $CCl_4/PPh_3$. Sulfonylating agents include, but are not limited to, alkanesulfonyl halides or anhydrides (preferably methanesulfonyl chloride or methanesulfonic anhydride), aryl sulfonyl halides or anhydrides (such as p-toluenesulfonyl chloride or anhydride), or haloalkylsulfonyl halides or anhydrides (preferably trifluoromethanesulfonic anhydride). Bases may include, but are not limited to, trialkylamines (preferably N,N-di-isopropyl-N-ethyl amine or triethylamine), bicyclic amidines (preferably DBU), anilines (preferably N-dimethyl aniline), or heteroaromatic amines (preferably pyridine). Inert solvents may include, but are not limited to, lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes with 1–10 carbons and 1–10 halogens (preferably dichloromethane). Preferred reaction temperatures range from −20° C. to 100° C. Compounds of formula 12a or 12b can then be reacted with an amine of formula $HN[R^6]$—$R^5$, where $R^5$ and $R^6$ are defined as above, to give a compound of formula I. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal bicarbonates, alkali metal bis-(trialkylsilyl)amides (preferably lithium or sodium (trimethylsilyl)amide), trialkylamines (preferably N,N-di-isopropyl-N-ethyl amine or triethylamine), arylamines (preferably 4-dimethyl aniline), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-meihylpyrrolidin-2-one), dialkylsulfoxides (preferably dimethylsulfoxide), aromatic hydrocarbons (preferably benzene or toluene), or haloalkanes (1–10 carbons and 1–10 halogens) (preferably dichloromethane). Preferred reaction temperatures range from 0° C. to 140° C.

metal or alkaline earth metal borohydrides (preferably lithium or sodium borohydride), borane (preferably complexed with dimethyl sulfide or tetrahydrofuran), dialkylboranes (such as di-isoamylborane), alkali metal aluminum hydrides (preferably lithium aluminum hydride), alkali metal (trialkoxy)aluminum hydrides (such as triethoxyaluminum hydride), dialkyl aluminum hydrides (such as di-isobutyl aluminum hydride), alane (preferably complexed with dimethylethylamine). Inert solvents may include, but are not limited to, alkyl alcohols (1–6 carbons) (preferably methanol, ethanol, or tert-butanol), dialkyl ethers (preferably diethyl ether), cyclic ethers (preferably tetrahydrofaran or 1,4-dioxane), aromatic hydrocarbons (preferably benzene or toluene). Preferred reaction temperatures range from –78° C. to 100° C.

SCHEME 3

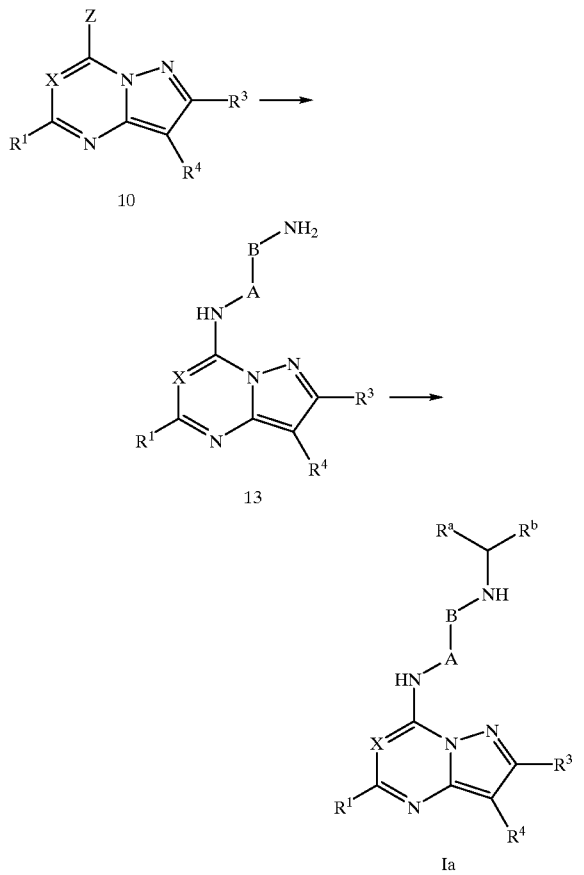

SCHEME 4

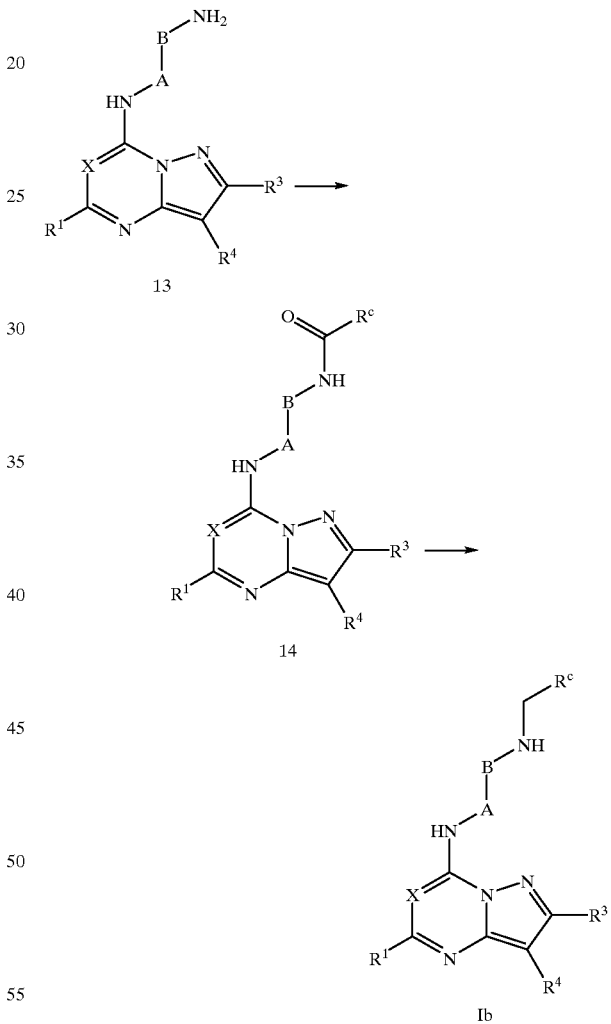

A subset of compounds of formula I, described under formula Ia in Scheme 3, can be obtained by first reacting a compound of formula 10 with a diamine of formula H$_2$N—A—B—NH$_2$, where A and B are defined as above, in the presence or absence of a base in the presence or absence of an inert solvent at reaction temperatures ranging from –78° C. to 250° C. to generate intermediates of formula 13. Reaction of a compound of formula 13 with a ketone of Formula R$^a$—C=O—R$^b$ or an aldehyde of Formula R$^a$—C=O—R$^b$ where R$^b$=H, in the presence of a reducing agent provides a compound of formula Ia, where the grouping R$^a$—CH—R$^b$ corresponds to R$^5$ in formula I, as defined above. Reducing agents include, but are not limited to, alkali Alternatively, as illustrated in Scheme 4, a subset of compounds of formula I, described under formula Ib, can be obtained by first reacting a compound of formula 13 with an activated acid of formula R$^c$—C=O—Z, where Z is halo (preferably chloro), O-acyl (preferably O—C=O—R$^c$), in the presence or absence of a base in the presence or absence of an inert solvent at reaction temperatures ranging from –78° C. to 250° C. to generate an amide intermediate of formula 14. Reaction of a compound of formula 14 with a reducing agent provides a compound of formula Ib, where the grouping $R^c$—$CH_2$ corresponds to $R^5$ in formula I, as defined above. Reducing agents include, but are not limited to, alkali metal or alkaline earth metal borohydrides (preferably lithium or sodium borohydride), borane (preferably complexed with dimethyl sulfide or tetrahydrofuran), dialkylboranes (such as di-isoamylborane), alkali metal aluminum hydrides (preferably lithium aluminum hydride), alkali metal (trialkoxy)aluminum hydrides (such as triethoxyaluminum hydride), dialkyl aluminum hydrides (such as di-isobutyl aluminum hydride), alane (preferably complexed with dimethylethylamine). Inert solvents may include, but are not limited to, alkyl alcohols (1–6 carbons) (preferably methanol, ethanol, or tert-butanol), dialkyl ethers (preferably diethyl ether), cyclic ethers (preferably tetrahydrofuran or 1,4-dioxane), aromatic hydrocarbons (preferably benzene or toluene). Preferred reaction temperatures range from −78° C. to 100° C.

(preferably 4-dimethyl aniline), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes (1–10 carbons and 1–10 halogens) (preferably dichloromethane). Compounds of formula 15 react with a protic acid in the presence or absence of an inert solvent at reaction temperatures ranging from −78° C. to 250° C., followed by aqueous work-up to generate compounds of formula 16. Inert solvents may include, but are not limited to dialkyl ethers (preferably diethyl ether), cyclic ethers

SCHEME 5

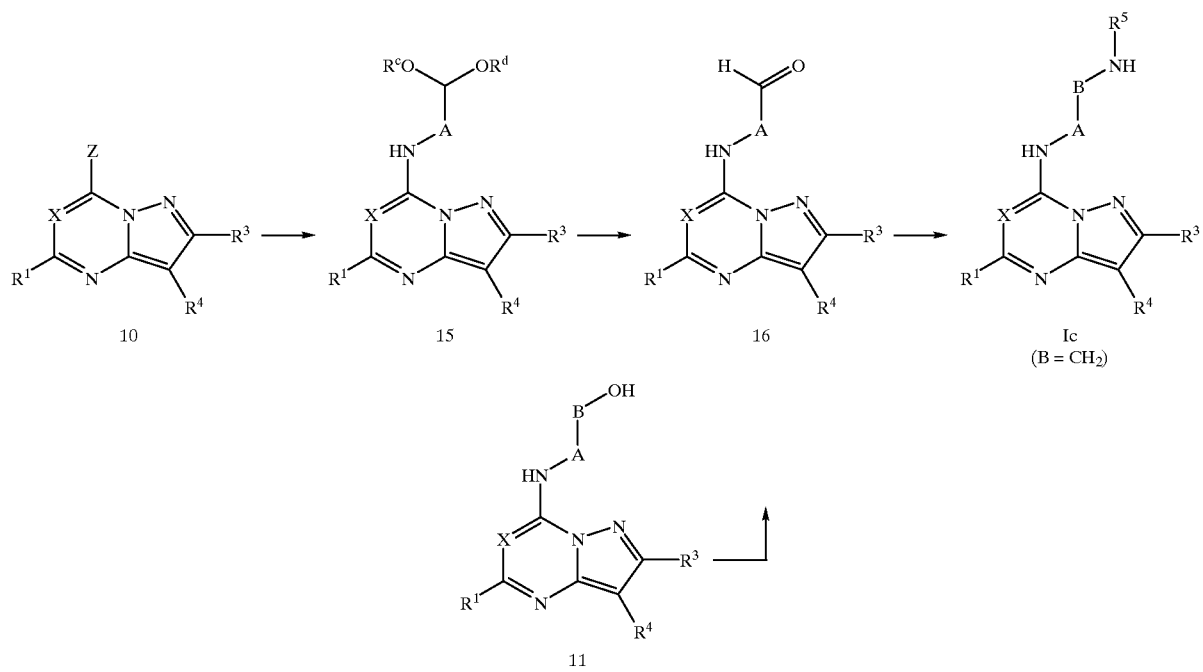

Alternatively, a subset of compounds of formula I, described under formula Ic in Scheme 5, can be obtained by first reacting a compound of formula 10 with an amine of formula $H_2N$—A—$CH(OR^c)(OR^d)$, where A is defined above, and $R^c$ and $R^d$ are $C_1$–$C_6$ lower alkyls or, taken together, complete a ketal group, such as, for example a dioxane or dioxolane group, in the presence or absence of a base in the presence or absence of an inert solvent at reaction temperatures ranging from −78° C. to 250° C. to generate compounds of formula 15. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal bicarbonates, alkali metal bis-(trialkylsilyl)amides (preferably lithium or sodium (trimethylsilyl)amide), trialkylamines (preferably N,N-di-isopropyl-N-ethyl amine or triethylamine), arylamines (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes (1–10 carbons and 1–10 halogens) (preferably dichloromethane). Protic acids include, but are not limited to, formic acid, acetic acid, trifluoroacetic acid, hydrochloric acid, methane sulfonic acid. Alternatively, compounds of formula 16 can be obtained by oxidation of compounds of formula 11 where B=$CH_2$. Oxidizing agents include, but are not limited to, transition metal oxides, such as $CrO_3$ or $MnO_2$, pyridine-chromium complexes, such as $CrO_3.C_5H_5N$, pyridinium dichromate or pyridinium chlorochromate, or an oxalyl chloride-DMSO-triethylamine reagent (Swern oxidation). Compounds of formula 16 react with amines of formula $H_2N$—$R^5$, where $R^5$ is defined above, in the presence of a reducing agent in the presence or absence of an inert solvent in the presence or absence of a protic acid at temperatures ranging from −78° C. to 100° C., to give compounds of formula Ic. Reducing agents include, but are not limited to, alkali metal or alkaline earth metal borohydrides (preferably lithium or sodium borohydride), borane preferably complexed with dimethyl sulfide or tetrahydrofuran), dialkylboranes (such as di-isoamylborane), alkali metal aluminum hydrides (preferably lithium aluminum hydride), alkali metal (trialkoxy)aluminum hydrides (such as triethoxyaluminum hydride), dialkyl aluminum hydrides (such as di-isobutyl aluminum hydride), alane (preferably complexed with dimethylethylamine). Inert solvents may include, but are not limited to, alkyl alcohols (1–6 carbons) (preferably methanol, ethanol, or tert-butanol), dialkyl ethers (preferably diethyl ether), cyclic ethers (preferably tetrahydrofuran or 1,4-dioxane), aromatic hydrocarbons (preferably benzene or toluene).

SCHEME 6

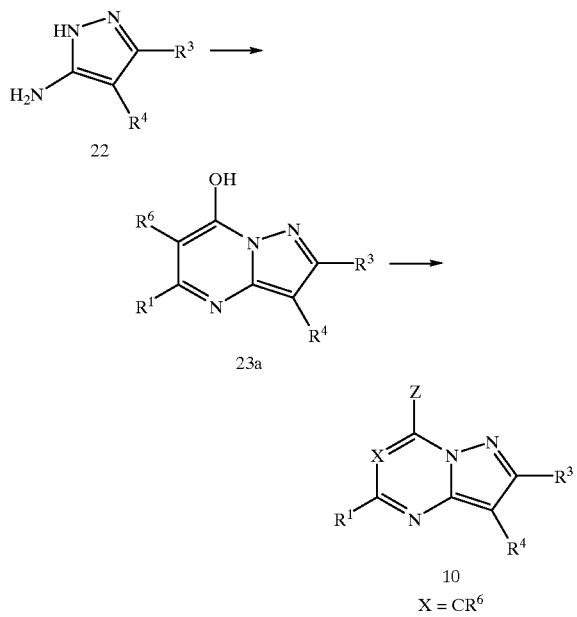

When X is $CR^{14}$, as defined above, compounds of formula 10 may be obtained from compounds of formula 22, as shown in Scheme 6. Compounds of formula 22 can be reacted with compounds of formula $R^1$—C=O—CH($R^{14}$)—C=O—$R^c$, where $R^1$ and $R^{14}$ are defined above, and $R^c$ is halogen, cyano, lower alkoxy (1–6 carbons), or lower alkanoyloxy (1–6 carbons), in the presence or absence of a base in an inert solvent at reaction temperatures ranging from −50° C. to 250° C. to afford compounds of formula 23a. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal hydroxides, alkali metal bis-(trialkylsilyl)amides (preferably lithium or sodium (trimethylsilyl)amide), trialkylamines (preferably N,N-di-isopropyl-N-ethyl amine or triethylamine), bicyclic amidines (preferably DBU), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), water, dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene). Compounds of formula 23a can then be reacted with a halogenating agent or sulfonylating agent in the presence or absence of a base in the presence or absence of an inert solvent at reaction temperatures ranging from −78° C. to 250° C. to afford products of formula 10 (where Z is halogen, alkane sulfonyloxy, aryl sulfonyloxy or haloalkane sulfonyloxy and X is $CR^{14}$). Halogenating agents include, but are not limited to, $SOCl_2$, $POCl_3$, $PCl_3$, $PCl_5$, $POBr_3$, $PBr_3$, or $PBr_5$. Sulfonylating agents include, but are not limited to, alkanesulfonyl halides or anhydrides (preferably methanesulfonyl chloride or methanesulfonic anhydride), aryl sulfonyl halides or anhydrides (such as p-toluenesulfonyl chloride or anhydride), or haloalkylsulfonyl halides or anhydrides (preferably trifluoromethanesulfonic anhydride). Bases may include, but are not limited to, trialkylamines (preferably N,N-di-isopropyl-N-ethyl amine or triethylamine), bicyclic amidines (preferably DBU), anilines (preferably N-dimethyl aniline), or heteroaromatic amines (preferably pyridine). Inert solvents may include, but are not limited to, lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes with 1–10 carbons and 1–10 halogens (preferably dichloromethane). Preferred reaction temperatures range from −20° C. to 100° C.

SCHEME 7

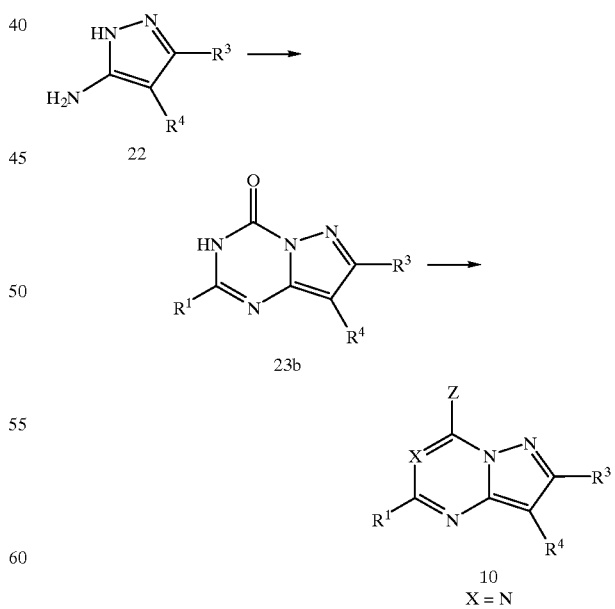

As shown in Scheme 7, when X is N, compounds of formula 22 can be reacted with compounds of formula $R^1$—C=N(COOR$^g$)—OR$^f$, where $R^1$ is defined above, and $R^g$ is lower alkyl (1–6 carbons), and $R^f$ is halogen, cyano, lower alkoxy (1–6 carbons), or lower alkanoyloxy (1–6 carbons), in the presence or absence of a base in an inert solvent at reaction temperatures ranging from −50° C. to 250° C. to afford compounds of formula 23b. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal hydroxides, alkali metal bis-(trialkylsilyl)amides (preferably lithium or sodium (trimethylsilyl)amide), trialkylamines (preferably N,N-di-isopropyl-N-ethyl amine or triethylamine), bicyclic amidines (preferably DBU), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), water, dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), heteroaromatic hydrocarbons (preferably pyridine). Compounds of formula 23b can then be reacted with a halogenating agent or sulfonylating agent in the presence or absence of a base in the presence or absence of an inert solvent at reaction temperatures ranging from −78° C. to 250° C. to afford products of formula 10 (where Z is halogen, alkane sulfonyloxy, aryl sulfonyloxy or haloalkane sulfonyloxy and X is N). Halogenating agents include, but are not limited to, $SOCl_2$, $POCl_3$, $PCl_3$, $PCl_5$, $POBr_3$, $PBr_3$, or $PBr_5$. Sulfonylating agents include, but are not limited to, alkanesulfonyl halides or anhydrides (preferably methanesulfonyl chloride or methanesulfonic anhydride), aryl sulfonyl halides or anhydrides (such as p-toluenesulfonyl chloride or anhydride), or haloalkylsulfonyl halides or anhydrides (preferably trifluoromethanesulfonic anhydride). Bases may include, but are not limited to, trialkylamines (preferably N,N-di-isopropyl-N-ethyl amine or triethylamine), bicyclic amidines (preferably DBU), anilines (preferably N-dimethyl aniline), or heteroaromatic amines (preferably pyridine). Inert solvents may include, but are not limited to, lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes with 1–10 carbons and 1–10 halogens (preferably dichloromethane). Preferred reaction temperatures range from −20° C. to 100° C.

SCHEME 8

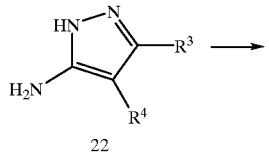

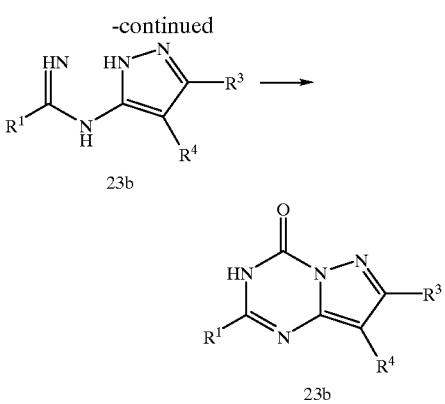

Alternatively, as illustrated in Scheme 8, compounds of formula 23b can be obtained by first reacting compounds of formula 22 with compounds of the formula $R^1$—(C=NH)—$OR^h$, where $R^1$ is defined above and $R^g$ is a lower alkyl group (preferably methyl or ethyl), in the presence or absence of an acid in an inert solvent to give an intermediate of formula 24. Compounds of formula 24 react with a compound of formula $R^i$—C=O—$R^j$, where $R^i$ and $R^j$ are each or independently lower alkoxy (preferably methoxy or ethoxy), 1-imidazolyl, halo, aryloxy (preferably 4-nitrophenoxy) in the presence or absence of an inert solvent to afford compounds of formula 23b. Bases may include, but are not limited to, alkali metals (preferably sodium), alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal hydroxides, alkali metal bis-(trialkylsilyl)amides (preferably lithium or sodium (trimethylsilyl)amide), trialkylamines (preferably N,N-di-isopropyl-N-ethyl amine or triethylamine), bicyclic amidines (preferably DBU), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), water, dialkyl ethers (preferably diethyl ether), cyclic ethers (preferably tetrahydrofaran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene).

SCHEME 9

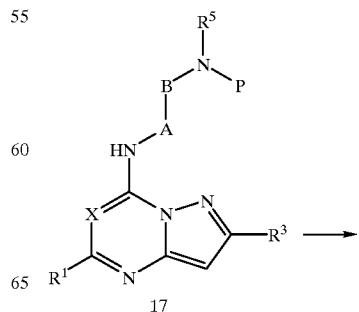

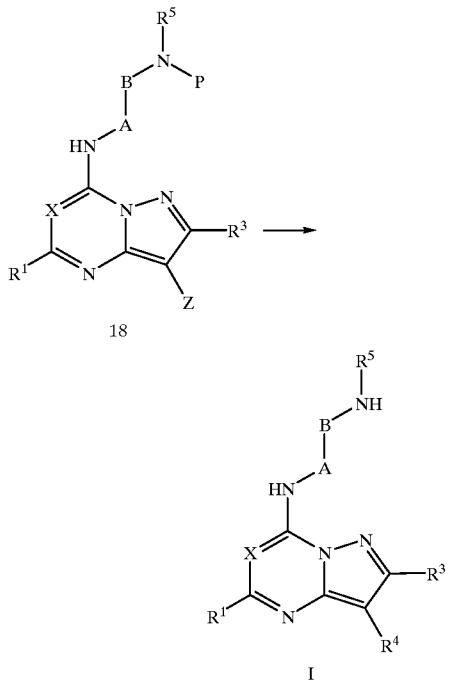

According to Scheme 9, compounds of formula I can also be prepared from compounds of formula 17 (prepared using the methods applicable to the synthesis of compounds of formula I), where P is H or an appropriate amino protecting group. Such groups, known in the art of organic synthesis for the protection of amines, include those listed in "Protective Groups in Organic Synthesis", by Greene and Wuts [John Wiley & Sons, N.Y., 1991]. Examples of amine protecting groups include, but are not limited to, acyl types (such as formyl, trifluoroacetyl, phthalyl, and p-toluenesulfonyl), carbamate types (such as benzyloxycarbonyl, t-butoxycarbonyl, 9-fluorenymethyloxycarbonyl, allyloxycarbonyl, and 2,2,2-trichloroethyloxycarbonyl), alkyl types (such as benzyl and triphenylmethyl). Reacting compounds of formula 17 with a halogenating agent provides compounds of formula 18 where X is Br, Cl, or I. Compounds of formula 18 react with a compound of formula $R^4M$ (where M is alkali metal, ZnCl, ZnBr, MgBr, MgCl, MgI, $CeCl_2$, $CeBr_2$, copper halides, $B(OH)_2$, $B(O$-lower alkyl$)_2$, or Sn(lower alkyl)$_3$) in the presence or absence of an organometallic catalyst in the presence or absence of a base in an inert solvent at temperatures ranging from $-100°$ C. to $200°$ C. to give compounds of formula I (or their N-protected forms which can then be deprotected). Similar conditions have been described in WO 98/54093. Those skilled in the art will recognize that the reagents $R^4M$ may be generated in situ. Organometallic catalysts include but are not limited to, palladium phosphine complexes (such as $Pd(PPh_3)_4$), palladium halides or alkanoates (such as $PdCl_2(PPh_3)_2$ or $Pd(OAc)_2$), or nickel complexes (such as $NiCl_2(PPh_3)_2$). Bases may include, but are not limited to, alkali metal alkoxides (1–6 carbons) (preferably sodium methoxide, sodium ethoxide, or sodium tert-butoxide), alkali metal carbonates or bicarbonates, alkali metal hydroxides, alkali metal phosphates, or trialkylamines (preferably N,N-di-isopropyl-N-ethyl amine or triethylamine). Inert solvents may include, but are not limited to, lower alkanenitriles (1–6 carbons) (preferably acetonitrile), water, dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides(preferably dimethylsulfoxide), aromatic hydrocarbons (preferably benzene or toluene).

SCHEME 10

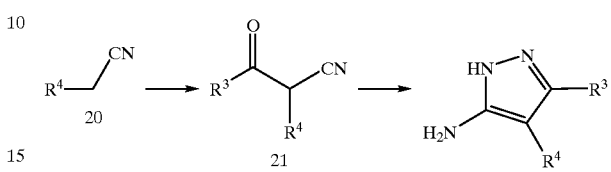

As shown in Scheme 10, compounds of formula 22 may be obtained from compounds of formula 20, where $R^4$ is defined as above. Compounds of formula 20 are reacted with compounds of formula $R^3$—C=O—$R^c$, where $R^3$ is defined above and $R^c$ is halogen, cyano, lower alkoxy (1–6 carbons), or lower alkanoyloxy (1–6 carbons), in the presence of a base in an inert solvent at reaction temperatures ranging from $-78°$ C. to $200°$ C. to afford compounds of formula 21. Bases may include, but are not limited to, alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal hydroxides, alkali metal bis-(trialkylsilyl)amides (preferably lithium or sodium (trimethylsilyl)amide), trialkylamines preferably N,N-di-isopropyl-N-ethyl amine or triethylamine), bicyclic amidines (preferably DBU), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), water, dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides preferably dimethylsulfoxide), aromatic hydrocarbons (preferably benzene or toluene). Alternatively, compounds of formula 20 may be reacted with a solvent of formula $R^3$—C=O—$R^c$, where $R^3$ is defined above and $R^c$ is lower alkoxy (1–6 carbons), in the presence of an alkali metal (preferably sodium) at reaction temperatures ranging from $-78°$ C. to $200°$ C. to afford compounds of formula 21. Compounds of formula 21 may be reacted with hydrazine (hydrate or hydrochloride salt) in an inert solvent, at reaction temperatures ranging from $0°$ C. to $200°$ C., preferably $70°$ C. to $150°$ C., to afford compounds of formula 22. Inert solvents may include, but are not limited to, water, lower alkanoic acids (preferably formic, acetic, or trifluoro acetic acid), alkyl alcohols (1–8 carbons) (preferably methanol or ethanol), lower alkanenitriles (1–6 carbons) (preferably acetonitrile), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene).

SCHEME 11

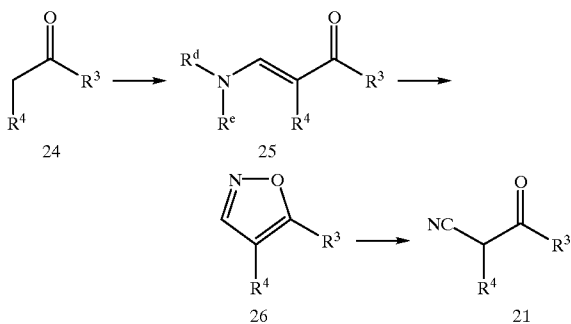

Alternatively, compounds of formula 21 can be obtained, as illustrated in Scheme 11, by first reacting compounds of formula 24 with dialkyl formamide dialkyl acetal of formula $(R^dR^e)N$—$CH(OR^f)_2$ where $R^d$, $R^e$, and $R^f$ are each or independently $C_1$–$C_6$ lower alkyl (preferably methyl) in the presence or absence of an inert solvent at reaction temperatures ranging from 0° C. to 250° C., preferably between 70° C. and 150° C. to provide compounds of formula 25. Inert solvents may include, but are not limited to, lower alkanenitriles (1–6 carbons) (preferably acetonitrile), dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene), or haloalkanes with 1–10 carbons and 1–10 halogens (preferably dichloromethane). Compounds of formula 25 can be reacted with hydroxylamine salt (preferably hydrochloride) in the presence or absence of an inert solvent at reaction temperatures ranging from 0° C. to 250° C., preferably between 70° C. and 200° C. to provide oxazoles of formula 26. Inert solvents may include, but are not limited to, alkyl alcohols (1–8 carbons) (preferably methanol, ethanol, or tert-butanol), lower alkanenitriles (1–6 carbons) (preferably acetonitrile), water, dialkyl ethers (preferably diethyl ether), cyclic ethers (preferably tetrahydrofuran or 1,4-dioxane), N,N-dialkylformamides (preferably dimethyl formamide), N,N-dialkylacetamides (preferably dimethyl acetarmide), cyclic amides (preferably N-methylpyrrolidin-2-one), dialkylsulfoxides (preferably dimethylsulfoxide), aromatic hydrocarbons (preferably benzene or toluene). Oxazole intermediates of formula 26 can be reacted with a base in the presence or absence of an inert solvent at reaction temperatures ranging from 0° C. to 200° C. Bases may include, but are not limited to, alkali hydroxides (preferably sodium or potassium hydroxide), alkali metal hydrides (preferably sodium hydride), alkali metal alkoxides (1–6 carbons) (preferably sodium methoxide, sodium ethoxide, or sodium tert-butoxide), alkaline earth metal hydrides, alkali metal dialkylamides (preferably lithium diisopropylamide), alkali metal carbonates, alkali metal hydroxides, alkali metal bis-(trialkylsilyl)amides (preferably lithium or sodium bis-(trimethylsilyl)amide), trialkylamines (preferably N,N-di-isopropyl-N-ethyl amine or triethylamine), bicyclic amidines (preferably DBU), or heteroaromatic amines (preferably pyridine). Inert solvents may include, but are not limited to, alkyl alcohols (1–8 carbons) (preferably methanol, ethanol, or tert-butanol), lower alkanenitriles (1–6 carbons) (preferably acetonitrile), water, dialkyl ethers (preferably diethyl ether), cyclic ethers (preferably tetrahydrofuran or 1,4-dioxane), N,N-dialkylformamnides (preferably dimethyl formamide), N,N-dialkylacetamides (preferably dimethyl acetamide), cyclic amides (preferably N-methylpyrrolidin-2-one), dialkylsulfoxides (preferably dimethylsulfoxide), aromatic hydrocarbons (preferably benzene or toluene).

EXAMPLES

The following examples are provided to describe the invention in further details. These examples, which set forth the best mode presently contemplated for carrying the invention, are intended to illustrate and not to limit the invention.

Commercial reagents were used without further purification. THF refers to tetrahydrofuran. LDA refers to lithium diisopropylamide and DBU refers to 1,8-diazabicyclo[5.4.0]undec-7-ene. Room or ambient temperature refers to 20° C. to 25° C. Concentration implies the use of a rotary evaporator. TLC refers to thin layer chromatography. Mass spectral data were obtained either by CI or APCI methods. Other commonly used abbreviations are: Ph is phenyl, Me is methyl, Et is ethyl, Pr is n-propyl, iPr is isopropyl, Bu is butyl, iBu is isobutyl ($CH_2$—$CHMe_2$), tBu is tert-butyl, cBu is cyclobutyl, Pent is n-pentyl, cPent is cyclopentyl, cHex is cyclohexyl, Py is pyridyl, MeOH means methanol, EtOH means ethanol, EtOAc means ethyl acetate, $Et_2O$ means diethyl ether, $CH_2Cl_2$ means methylene chloride, DMSO means dimethyl sulfoxide, NMP means N-methyl pyrrolidone, THF means tetrahydrofuran, DMF means dimethyl formamide, EX means example.

The numbering system used to describe the compounds of the present invention is as follows:

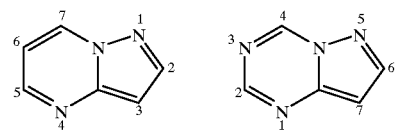

Example 1

Preparation of 7-(2-(perhydro-2H-pyran-4-ylamino) ethylamino)-2,5-dimethyl-3-(4-chloro-2,6-dimethylphenyl)-pyrazolo[1,5-a] pyrimidine (formula I where X is CH, $R^1$ is $CH_3$, $R^2$ is H, A is $CH_2$, B is $CH_2$, R3 is $CH_3$, $R^4$ is 2,6-dimethyl-4chlorophenyl, $R^5$ is perhydro-2H-pyran-4-yl)

A. 4-Bromo-3,5-dimethyl chlorobenzene

Slurry 2,6-dimethyl-4chloroaniline hydrochloride (23g, 193.11 g/mol) in $CH_2Cl_2$ (100 ml) and wash with saturated $NaHCO_3$ to generate the free base. Dry over $Na_2SO_4$, filter and evaporate down to a violet oil. Slurry up in 120 mL 6.0 N $H_2SO_4$ and stir vigorously at ambient temperature to break up larger pieces of solid. Cool to 0° C. in an ice/water bath, then portionwise over 15 minutes add a clear colorless solution of $NaNO_2$ in 50 mL $H_2O$. Maintain temperature 15° C. over course of addition, stirring under dry $N_2$. After 1 hour, carefully pour the cold reaction solution (solution A) into a second solution (solution B) containing 31.7 g CuBr in 33 mL aqueous HBr (48%) at ambient temperature. Let stand at ambient temperature until gas evolution ceases, then heat to 110° C. under $N_2$ while stirring. Stir for 3 hours, then cool to rt. Extract the aqueous layer with a (2:1) mixture of hexanes and $Et_2O$ (2×500 mL), then dry the combined organic layers over Na₂SO₄, filter and evaporate down to a brown oil. Triturate the oil with hexanes (100 mL), filter out the remaining solids and wash with copious amounts of hexanes. Evaporate the hexane layers to concentrate then flush through a pad of silica to remove baseline material, using hexanes as eluent. Evaporate to a clear colorless oil (13.5 g).

B. 4-Chloro-2,6-dimethyl benzaldehyde

Dissolve 4-bromo-3,5-dimethyl chlorobenzene (6.5 g) in 50 mL anhydrous THF and cool to −78° C. (dry ice/acetone) under N₂. Dropwise over 5 minutes add a solution of butyllithium (12.50 mL, 2.5M in hexanes) to the stirring solution of aryl bromide at −78° C. After 2 hours, dropwise add anhydrous DMF (5.0 mL) to the orange/red reaction solution and allow to warn to ambient temperature overnight while stirring under N₂. Evaporate the yellow solution down to a yellow oil and partition between H₂O (100 mL) and CH₂Cl₂ (100 mL). Extract the aqueous layer once with CH₂Cl₂, then pool the organic layers and dry over Na₂SO₄, filter and evaporate down to 5.0 g of yellow oil. Use without further purification. LCMS=169.6 (MH⁺)

C. 4-Chloro-2,6-dimethyl benzyl alcohol

Dissolve 4-chloro-2,6-dimethyl benzaldehyde (5.0 g, 168.64 g/mol) in 100 mL dry methanol. Cool to 0° C. while stirring under N₂. Portionwise add powdered NaBH₄ (0.76g, 37.85 g/mol) over 5 minutes. Stir at 0° C. for 2 hours, monitoring by TLC until aldehyde consumed, then evaporate to a yellow oil. Add H₂O (50 mL) and bring to pH. 7.0 by addition of saturated NH₄Cl. Extract the neutral aqueous layer with CH₂Cl₂ (3×75 mL) and dry the pooled organic layers over Na₂SO₄. Filter and concentrate to a yellow oil. Flush through a pad of silica to remove baseline material, then evaporate to a yellow solid (3.0 g) which can be used without further purification. LCMS=171.6 (MH⁺), 169.6 (M⁻)

D. 4-Chloro-2,6-dimethyl phenyl acetonitrile

Dissolve 4-chloro-2,6-dimethyl benzyl alcohol (2.8 g, 170.66 g/mol) in CH₂Cl₂ (25 mL) and cool to 0° C. under N₂. Dropwise add thionyl chloride (2.4 mL, 3.90 g, 118.9 g/mol) in 10 mL CH₂Cl₂ while stirring under N₂. After 2 hours, monitoring by TLC (alcohol Rf=0.35, chloride Rf1.0; using 20% EtOAc/80% hexanes as eluent), quench the reaction carefully by addition of saturated NaHCO₃ (100 mL) and stir until gas evolution ceases. Separate layers, then extract the aqueous layer with CH₂Cl₂ (100 mL). Pool the organic layers, dry over Na₂SO₄, filter and evaporate to a pale yellow oil. Take up in DMSO (25 mL), add solid NaCN (1.25 g, 49.011 g/mol) and heat to 60° C. while stirring under N₂. Stir 2 hours until chloride consumed (TLC; chloride Rf=1.0, nitrile Rf=0.6; using 20% EtOAc/80% hexanes as eluent), then cool to rt. Add 2.0 N NaOH (150 mL) and stir until orange precipitate forms, then filter and wash solid with H₂O. Dissolve solid in CH₂Cl₂, wash with H₂O, the dry over Na₂SO₄. Filter the organic layer and evaporate to an orange oil which crystallizes upon standing at rt. (2.3 g). LCMS= 180.2 (MH⁺), 178.2 (M⁻).

E. 2-(4-Chloro-2,6-dimethylphenyl)-3-oxobutanenitrile

Dissolve 4-chloro-2,6-dimethyl phenyl acetonitrile (2.3 g, 179.2 g/mol) in 15 mL EtOAc and add sodium metal (0.35 g, pea-sized fragments). Heat to reflux (90° C. bath temperature) under N₂ overnight. Evaporate down to solid and slurry up in Et₂O (100 mL); stir vigorously to break up fragments. Filter and wash solid with copious amounts of Et₂O. Dissolve solid in H₂O to form a clear yellow solution, and add 1.0 N HCl (100 mL) to pH 1. Extract the resulting cloudy solution with CH₂Cl₂ (3×100 mL) until aqueous layer is clear. Pool and dry the organic layers over Na₂SO₄, filter and evaporate to yellow oil (1.8 g). TLC: Rf=0.2 using 20% EtOAc/80% hexanes as eluent. LCMS=222.3 (MH⁺); 220.2 (M⁻)

F. 5-Amino-4-(4-chloro-2,6-dimethylphenyl)-3-methylpyrazole

Dissolve anhydrous hydrazine (0.91 g, 0.90 mL) in 20 mL toluene. Add glacial acetic acid (2.25 mL) and allow to stand at ambient temperature for 10 minutes until solution becomes cloudy white. Add a solution of 2-(4-chloro-2,6-dimethylphenyl)-3-oxobutanenitrile in 10 mL toluene, rinsing out the ketonitrile flask with an additional 5 mL toluene. Heat to reflux under N₂ (130° C.) with Dean-Stark trap attached. Water will begin to accumulate after 10 minutes or so. After 2 hours, evaporate down and partition between 1.0 N NaOH (100 mL) and EtOAc (100 mL). Extract aqueous layer with EtOAc (2×100 mL), then pool the organic layers and dry over Na₂SO₄. Filter and evaporate to yellow oil (1.75 g). Use without further purification. LCMS=236.5 (M⁺); 234.5 (M⁻)

G. 7-Hydroxy-2,5-dimethyl-3-(4-chloro-2,6-dimethylphenyl)-pyrazolo[1,5-a]pyrimidine

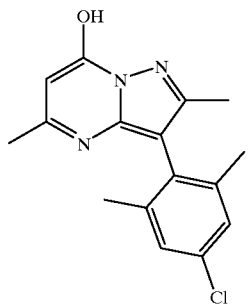

Dissolve 5-amino-4-(4-chloro-2,6-dimethylphenyl)-3-methylpyrazole in 20 mL glacial acetic acid at ambient temperature, and add ethyl acetoacetate (2.0 mL, 1.99 g). Heat to reflux (130° C.) under N₂ overnight. Evaporate down to concentrate and add 200 mL Et2O to precipitate out product. Stir at ambient temperature for 1 hour, then filter and wash the resulting white solid (1.25 g) with copious amounts of Et₂O. LCMS=302.2 (MH⁺); 300.2 (M⁻).

H. 7-Chloro-2,5-dimethyl-3-(4-chloro-2,6-dimethylphenyl)-pyrazolo[1,5-a]pyrimidine

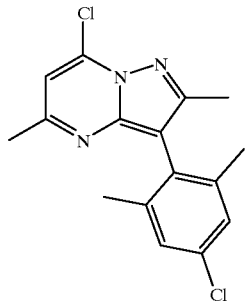

Slurry 7-hydroxy-2,5-dimethyl-3-(4-chloro-2,6-dimethylphenyl)-pyrazolo[1,5-a] pyrimidine in 10 mL POCl₃ and reflux at 130° C. under N₂. After 2 hours, monitoring by TLC (alcohol Rf=0.5, chloride Rf=1.0; EtOAc as eluent), quench the reaction carefully at ambient temperature by diluting with 50 mL CH₂Cl₂ and pouring slowly into non-stirring saturated NaHCO₃. Adjust stirring speed to control rate of quenching of residual POCl₃ and stir until gas evolution ceases. Separate the layers and extract the aqueous layer with CH₂Cl₂ (2×50 mL). Pool the organic layers and dry over Na₂SO₄. Filter and evaporate to yellow oil, which is used directly without further purification.

I. 7-(2-ainoethylamino)-2,5-dimethyl-3-(4-chloro-2,6-dimethylphenyl)-pyrazolo[1,5-a] pyrimidine

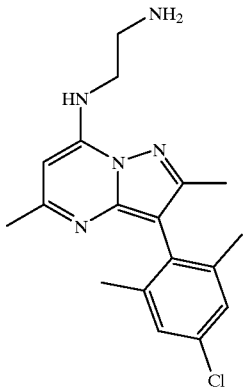

Dissolve 7-chloro-2,5-dimethyl-3-(4-chloro-2,6-dimethylphenyl)-pyrazolo[1,5-a] pyrimidine in 25 mL CH₃CN, then add excess ethylenediamine (5 mL) and heat to 80° C. for 3–6 hours under N₂ with attached reflux condenser. (TLC; product diamine Rf=0.5, aryl chloride Rf=1.0; [10% (2.0M NH₃ in MeOH)/90% CH₂Cl₂] as eluent). Cool to ambient temperature and evaporate to yellow oil. Partition between CH₂Cl₂ (50 mL) and 1.0 N NaOH (50 mL), and extract aqueous layer 2×30 mL CH₂Cl₂. Pool organic layers, dry over Na₂SO₄, filter and evaporate to yellow-white foam (1.25 g). Use without further purification. LCMS=344.4 (MH⁺); 342.3 (M⁻).

J. 7-(2-(perhydro-2H-pyran-4-ylamino)ethylamino)-2,5-dimethyl-3-(4-chloro-2,6-dimethylphenyl)-pyrazolo[1,5-a] pyrimidine

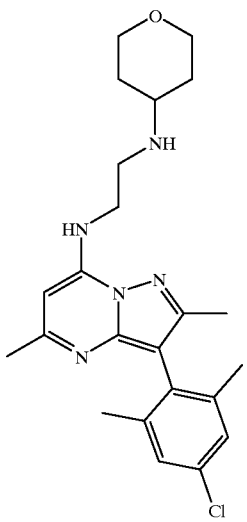

Dissolve 7-(2-aminoethylamino)-2,5-dimethyl-3-(4-chloro-2,6-dimethylphenyl)-pyrazolo [1,5-a] pyrimidine (0.183 g, 5.4×10⁻⁴ mol, 339.2 g/mol) in dichloroethane (5 mL) and add tetrahydro-4H-pyran-4-one (0.068 g, 0.060 mL, 100.12 g/mol) and sodium triacetoxyborohydride (0.172 g, 211.94 g/mol). To the resultant slurry, add glacial acetic acid (0.032 mL, 5.4×10⁻⁴ mol) and stir at ambient temperature under N₂ for 3 hours. Partition between CH₂Cl₂ (3 mL) and 1.0 N NaOH (10 mL), then separate the layers and chromatograph the CH₂Cl₂ layer using [10% (2.0M NH₃ in MeOH)/90% CH₂Cl₂] as eluent. Obtained 0.16 g white solid-foam upon evaporation. TLC: Rf=0.65. LCMS= 422.5 (MH⁺); 420.5 (M⁻). ¹H-NMR (CDCl₃): 6.67 (s, 2H); 5.79 (d, 1H, J=8.8 Hz); 3.98 (br. d, 2H, J=12 Hz); 3.78 (s, 3H); 3.52 (t, 2H, J=6 Hz); 3.39 (br. t, 2H, J=12 Hz); 3.37 (s, 1H); 3.04 (t, 2H, J=6 Hz); 2.75–2.81 (m, 2H); 2.40 (s, 3H); 2.18 (s, 3H); 2.00 (s, 6H); 1.89 (br. d, 2H, J=12 Hz); 1.47–1.53 (m, 2H).

Example 2

Preparation of 7-(2-(2-(4-ethoxy-3-methoxyphenyl)ethylamino)ethylamino)-3-(2,4-dimethoxyphenyl)-2,5-dimethyl-pyrazolo[1,5-a]pyrimidine (formula I where X is CH, R¹ is CH₃, R² is H, A is CH₂, B is CH₂, R³ is CH₃, R⁴ is 2,4-dimethoxyphenyl, R⁵ is 2-(4-ethoxy-3-methoxyphenyl)ethylamino)ethyl).

A. (3E)-3-(2,4-dimethoxyphenyl)-4-(dimethylamino)but-3-en-2-one

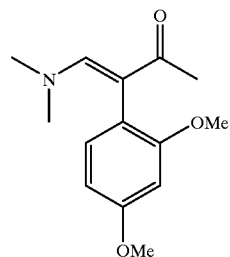

Dissolve 1-(2,4-dimethoxyphenyl)acetone (1.0 g, 5.15 mmol, 194.23 g/mol) in DMF-diethyl acetal (4.5 mL, 25.7 mmol, 147.22 g/mol) and stir under N₂ at 100° C. overnight. TLC using 20% EtOAc/80% hexanes; (ketone Rf=0.25, product Rf=0.0). Evaporate to thick oil, dissolve in EtOAc (25 mL) and wash with H₂O (3×25 mL). Extract pooled H₂O layers with EtOAc. Dry pooled organic layers over Na₂SO₄, filter and evaporate to thick oil which solidifies upon standing at ambient temperature (0.98 g). Use without further purification. LCMS=250.2 (MH⁺); 248.2 (M⁻).

B. 4-(2,4-Dimethoxyphenyl)-5-methyl-isoxazole

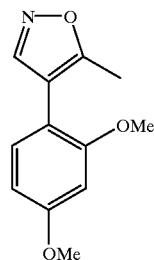

Dissolve (3E)-3-(2,4-dimethoxyphenyl)-4-(dimethylamino)but-3-en-2-one (5.1 g, 20.6 mmol) in EtOH (50 mL) and add NH₂OH.HCl (3.05 g, 44.0 mmol). Heat to reflux under N₂ for 20 minutes. Cool and evaporate to red-brown oil. Dissolve in CH₂Cl₂, dry over Na₂SO₄, filter and concentrate to red-brown oil (4.4 g). Use without further purification. LCMS=220.2 (MH⁺); 218.2 (M⁻).

C. 2-(2,4-Dimethoxyphenyl)-3-oxobutanenitrile.

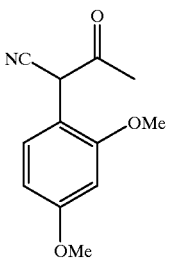

Slurry 4-(2,4-dimethoxyphenyl)-5-methyl-isoxazole (4.4 g) in 1.0 N NaOH (35 ML) and add 35 mL MeOH to dissolve. Heat at 60° C. under $N_2$ for 1 hour, then cool to clear brown solution. Add 1.0 N HCl to acidify to pH 1, then filter the resulting white solid precipitate. Dissolve solid in EtOAc, dry over $Na_2SO_4$, filter and concentrate to red oil. Use without further purification. LCMS=220.2 (MH+); 218.2 (M−).

D. N-(4-Ethoxy-3-methoxy-phenethyl)-ethylenediamine.

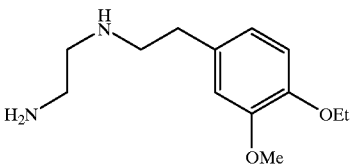

Dissolve 4-ethoxy-3-methoxy-phenyl acetic acid (26 g, 119 mol) in dichloroethane (300 mL, anhydrous) and cool to 0° C. Dropwise add oxalyl chloride (130 mL, 2.0 M in $CH_2Cl_2$) and DNM (2 mL), then allow to warm to ambient temperature overnight. Evaporate down and chase with $CH_2Cl_2$, then evaporate to a tan oil. Dissolve in 200 mL dichloroethane and cool to 0° C. while stirring under $N_2$. Dropwise, over 45 minutes, add a second solution of N-tBOC-ethylenediamine (20 g) and triethylamine (20 mL) in 100 mL dichloroethane. Partition between $CH_2Cl_2$ (500 mL) and 1.0 N HCl (200 mL), then separate the layers and wash the organic layer with 1.0 N HCl (200 mL). Wash the organic layer with saturated $K_2CO_3$ (2×200 mL), then dry the $CH_2Cl_2$ layer over $Na_2SO_4$, filter and evaporate to tan solid. Triturate with 200 mL $Et_2O$ and stir vigorously to fragment solid, then filter and wash copiously with $Et_2O$ to obtain 20.5 g white solid. Dissolve white solid (3.0 g, 8.52 mmol) in 10 mL (1:1 trifluoroacetic acid: $CH_2Cl_2$) and stir at ambient temperature 1 hour. Evaporate down and partition between $CH_2Cl_2$ (25 mL) and 1.0 N NaOH (25 mL), then separate the layers and extract the aqueous layer with $CH_2Cl_2$ (25 mL). Pool the organic layers, dry over $Na_2SO_4$, filter and evaporate to a white solid (1.75 g).

E. 7-(2-(2-(4-ethoxy-3-methoxyphenyl)ethylamino)ethylamino)-3-(2,4-dimethoxyphenyl)-2,5-dimethyl-pyrazolo[1,5-a]pyrimidine.

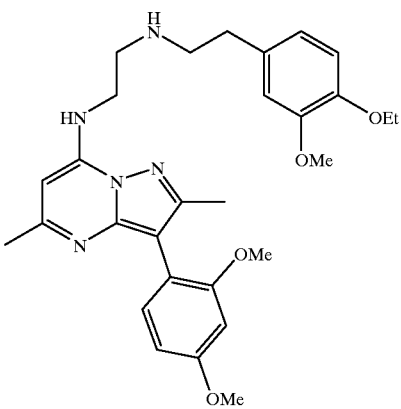

Dissolve 7-chloro-2,5-dimethyl-3-(2,4-dimethoxyphenyl)-pyrazolo[1,5-a]pyrimidine (prepared from 2-(2,4-dimethoxyphenyl)-3-oxobutanenitrile according to the methods of EXAMPLE 1 F, G and H) (0.2 g, 6.31×10⁻⁴ mol) in dichloroethane (10 mL), then add the N-(4-ethoxy-3-methoxy-phenethyl)-ethylenediamine from step D (0.10 g, 4.2×10⁻⁴ mol) and diisopropylethylamine (0.1 mL, 6×10⁻⁴ mol) and stir under $N_2$ at 80° C. overnight. Wash the organic layer with saturated $NaHCO_3$ (10 mL), then evaporate the organic layer down to a yellow oil. Chromatograph using [10% (2.0 M $NH_3$ in MeOH)/90% $CH_2Cl_2$] and evaporate to obtain 50 mg pale yellow solid. LCMS=520.3 (MH+); 518.3 (M−). ¹H-NMR ($CDCl_3$): 7.35 (d, 1H, J=8.4 Hz); 6.71–6.8 (m, 3H); 6.56–6.61 (m, 2H); 6.47 (t, 1H, J=5.6 Hz); 5.75 (s, 1H); 4.05 (quart., 2H, J=6.8 Hz); 3.82–3.88 (m, 5H); 3.77 (s, 3H); 3.42 (quart., 2H, J=5.6 Hz); 2.97 (t, 2H, J=6 Hz); 2.90 (t, 2H, J=6 Hz); 2.76 (t, 2H, J=7.2 Hz); 2.44 (s, 3H); 2.35 (s , 3H)1.43 (t, 3H) 1.43 (t, 3H, J=6.8 Hz).

Example 3

Preparation of 7-(2-(perhydro-2H-pyran-4-ylamino) ethylamino)-2,5-dimethyl-3-(2,6-dimethyl-4-methoxyphenyl)-pyrazolo[1,5-a] pyrimidine (formula I where X is CH, $R^1$ is $CH_3$, $R^2$ is H, A is $CH_2$, B is $CH_2$, $R^3$ is $CH_3$, $R^4$ is 2,4-dimethyl-4-methoxyphenyl, $R^5$ is perhydro-2H-pyran-4-yl)

A. 4-Methoxy-2,6-dimethyl phenyl acetonitrile

Dropwise add a solution of chlorotrimethylsilane (20 mL) in $CH_2Cl_2$ (40 mL) to a stirred solution cooled to 0° C. of 4-methoxy-2,6-dimethyl benzyl alcohol (approx. 74 mmol) in 300 mL $CH_2Ck_2$. Solution changes color from colorless to yellow and then to purple over the course of the reaction. After 2 hours, monitoring by TLC (alcohol Rf=0.25, chloride Rf=0.95; using 20% EtOAc/80% hexanes as eluent), evaporate down to a yellow oil. Dissolve in dry DMF (50 mL) and cool to 0° C. under $N_2$. Add freshly ground NaCN (7.0 g) portionwise over 5 minute (exothermic) to the stirring reaction, forming a yellow/white slurry. Stir for 5–8 hours at 0° C. until no starting material remains, as determined by TLC (nitrile Rf=0.5; using 20% EtOAc/80% hexanes as eluent). Partition the reaction solution between EtOAc (100 mL) and 0.1 N NaOH (300 mL). Dry the EtOAc layer over Na2SO4, filter and evaporate to yellow oil. Chromatograph in 10% EtOAC/90% hexanes on silica to remove residual chloride and evaporate to 2.1 g yellow solid; clean by TLC. LCMS=176.5 (MH+), 174.4 (M−).

B. 7-(2-(Perhydro-2H-pyran-4-ylamino)ethylamino)-2,5-dimethyl-3-(2,6-dimethyl-4-methoxyphenyl)-pyrazolo[1,5-a] pyrimidine

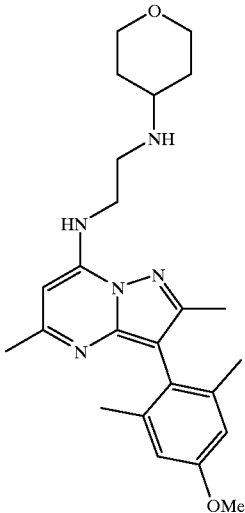

7-(2-(Perhydro-2H-pyran-4-ylamino)ethylamino)-2,5-dimethyl-3-(2,6-dimethyl-4-methoxyphenyl)-pyrazolo[1,5-a] pyrimidine is obtained from 4-methoxy-2,6-dimethyl phenyl acetonitrile using the procedures described in EXAMPLE 1 E, F, G, H, I, J.

Example 4

Preparation of 7-(2-(perhydro-2H-pyran-4-ylamino)ethylamino)-2-trifluoromethyl-5-methyl-3-(2,4-dichlorophenyl)-pyrazolo[1,5-a] pyrimidine (formula I where X is CH, $R^1$ is $CH_3$, $R^2$ is H, A is $CH_2$, B is $CH_2$, $R^3$ is $CF_3$, $R^4$ is 2,4-dichlorophenyl, $R^5$ is perhydro-2H-pyran-4-yl)

A. 2-(2,4-Dichlorophenyl)-4,4,4-trifluoro-3-oxobutanenitrile

Slurry 2,4-dichlorophenylacetonitrile (I) (5.0 g, 26.9 mmol, 186.04 g/mol) in ethyl trifluoroacetate (6.4 mL, 7.6 g, 142.08 g/mol) and add 20 mL anhydrous THF. Portionwise at ambient temperature add NaH (1.88 g, 47.1 mmol, 60% in mineral oil) over 5 minutes. Heat reaction to reflux (90° C. bath temperature) overnight. Evaporate to thick red-brown oil and partition between $Et_2O$ (100 mL) and $H_2O$ (60 mL). Separate layers and extract $H_2O$ with $Et_2O$ (2×75 mL). Acidify the aqueous layer with 1.0 N HCl to pH 1 (becomes cloudy white suspension) and extract aqueous layer with $CH_2Cl_2$ (3×100 mL). Dry pooled $CH_2Cl_2$ layers over $Na_2SO_4$, filter and concentrate to yellow oil (7.5 g, 26.5 mmol). Use without further purification. LCMS=281.9 ($MH^+$); 279.8 ($M^-$)

B. 7-(2-(Perhydro-2H-pyran-4-ylamino)ethylamino)-2-trifluoromethyl-5-methyl-3-(2,4-dichlorophenyl)-pyrazolo[1,5-a] pyrimidine

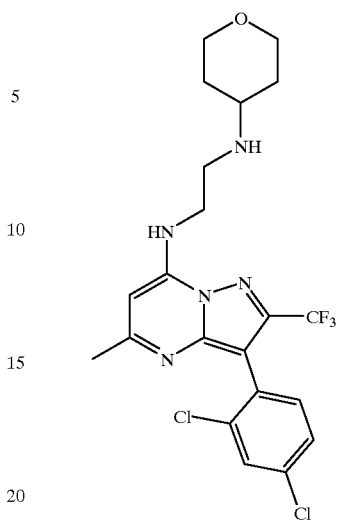

7-(2-(Perhydro-2H-pyran-4-ylanino)ethylamino)-2-trifluoromethyl-5-methyl-3-(2,4-dichlorophenyl)-pyrazolo[1,5-a] pyrimidine is obtained from 2-(2,4-dichlorophenyl)-4,4,4-trifluoro-3-oxobutanenitrile using the procedures described in EXAMPLE 1 F, G, H, I, J.

Example 5

Preparation of 7-(2-(2-(4-methoxyphenyl)ethylamino)ethylamino)-3-(2,4,6-trimethylphenyl)-2,5-dimethyl-pyrazolo[1,5-a]pyrimidine (formula I where X is CH, $R^1$ is $CH_3$, $R^2$ is H, A is $CH_2$, B is $CH_2$, $R^3$ is $CH_3$, $R^4$ is 2,4,6-trimethylphenyl, $R^5$ is 2-(4-methoxyphenyl)ethylamino)ethyl).

A. N-(3-(2,4,6-trimethylphenyl)-2,5-dimethyl-pyrazolo[1,5-a]pyrimidin-7yl)-2-(4-methoxyphenyl)acetamide

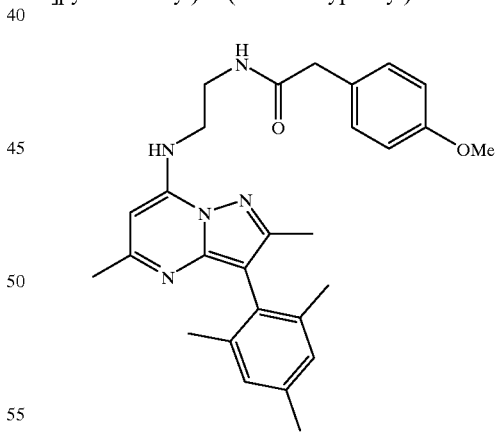

Dissolve 7-chloro-2,5-dimethyl-3-(2,4,6-trimethylphenyl)-pyrazolo[1,5-a]pyrimidine (0.26 g, 8.69× $10^{-4}$ mol) in 2 mL N-methylpyrrolidine, and add N-(2-aminoethyl)-2-(4-methoxyphenyl)acetamide (0.75 g, 3.6 mmol). Heat to 80° C. overnight under $N_2$. Partition between EtOAc (50 mL) and $H_2O$ (50 mL), then separate layers and wash EtOAC layer successively with 0.1 N NaOH (25 mL), $H_2O$ (25 mL), and brine. Pool aqueous layers and extract with EtOAc (25 mL). Pool EtOAc layers, dry over $Na_2SO_4$, filter and concentrate to yellow oil. Chromatograph on silica gel eluting with EtOAc and evaporate to obtain 0.30 g of N-(3-(2,4,6-trimethylphenyl)-2,5-dirnethyl-pyrazolo[1,5-a]pyrimidin-7yl)-2-(4-methoxyphenyl)acetamide as a clear pale yellow oil. LCMS=472.3 (MH$^+$); 470.2 (M$^-$). $^1$H-NMR (CDCl$_3$): 7.10 (d, 2H, J=10.2 Hz); 6.39 (s, 2H); 6.81 (d, 2H, J=10.2 Hz); 6.46 (t, 1H, J=6.0 Hz); 6.16 (t, 1H, J=6.0 Hz); 5.79 (s, 1H); 3.76 (s, 3H); 3.45–3.50 (m, 6H); 2.38 (s, 3H); 2.30 (s, 3H); 2.20 (s, 3H); 2.02 (s, 6H).

B. 7-(2-(2-(4-methoxyphenyl)ethylamino)ethylamino)-3-(2,4,6-trimethylphenyl)-2,5-dimethyl-pyrazolo [1,5-a] pyrimidine

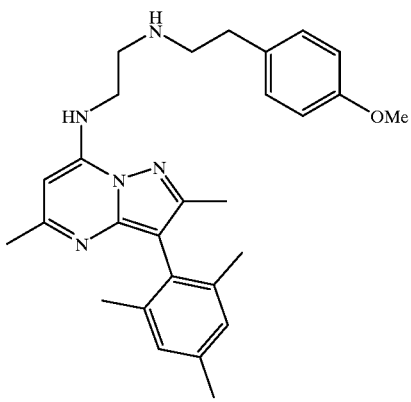

Dissolve N-(3-(2,4,6-trimethylphenyl)-2,5-dimethyl-pyrazolo[1,5-a]pyrimidin-7-yl)-2-(4-methoxyphenyl)acetamide (0.15 g, 3.2×10$^{-4}$ mol) in 5 mL anhydrous THF and stir under N$_2$. Add borane-dimethylsulfide complex (0.25 mL, 10.0 M in THF) and heat to reflux overnight. Quench by careful addition of MeOH until gas evolution ceases, then evaporate to oil. Add HCl in Et$_2$O (2 mL, 1.0 M) and MeOH to solubilize (5 mL), then reflux 1 hour and evaporate. Dissolve in CH$_2$Cl$_2$ (20 mL) and wash with saturated NaHCO$_3$ (20 mL). Evaporate CH$_2$Cl$_2$ layer and chromatograph on silica gel eluting with EtOAc (Rf=0.15), then evaporate down to a clear oil (0.10 g). LCMS 458.3 (MH$^+$), 456.4 (M$^-$). $^1$H-NMR (CD$_3$Cl): 7.13 (d, 2H, J=8.8 Hz); 6.94 (s, 3H); 6.84 (d, 2H,J=8.8 Hz); 6.57 (t, 1H, J=5.6 Hz); 5.77 (s, 1H); 3.78 (s, 3H); 3.44 (quartet, 2HJ=5.6 Hz); 3.00 (t, 2H, J=6.0 Hz); 2.92 (t, 2H, J 6.8 Hz); 2.78 (t, 2H, J=6.8 Hz); 2.41 (s, 3H); 2.31 (s, 3H); 2.22 (s, 3H); 2.01 (s, 6H).

Alternatively, the reduction can be carried out as follows: dissolve N-(3-(2,4,6-trimethylphenyl)-2,5-dimethyl-pyrazolo[1,5-a]pyrimidin-7-yl)-2-(4-methoxyphenyl)acetamide (0.15 g, 3.2×10$^{-4}$ mol) in 5 mL anhydrous THF. Add a fresh solution of alane.dimethylethylamine complex in toluene (2.25 mL, 9.6×10$^{-4}$ mol) and heat to 50° C. overnight under dry N$_2$. Quench reaction by addition of solid Na$_2$CO$_3$.10H$_2$O (0.5 g) and stir vigorously until gas evolution ceases. Filter through celite to remove solid and evaporate the filtrate down to a clear pale yellow oil. Chromatograph on silica gel eluting with EtOAc (Rf=0.15), then evaporate down to a clear oil (0.10 g).

Example 6

Preparation of 7-(2-(2-(4-ethoxy-3-methoxyphenyl)ethylamino)ethylamino)-3-(2,4,6-trimethylphenyl)-2,5-dimethyl-pyrazolo[1,5-a]pyrimidine (formula I where X is CH, R$^1$ is CH$_3$, R$^2$ is H, A is CH$_2$, B is CH$_2$, R$^3$ is CH$_3$, R$^4$ is 2,4,6-trimethylphenyl, R$^5$ is 2-(4-ethoxy-3-methoxyphenyl)ethylamino)ethyl).

A. N-(3-(2,4,6-trimethylphenyl)-2,5-dimethyl-pyrazolo[1,5-a]pyrimidin-7-yl)-2-(4-ethoxy-3-methoxyphenyl)acetamide

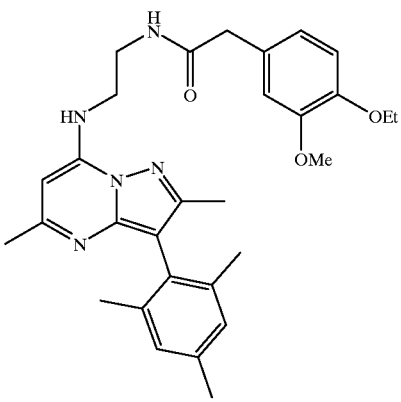

Dissolve 7-(2-aminoethylamino)-2,5-dimethyl-3-(2,4,6-trimethylphenyl)-pyrazolo[1,5-a] pyrimidine (91 mg, 2.8×10$^{-4}$ mol) in N-methyl pyrrolidine (2 mL) and add 2-(4-ethoxy-3-methoxyphenyl)acetic acid (65 mg, 3.1×10$^{-4}$ mol). Add triethylamine (85 mg, 0.117 mL, 8.46×10$^{-4}$ mol) and BOP-Cl (0.15 g, 3.4×10$^{-4}$ mol), then stir at ambient temperature under N$_2$ overnight. Partition between H$_2$O (10 mL) and EtOAc (10 mL), then separate layers and wash EtOAc layer with 1.0 N NaOH (10 mL). Dry the EtOAc layer over Na$_2$SO$_4$, filter and evaporate to oil. Use without further purification. LCMS=516.3 (MH$^+$); 514.2 (M$^-$).

Alternatively, N-(2-aminoethyl)-2-(4-ethoxy-3-methoxyphenyl)acetamide can be prepared as follows: dissolve 2-(4-ethoxy-3-methoxyphenyl)acetic acid in (26 g, 119 mol) in dichloroethane (300 mL, anhydrous) and cool to 0° C. Dropwise add oxalyl chloride (130 mL, 2.0 M in CH$_2$Cl$_2$) and DMF (2 mL), then allow to warm to ambient temperature overnight. Evaporate down and chase with CH$_2$Cl$_2$, then evaporate to a tan solid. Dissolve a portion of the tan solid acid chloride (80 mg, 3.5×10$^{-4}$ mol) in N-methyl pyrrolidine (2 mL) and cool to 0° C. Add 7-(2-aminoethylamino)-2,5-dimethyl-3-(2,4,6-trimethylphenyl)-pyrazolo[1,5-a] pyrimidine (100 mg, 3.1×10$^{-4}$ mol) and triethylamine (85 mg, 0.117 mL, 8.46×10$^{-4}$ mol), then stir at ambient temperature under N$_2$ overnight. Partition between H$_2$O (10 mL) and EtOAc (10 mL), then separate layers and wash EtOAc layer with 1.0 N NaOH (10 mL). Dry the EtOAc layer over Na$_2$SO$_4$, filter and evaporate to oil. Use without further purification.

B 7-(2-(2-(4-Ethoxy-3-methoxyphenyl)ethylamino)ethylamino)-3-(2,4,6-trimethylphenyl)-2,5-dimethyl-pyrazolo[1,5-a]pyrimidine.

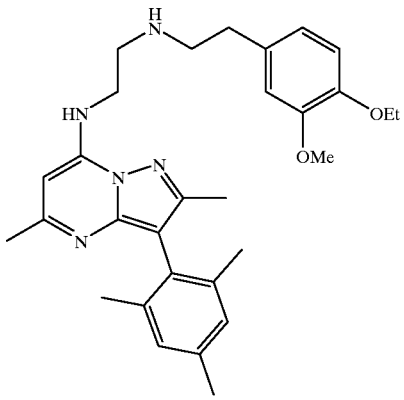

Reduction of N-(3-(2,4,6-trimethylphenyl)-2,5-dimethyl-pyrazolo[1,5-a]pyrimidin-7-yl)-2-(4-ethoxy-3-methoxyphenyl)acetamide with borane-dimethylsulfide complex, according, to the procedure of EXAMPLE 5, yields 7-(2-(2-(4-ethoxy-3-methoxyphenyl)ethylamino)ethylamnino)-3-(2,4,6-trimethylphenyl)-2,5-dimethyl-pyrazolo[1,5-a]pyrimidine. LCMS=502.3 (MH$^+$); 500.4 (M$^-$).

Example 7

Preparation of 7-(2-(perhydro-2H-pyran-4-ylamino) ethylamino)-2,5-dimethyl-3-(4-methoxy-2,6-dimethylphenyl)-[1,5-a]-pyrazolo-1,3,5-triazine.

(formula I where X is N, R$^1$ is CH$_3$, R$^2$ is H, A is CH$_2$, B is CH$_2$, R$^3$ is CH$_3$, R$^4$ is 2,6-dimethyl-4-methoxyphenyl, R$^5$ is perhydro-2H-pyran-4-yl)

A. (Iminoethyl)[4-(4-methoxy-2,6-dimethylphenyl)-3-methylpyrazol–5-yl]amine acetate salt.

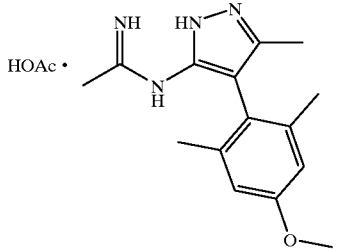

To a solution of 5-amino-4-(4-methoxy-2,6-dimethylpyrazole (1.89 g) (prepared from 4-methoxy-2,6-dimethyl benzaldehyde according to Example 1 C-F) in acetonitrile (30 mL) add ethylacetimidate (free base, 1.8 mL) followed by acetic acid (0.47 mL). Collect the precipitate that formed upon stirring overnight by filtration. Wash the solid with dry ether and dry to afford 2.61 g of (iminoethyl)[4-(4-methoxy-2,6-dimethylphenyl)-3-methylpyrazol–5-yl]amine acetate salt as a white powder.

B. 2,6-Dimethyl-7-(2,6-dimethyl-4-methoxyphenyl)-3H-[1,5-c]-pyrazolo-1,3,5-triazin-4-one.

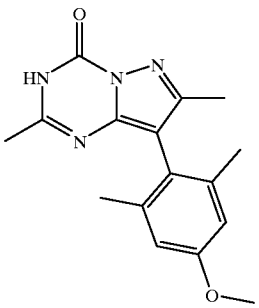

Add sodium pieces (1.81 g) to a flask containing anhydrous ethanol and equipped with a reflux condenser. Allow the mixture to stir until all the sodium is consumed and then add the amidine (2.61 g as the acetate salt) from step A in one portion. Add diethyl carbonate (7.6 mL) and reflux the mixture overnight. Concentrate the mixture under reduced pressure, dissolve the residue in water (75 mL) and adjust the pH to 5 with 3N HCl. Extract the aqueous mixture with ethyl acetate and wash the extracts with brine, dry over anhydrous sodium sulfate, and concentrate in vacuo to obtain a foam. Stir the residue with hexanes for 20 minutes and collect the solid by filtration, then wash with hexanes to obtain 2.01 g of 2,6-dimethyl-7-(2,6-dimethyl-4-methoxyphenyl)-3H-[1,5-c]-pyrazolo-1,3,5-triazin-4-one as a yellow powder: MS 299 (M+H).

C. 4–Chloro-2,6-dimethyl-7-(2,6-dimethyl-4-methoxyphenyl) [1,5-a]-pyrazolo-1,3,5-triazine.

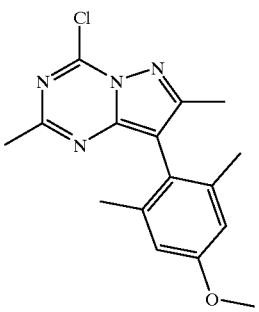

Dissolve 2,6-dimethyl-7-(2,6-dimethyl-4-methoxyphenyl)-3H-[1,5-c]-pyrazolo-1,3,5-triazin-4-one from step B (1 g) in POCl$_3$ (50 mL) and add N,N-dimethylaniline (0.55 mL). Reflux the reaction mixture under a dry nitrogen atmosphere for 18 h at which time concentrate the mixture under reduced pressure. Dissolve the residue in ethyl acetate and wash with a saturated aqueous NaHCO$_3$ solution, then with brine. Dry the organic layer over anhydrous sodium sulfate, filter and concentrate under reduced pressure to obtain 4-chloro-2,6-dimethyl-7-(2,6-dimethyl-4-methoxyphenyl) [1,5-a]-pyrazolo-1,3,5-triazine as a dark oil. MS 317 (M+H).

D. 2,6-Dimethyl-7-(2,6-dimethyl-4-methoxyphenyl)-4-(2-aminoethyl)amino-[1,5-a]-pyrazolo-1,3,5-triazine.

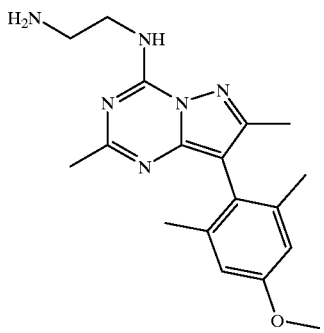

Dissolve 4-chloro-2,6-dimethyl-7-(2,6-dimethyl-4-methoxyphenyl) [1,5-a]-pyrazolo-1,3,5-triazine in dry toluene (10 mL) to form a stock solution of the chloride (~0.34 M). Add a portion of this solution (8 mL) dropwise into a stirring solution of ethylenediamine (3.6 mL) in acetonitrile (50 mL) which is heated to 60° C. After 3 h at 60° C., cool the solution, concentrate under reduced pressure, dilute with 10% NaOH and extract with ethyl acetate. Wash the combined extracts with brine, dry over anhydrous sodium sulfate and concentrate under reduced pressure to obtain a yellow residue. Triturate the residue with 20% ethyl acetate/hexanes and collect the resulting solid by filtration to obtain 0.72 g of 2,6-dimethyl-7-(2,6-dimethyl-4-metboxyphenyl)-4-(2-aminoethyl)amino-[1,5-a]-pyrazolo-1,3,5-triazine as a yellow solid: MS 341 (M+H).

E. 2,6-Dimethyl-7-(2,6-dimethyl-4-methoxyphenyl)-4-(2-(perhydro-2H-pyran-4-ylamino)ethylamino)-[1,5-a]-pyrazolo-1,3,5-triazine.

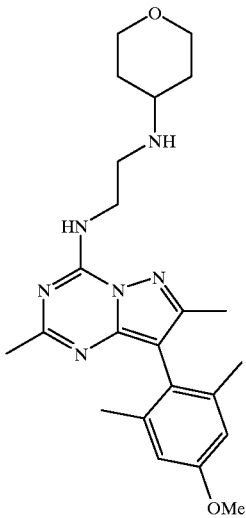

Dissolve 2,6-dimnethyl-7(2,6-dimethyl-4-methoxyphenyl)-4-(2-aminoethyl)amino-[1,5-a]-pyrazolo-1,3,5-triazine from step D (0.211 g) in dry dichloroethane (15 mL) and add tetrahydro-4-H-pyran-4-one (57 μL). Add acetic acid (35 μL) followed by sodium triacetoxyborohydride (0.184 g) and stir the resulting homogeneous mixture overnight at ambient temperature. Dilute the reaction mixture with 4 volumes of dichlorornethane, wash with brine, dry over anhydrous sodium sulfate, and concentrate under reduced pressure to obtain a yellow solid. Purify using preparative thin-layer chromatography [10% MeOH(2N NH$_3$)/CH$_2$Cl$_2$] to obtain 2,6-dimethyl-7-(2,6-dimethyl-4-methoxyphenyl)-4-(2-(perhydro-2H-pyran-4-ylamino)ethylamino)-[1,5-a]-pyrazolo-1,3,5-triazine (0.165 g) as a light-yellow solid: MS 425 (M+H).

Example 8

Preparation of 2-[(2-{[7-(2,6-dichloro-4-ethoxyphenyl)-2,6-dimethylpyrazolo [1,5-a] 1,3,5-triazin-4-yl]amino} ethyl)amino]-2-methylpropan-1-ol.

formula I where X is N, $R^1$ is CH$_3$, $R^2$ is H, A is CH$_2$, B is CH$_2$, $R^3$ is CH$_3$, $R^4$ is 2,6-dichloro-4-ethoxyphenyl, $R^5$ is C(CH$_3$)$_2$CH$_2$OH.

A. Iminoethyl[4-(4-ethoxy-2,6-dichlorophenyl)-3-methylpyrazol–5-yl]amine acetate salt.

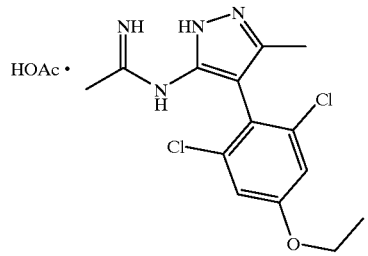

To a solution of 5-amino-4-(4-ethoxy-2,6-dichlorophenyl)-3-methylpyrazole (4.8 g) (prepared from 4-ethoxy-2,6-dichloro benzaldehyde according to Example 1 C-F) in acetonitrile (50 mL) add ethylacetimidate (free base, 2.3 mL) followed by acetic acid (0.96 mL). Collect the precipitate that formed upon stirring overnight by filtration. Wash the solid with dry ether and dry to afford 5.02 g of (iminoethyl)[4-(4-ethoxy-2,6-dichlorophenyl)-3-methylpyrazol–5-yl]amine acetate salt as a white powder.

B. 2,6-Dimethyl-7-(2,6-dichloro-4-ethoxyphenyl)-3H-[1,5-c]-pyrazolo-1,3,5-triazin-4-one.

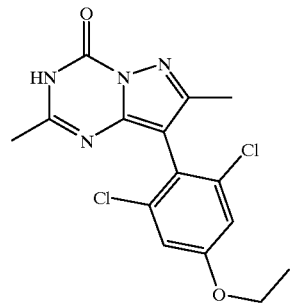

Add sodium pieces (2.98 g) to a flask containing anhydrous ethanol and equipped with a reflux condenser. Allow the mixture to stir until all the sodium is consumed and then add the amidine (5.02 g as the acetate salt) from step A in one portion. Add diethyl carbonate (12.6 mL) and reflux the mixture for four hours. Concentrate the mixture under reduced pressure, dissolve the residue in water (75 mL) and adjust the pH to 5 with 3N HCl. Extract the aqueous mixture with ethyl acetate and wash the extracts with brine, dry over anhydrous sodium sulfate, and concentrate in vacuo to obtain a foam. Stir the residue with hexanes for 20 minutes and collect the solid by filtration, then wash with hexanes to obtain 4.41 g of 2,6-dimethyl-7-(2,6-dichloro-4-ethoxyphenyl)-3H-[1,5-c]-pyrazolo-1,3,5-triazin-4-one as a beige solid: MS 353 (M+H).

C. 4–Chloro-2,6-dimethyl-7-(2,6-dichloro-4-ethoxyphenyl)[1,5-a]-pyrazolo-1,3,5-triazine.

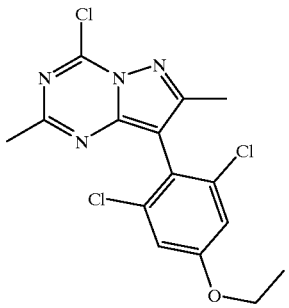

Dissolve 2,6-dimethyl-7-(2,6-dichloro-4-ethoxyphenyl)-3H-[1,5-c]-pyrazolo-1,3,5-triazin-4-one from step B (1.05 g) in POCl₃ (50 mL) and add 2,6-lutidine (0.45 mL). Reflux the reaction mixture under a dry nitrogen atmosphere for 48 h and then concentrate the mixture under reduced pressure. Dissolve the residue in ethyl acetate and wash with a saturated aqueous NaHCO₃ solution, then with brine. Dry the organic layer over anhydrous sodium sulfate, filter and concentrate under reduced pressure to obtain an oil which crystallizes upon standing. Wash the solid with hexanes to remove residual 2,6-lutidine and collect the solid on a sintered glass funnel yielding 4-chloro-2,6-dimethyl-7-(2,6-dichloro-4-ethoxyphenyl) [1,5-a]-pyrazolo-1,3,5-triazine. MS 372 (M+H).

D. 2,6-Dimethyl-7-(2,6-dichloro-4-ethoxyphenyl)-4-(2,2-dimethoxyethyl)amino-[1,5-a]-pyrazolo-1,3,5-triazine.

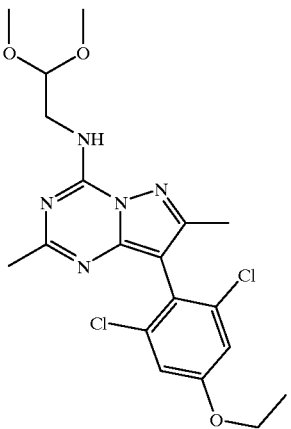

Dissolve the product from step C in dry acetonitrile and then add 2.1 equivalents of aminoacetaldehyde dimethyl acetal. Heat the solution to 60° C. and stir under a dry nitrogen atmosphere for 2–6 hours. Remove the solvent under reduced pressure, dilute with 10% NaOH and extract with ethyl acetate. Wash the combined extracts with brine, dry over anhydrous sodium sulfate and concentrate under reduced pressure to obtain a yellow oil which crystallizes upon standing. The product, 2,6-dimethyl-7-(2,6-dichloro-4-ethoxyphenyl)-4-(2,2-dimethoxyethyl)amino-[1,5-a]-pyrazolo-1,3,5-triazine, is used without further purification. MS (M+H).

E. 2-{[7-(2,6-dichloro-4-ethoxyphenyl)-2,5,6-trimethyl-3-pyrazolino[2,3-a]1,3,5-triazin-4-yl]amino} ethanal.

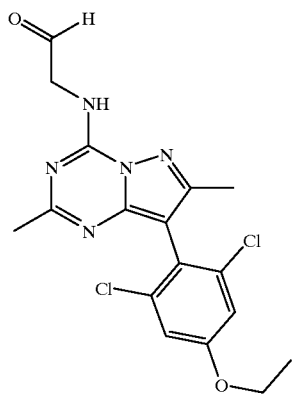

Dissolve the product obtained from step D in neat trifluoroacetic acid (25 mL). After allowing the mixture to stand at ambient temperature for 0.5 h, concentrate the mixture under reduced pressure. Add saturated aqueous sodium bicarbonate and stir the resulting heterogeneous mixture for 0.5 h. Extract the aqueous solution with EtOAc, wash the EtOAc extracts with brine and then dry over anhydrous sodium sulfate. Evaporation of the solvent under reduced pressure yields the aldehyde as an off-white foam. ¹H NMR (CDCl3): δ 9.79 (s, 1H, CHO).

F. 2-[(2-{[7-(2,6-dichloro-4-ethoxyphenyl)-2,6-dimethylpyrazolo[1,5-a]1,3,5-triazin-yl]amino}ethyl)amino]-2-methylpropan-1-ol.

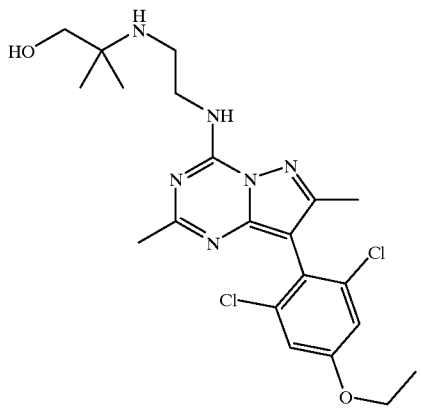

Dissolve the aldehyde (62 mg, 0.16 mmol) obtained from step E in dry dichloroethane (4 mL). Add 1.1 equivalents of 2-amino-2-methyl-1-propanol (15 μL) followed by 1 equivalent of acetic acid. After the addition of sodium triacetoxyborohydride (1.4 eq), stir the solution at ambient temperature for several hours. Dilute the reaction mixture with 4 volumes of methylene chloride then wash the mixture with brine (1x), dry over anhydrous Na2SO4. Concentrate under reduced pressure. Preparative thin layer chromatography [10% MeOH(2N NH₃)/CH₂Cl₂)] of the oily residue yields 2-[(2-{[7-(2,6-dichloro-4-ethoxyphenyl)-2,6-dimethylpyrazolo[1,5-a]triazin-4-yl]amino}ethyl)amino]-2-methylpropan-1-ol.

The preparation of the compounds of the present invention by the above-mentioned methods is illustrated further by the following examples, delineated in the TABLE which are not to be construed as limiting the invention in scope or spirit to the specific procedures and compounds described in them. Commonly used abbreviations are: Ph is phenyl, Me is methyl, Et is ethyl, Pr is n-propyl, iPr is isopropyl, cPr is cyclopropyl, Bu is butyl, iBu is isobutyl (CH₂—CHMe₂), tBu is tert-butyl, cBu is cyclobutyl, Pent is n-pentyl, cPent is cyclopentyl, cHex is cyclohexyl, Py is pyridyl, Bn is benzyl (CH₂Ph), Ac is acetyl (CH₃—(C=O)), tBOC is tert-butyloxycarbonyl (tBuO—(C=O)). EX means example.

Further experimental details of the methods of Examples 119, 132, 133, 134, 277, 279, 382 and 522 are set out below.

Example 119

Preparation of 3,5-dichloro4-{2,5-dimethyl-7-[2-(tetrahydro-pyran-4-ylamino)-ethylamin]-pyrazolo[1,5-a]pyrimidin-3-yl}-benzoic acid methyl ester.

(Formula I where X is CH, $R^1$ is $CH_3$, $R^2$ is H, A is $CH_2$, B is $CH_2$, $R^3$ is $CH_3$, $R^4$ is 2,6-dichloro-4-methoxycarbonylphenyl, $R^5$ is tetrahydropyranyl.)

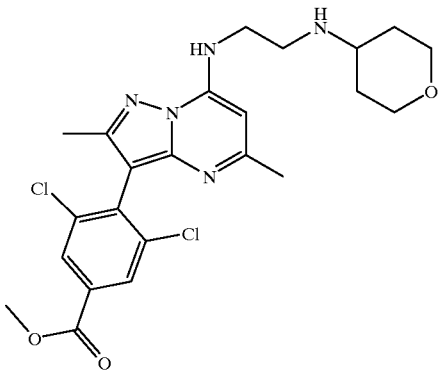

A. 4-(7-{2-[tert-Butoxycarbonyl-(tetrahydro-pyran-4-yl)-amino]-ethylamino}-2,5-dimethyl-pyrazolo[1,5-a]pyrimidin-3-yl)-3,5-dichloro-benzoic acid methyl ester A suspension of methanesulfonic acid 4-(7-{2-[tert-butoxycarbonyl-(tetrahydro-pyran-4-yl)-amino]-ethylamino}-2,5-dimethyl-pyrazolo[1,5-a]pyrimidin-3-yl)-3,5-dichloro-phenyl ester (188 mg, 0.276 mmol) from Example 134, step B, 1,3-bis(diphenylphosphino)propane (30 mg 0.073 mmol), triethylamine (0.10 mL), and palladium(II) acetate (25 mg, 0.11 mmol) in methanol (3.5 mL)/dimethylsulfoxide (3.5 mL) was degassed with a stream of carbon monoxide and then shaken for 4 hours at 70° C. under 40 psi carbon monoxide. The mixture was filtered through Celite, diluted with ethyl acetate and washed with water, dried (Na₂SO₄), concentrated under reduced pressure, and chromatographed (3:1 to 1:1 hexanes/ethyl acetate) to afford the product (144 mg, 88%): +APcI MS (M+1)⁺592; ¹H NMR (CDCl₃) δ: 8.04 (s, 2H), 5.83 (br s, 1H), 3.92 (s, 3H), 2.43 (s, 3H), 2.24 (s, 3H), 1.53 (s, 9H).

B. 3,5-Dichloro-4-{2,5-dimethyl-7-[2-(tetrahydro-pyran-4-ylamino)-ethylamino]-pyrazolo[1,5-a]pyrimidin-3-yl}-benzoic acid methyl ester To {2-[3-(2,6-Dichloro-4-cyano-phenyl)-2,5-dimethyl-pyrazolo[1,5-a]pyrimidin-7-ylamino]-ethyl}-(tetrahydro-pyran-4-yl)-carbamic acid tert-butyl ester (74 mg, 0.12 mmol) was added 2:1 ethanol/concentrated aqueous hydrochloric acid (1 mL). The reaction was stirred 3 hours at room temperature, concentrated under reduced pressure, and then concentrated 3 additional times from ethanol to give a solid that was extracted from saturated sodium bicarbonate with methylene chloride, the combined extracts were dried (CDCl₃) and concentrated under reduced pressure to give the title compound (47 mg, 80%): +APcI MS (M+1)⁺492; ¹H NMR (methanol-d₄) δ: 8.04 (s, 2H), 5.82 (s, 1H), 3.93 (s, 3H), 2.43 (s, 3H), 2.27 (s, 3H).

Example 132

Preparation of 3,5-dichloro-4-{2,5-dimethyl-7-[2-(tetrahydro-pyran-4-ylamino)-ethylamino]-pyrazolo[1,5-a]pyrimidin-3-yl}-benzonitrile hydrochloride salt.

(Formula I where X is CH, $R^1$ is $CH_3$, $R^2$ is H, A is $CH_2$, B is $CH_2$, $R^3$ is $CH_3$, $R^4$ is 2,6-dichloro-4-cyanophenyl, $R^5$ is tetrahydropyranyl.)

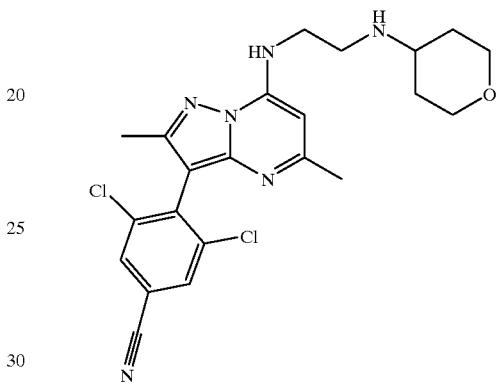

A. {2-{2-[3-(2,6-Dichloro-4-cyano-phenyl)-2,5-dimethyl-pyrazolo[1,5-a]pyrimidin-7-ylamino]-ethyl}-(tetrahydro-pyran-4-yl)-carbamic acid tert-butyl ester A suspension of methanesulfonic acid 4-(7-{2-[tert-butoxycarbonyl-(tetrahydro-pyran-4-yl)-amino]-ethylamino}-2,5-dimethyl-pyrazolo[1,5-a]pyrimidin-3-yl)-3,5-dichloro-phenyl ester (10 mg, 0.015 mmol) from Example 134, step B, zinc cyanide (2.7 mg 0.023 mmol), and palladium tetrakistriphenylphosphine (1.5 mg, 0.0013 mmol) in dimethylformamide (0.35 mL) was degassed with a stream of nitrogen and then stirred for 2 hours at 90° C. The mixture was extracted from saturated aqueous sodium bicarbonate with ethyl acetate, the combined extracts were washed with water, dried (Na₂SO₄), concentrated under reduced pressure, and chromatographed (9:1 to 5:3 to 0:1 hexanes/ethyl acetate) to afford the product (10 mg, quantitative): +APcI MS (M+1)⁺ 559; ¹H NMR (CDCl₃) δ: 7.68 (s, 2H), 5.85 (br s, 1H), 2.44 (s, 3H), 2.25 (s, 3H),1.53 ), 9H).

B. 3,5-Dichloro-4-{2,5-dimethyl-7-[2-(tetrahydro-pyran-4-ylamino)-ethylamino]-pyrazolo[1,5-a]pyrimidin-3-yl}-benzonitrile hydrochloride salt To {2-[3-(2,6-Dichloro-4-cyano-phenyl)-2,5-dimethyl-pyrazolo[1,5-a]pyrimidin-7-ylamino]-ethyl}-(tetrahydro-pyran-4-yl)-carbamic acid tert-butyl ester (10 mg, 0.015 mmol) was added 2:1 ethanol/concentrated aqueous hydrochloric acid (1 mL). The reaction was stirred 3 hours at room temperature, concentrated under reduced pressure, and then concentrated 3 additional times from ethanol to give a solid that was triturated from ether to afford the title compound (10 mg, quantitative): +APcI MS (M+1)⁺459; ¹H NMR (methanol-d₄) δ: 8.06 (s, 2H), 6.90 (s, 1H), 2.62 (s, 3H), 2.32 (s, 3H).

Example 133

Preparation of N-[3-(2,6-dichloro-4-ethyl-phenyl)-2,5-dimethyl-pyrazolo[1,5-a]pyrimidin-7-yl]-N'-(tetrahydro-pyran-4-yl)-ethane-1,2-diamine hydrochloride salt.

(Formula I where X is CH, $R^1$ is $CH_3$, $R^2$ is H, A is $CH_2$, B is $CH_2$, $R^3$ is $CH_3$, $R^4$ is 2,6-dichloro-4-ethylphenyl, $R^5$ is tetrahydropyranyl.)

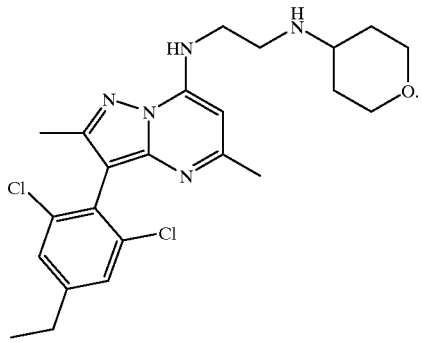

A. {2-[3-(2,6-Dichloro-4-ethyl-phenyl)-2,5-dimethyl-pyrazolo[1,5-a]pyrimidin-7-ylamino]-ethyl}-(tetrahydro-pyran-4-yl)-carbamic acid tert-butyl ester To a suspension of methanesulfonic acid 4-(7-{2-[tert-butoxycarbonyl-(tetrahydro-pyran-4-yl)-amino]-ethylamino}-2,5-dimethyl-pyrazolo[1,5-a]pyrimidin-3-yl)-3,5-dichloro-phenyl ester (1.0 g, 1.5 mmol) from Example 134, step B, powdered $K_3PO_4$ (39 mg 0.18 mmol), and dichloro[bis(diphenylphosphino)ferrocene]palladium (60 mg, 0.085 mmol) in tetrahydrofuran (7.5 mL) was added triethylborane (1 M in TBF, 2.9 mL, 2.9 mmol). The mixture was degassed with a stream of nitrogen and then stirred for 2.5 hours at 75° C. The mixture was concentrated under reduced pressure, extracted from saturated aqueous sodium bicarbonate with methylene chloride, dried ($Na_2SO_4$), and concentrated under reduced pressure to give crude product (1.07 g). Analysis by MS and $^1H$ NMR spectroscopy indicated a 1:1 mixture of product and starting material. A portion of the crude material (408 mg) was then resubjected to the above reaction conditions for 2.5 hours, then worked up as before. Chromatography (2:1 hexanes/ethyl acetate) afforded product (176 mg, 56%): +APcI MS (M+1)$^+$562; $^1H$ NMR (methanol-$d_4$) δ: 7.33 (s, 2H), 6.04 (br s, 1H), 2.66 (q, 2H), 2.37 (s, 3H), 2.20 (s, 3H), 1.42 (s, 9H), 1.25 (t, 3H).

B. N-[3-(2,6-Dichloro-4-ethyl-phenyl)-2,5-dimethyl-pyrazolo[1,5-a]pyrimidin-7-yl]-N'-(tetrahydro-pyran-4-yl)-ethane-1,2-diamine hydrochloride salt To {2-[3-(2,6-dichloro-4-ethyl-phenyl)-2,5-dimethyl-pyrazolo[1,5-a]pyrimidin-7-ylamino]-ethyl}-(tetrahydro-pyran-4-yl)-carbamic acid tert-butyl ester (0.18 g, 0.31 mmol) 2:1 ethanol/concentrated aqueous hydrochloric acid (3 mL). The reaction was stirred 15 minutes at 50° C., concentrated under reduced pressure, and then concentrated 3 additional times from ethanol to give a solid that was triturated from ether to afford the title compound (0.15 g, quantitative): +APcI MS (M+1)$^+$462; $^1H$ NMR (methanol-$d_4$) δ: 7.48 (s, 2H), 6.81 (s, 1H), 2.72 (q, 2H), 2.60 (s, 3H), 2.30 (s, 3H), 1.28 (t, 3H

Example 134

Preparation of N-[3-(2,6-Dichloro-4-ethynyl-phenyl)-2,5-dimethyl-pyrazolo[1,5-a]pyrimidin-7-yl]-N'-(tetrahydro-pyran-4-yl)-ethane-1,2-diamine.

(Formula I where X is CH, $R^1$ is $CH_3$, $R^2$ is H, A is $CH_2$, B is $CH_2$, $R^3$ is $CH_3$, $R^4$ is 2,6-dichloro-4-ethynylphenyl, $R^5$ is tetrahydropyranyl.)

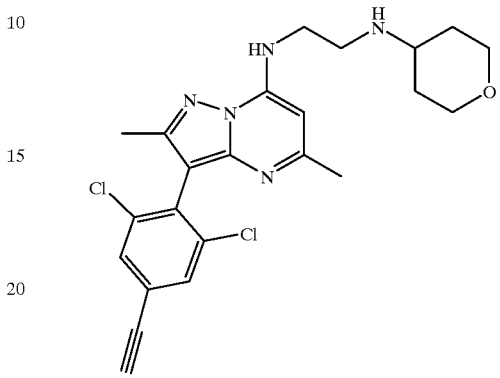

A. {2-[3-(2,6-Dichloro-4-hydroxy-phenyl)-2,5-dimethyl-pyrazolo[1,5-a]pyrimidin-7-ylamino]-ethyl}-(tetrahydro-pyran-4-yl)-carbamic acid tert-butyl ester A stirred suspension of the crude 3,5-Dichloro-4-{2,5-dimethyl-7-[2-(tetrahydro-pyran-4-ylamino)-ethylamino]-pyrazolo[1,5-a]pyrimidin-3-yl}-phenol hydrobromide salt (8.7 mmol) from Example 382, step A in methylene chloride (100 mL) was adjusted to pH 9.5 with triethyl amine, di-tert-butyl-dicarbonate (3.0 g, 14 mmol) was added and the mixture was stirred for 2 days. The reaction then extracted from saturated aqueous sodium bicarbonate with methylene chloride, the combined organic layers were dried ($Na_2SO_4$) and then concentrated under reduced pressure to give the carbamate in which the phenol had been partially acylated. To a stirred solution of the residue in methanol (50 mL) was added 0.5 M sodium methoxide in methanol (30 mL, 15 mmol). After 1 hour the reaction was concentrated and then extracted from pH 7 buffer with methylene chloride. The combined extracts were dried ($Na_2SO_4$), concentrated under reduced pressure and then chromatographed (10:1 ethyl acetate/methanol) to give the product (2.8 g, 58%) as a beige foam: +APcI MS (M+1)$^+$550; $^1H$ NMR (CDCl$_3$) δ: 6.70 (s, 2H), 5.84 (s, 1H), 2.51 (s, 3H), 2.24 (s, 3H), 1.54 (s, 9H).

B. Methanesulfonic acid 4-(7-{2-[tert-butoxycarbonyl-(tetrahydro-pyran-4-yl)-amino]-ethylamino}-2,5-dimethyl-pyrazolo[1,5-a]pyrimidin-3-yl)-3,5-dichloro-phenyl ester To a 0° C. stirred solution of {2-[3-(2,6-Dichloro-4-hydroxy-phenyl)-2,5-dimethyl-pyrazolo[1,5-a]pyrimidin-7-ylamino]-ethyl}-(tetrahydro-pyran-4-yl)-carbamic acid tert-butyl ester (2.0 g, 3.6 mmol) and 2,6-lutidine (1.2 mL, 11 mmol) in methylene chloride was added trifluoromethanesulfonic anhydride, dropwise. After 15 minutes the reaction was extracted from saturated aqueous sodium bicarbonate with methylene chloride, the combined organic layers were dried ($Na_2SO_4$), concentrated under reduced pressure, concentrated again from toluene to remove the lutidine, and then chromatographed (2:1 to 3:1 ethyl acetate/hexanes) to give the product (1.7 g, 69%) as an off-white foam: +APcI MS (M+1)$^+$682; $^1H$ NMR (CDCl$_3$) δ: 7.37 (s, 2H), 5.84 (s, 1H), 2.45 (s, 3H), 2.25 (s, 3H), 1.53 (s, 9H).

C. {2-[3-(2,6-Dichloro-4-trimethylsilanylethynyl-phenyl)-2,5-dimethyl-pyrazolo[1,5-a]pyrimidin-7-ylamino]-ethyl}-(tetrahydro-pyran-4-yl)-carbamic acid tert-butyl ester A suspension of methanesulfonic acid 4-(7-{2-[tert-butoxycarbonyl-(tetrahydro-pyran-4-yl)-amino]-ethylamino}-2,5-dimethyl-pyrazolo[1,5-a]pyrimidin-3-yl)-3,5-dichloro-phenyl ester (1.5 g, 2.2 mmol) in acetonitrile (5 mL)/triethylamine (1.9 mL) was degassed (3×) by alternately pulling a vacuum followed by repressurization with nitrogen. Trimethylsilylacetylene (0.50 mL, 3.6 mmol), dichlorobis(triphenylphosphine)palladium (65 mg, 0.093 mmol), and copper(I) iodide (42 mg, 0.22 mmol) were added, and the mixture was degassed (3×) again. The mixture was stirred for 4 hours at 65° C., the black mixture was extracted from saturated aqueous sodium bicarbonate with methylene chloride, dried ($Na_2SO_4$), filtered through Celite, concentrated under reduced pressure, and then chromatographed (7:3 hexanes/ethyl acetate) to give the product as a light brown foam (1.2 g, 89%): +APcI MS $(M+1)^+$ 630; $^1$H NMR ($CDCl_3$) δ: 7.51 (s, 2H), 5.82 (s, 1H), 2.44 (s, 3H), 2.23 (s, 3H), 1.53 (s, 9H), 0.24 (s, 9H).

D. N-[3-(2,6-Dichloro-4-ethynyl-phenyl)-2,5-dimethyl-pyrazolo[1,5-a]pyrimidin-7-yl]-N'-(tetrahydro-pyran-4-yl)-ethane-1,2-diamine To a stirred solution of {2-[3-(2,6-dichloro-4-trimethylsilanylethynyl-phenyl)-2,5-dimethyl-pyrazolo[1,5-a]pyrimidin-7-ylamino]-ethyl}-(tetrahydro-pyran-4-yl)-carbamic acid tert-butyl ester (1.2 g, 2.0 mmol) in ethanol (2 mL) was added KOH (0.2 g, 8 mmol). After 1 hour, the reaction was cooled to 0° C. and 1:1 ethanol/concentrated aqueous hydrochloric acid (4 mL) was added and the mixture was allowed to warm to room temperature. After 1 day, the reaction was concentrated under reduced pressure, extracted from saturated aqueous sodium bicarbonate with methylene chloride, the combined extracts were dried ($Na_2SO_4$), concentrated under reduced pressure, and then chromatographed (4:1 to 10:3 to 3:2 ethyl acetate/methanol) to afford the title compound (0.70 g, 78%) as an off-white solid: +APcI MS $(M+1)^+$ 458; $^1$H NMR (methanol-$d_4$) δ: 7.58 (d, 1H), 6.10 (s, 1H), 3.76 (s, 1H), 2.39 (s, 3H), 2.23 (s, 3H).

Example 277

4-{2-[3-(2,6-Dichloro-4-methoxy-phenyl)-2,5-dimethyl-pyrazolo [1,5-a]pyrimidin-7-ylamino]-ethylamino}-cyclohexanol

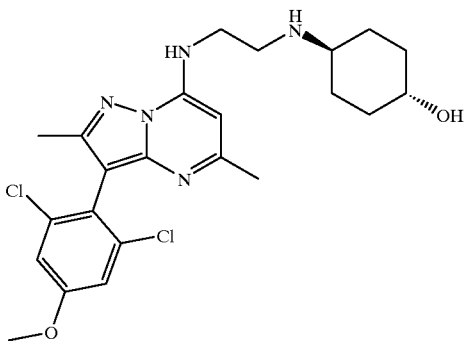

A. Preparation of [2-(4-hydroxy-cyclohexylamino)-ethyl]-carbamic acid tert-butyl ester:

A mixture of N-tert-butoxycarbonylglycinal (5 g, 31.4 mmol), trans 4-amino-cyclohexanol (3.6 g, 31.4 mmol), sodium cyanoborohydride (1.98 g, 314 mmol) in 1:20 HOAc/MeOH (105 mL) was stirred at room temperature for 72 h. The reaction mixture was diluted with EtOAc and was washed with sat'd aq $NaHCO_3$, sat aq NaCl, dried, and concentrated in vacuo to give 3.7 g of an oily residue. MS 259 ($MH^+$).

B. Preparation of 4-(2-amino-ethylamino)-cyclohexanol: The product obtained in step A was treated with 1:1 conc HCl/MeOH (40 mL) and was stirred for 1 hr. The reaction mixture was concentrated in vacuo to give 3.3 g of the desired product. MS 159 ($MH^+$).

C. A solution of 7-chloro-3-(2,6-dichloro-4-methoxy-phenyl)-2,5-dimethyl-pyrazolo[1,5-a]pyrimidine (5.1 g, 14.3 mmol), triethylamine (15 mL) and the product from step B (3.3 g, 14.3 mmol) was heated under reflux for 17 h. The reaction mixture was cooled to room temperature and the solvent was removed under vacuum. The residue was dissolved in EtOAc, washed with sat'd aq $NaHCO_3$, sat'd aq NaCl, dried and concentrated. The crude residue was purified on $SiO_2$-gel using a gradient of 100% EtOAc to 10% $Et_2NH$/EtOAc to give 400 mg of the desired product. A portion of the product (20 mg) was treated with 4 M HCl (1 mL) in dioxane (5 ml) and the reaction mixture was concentrated in vacuo to give the HCl salt. $^1$H NMR (Unity-400, $CD_3OD$): δ 7.2 (s), 6.8 (s), 4.08 (m), 3.65 (s), 3.4 (m), 2.6 (s), 2.3 (s), 2.2 (d), 2.05 (d), 1.6–1.3 (m). MS 478 ($MH^+$), 480 ($MH^{+2}$).

Example 279

Preparation of N-[3-(2,6-dichloro-4-methoxy-phenyl)-2,5-dimethyl-pyrazolo[1,5-a]pyrimidin-7-yl]-N'-(tetrahydro-pyran-4-yl)-ethane-1,2-diamine hydrochloride salt.

(Formula I where X is CH, $R^1$ is $CH_3$, $R^2$ is H, A is $CH_2$, B is $CH_2$, $R^3$ is $CH_3$, $R^4$ is 2,6-dichloro-4-methoxyphenyl, $R^5$ is tetrahydropyranyl.)

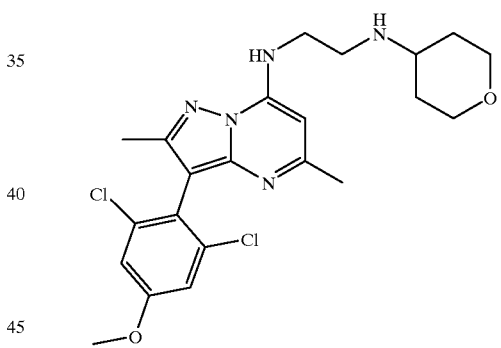

A. (2,6-Dichloro-4-methoxy-phenyl)-acetonitrile and (2,4-Dichloro-6-methoxy-phenyl)-acetonitrile A solution of 1,3-dichloro-2-chloromethyl-5-methoxy-benzene (5.0 g, 22 mmol), contaminated with the corresponding 4-chloromethyl and di-(chloromethyl) isomers (J. Med. Chem., 31, 72 (1988)) in refluxing dichloromethane (30 mL) was treated with tetraethylammonium cyanide in four portions over 25 minutes. Ten minutes after the final addition the reaction was cooled and then extracted from saturated aqueous sodium bicarbonate with ethyl acetate. The combined organic layers were dried ($Na_2SO_4$), concentrated under reduced pressure, and then chromatographed (6:1 hexanes/ethyl acetate) to give the title compounds (2:1 ratio, 3.4 g, 71%) as a colorless solid. (2,6-Dichloro-4-methoxy-phenyl)-acetonitrile: $^1$H NMR ($CDCl_3$) δ: 6.91 (s, 2H), 3.91 (s, 2H), 3.79 (s, 3H). (2,4-Dichloro-6-methoxy-phenyl)-acetonitrile: $^1$H NMR ($CDCl_3$) δ: 7.06 (d, 1H), 6.82 (d, 1H), 3.89 (s, 2H), 3.79 (s, 3H).

B. 4-(2,6-Dichloro-4-methoxy-phenyl)-5-methyl-2H-pyrazol-3-ylamine

To a stirred solution of the (2,6-dichloro-4-methoxy-phenyl)-acetonitrile and (2,4-dichloro-6-methoxy-phenyl)-acetonitrile (20 g, 96 mmol) in ethyl acetate (95 mL) was added sodium ethoxide in ethanol (21 wt. %, 95 mL, 0.25 mol). The reaction was heated at reflux for 4 hours, and then cooled, diluted with water and washed with diethyl ether. The aqueous layer was acidified to pH 4 with 1 M HCl and then extracted with methylene chloride. The combined organic layers were dried ($Na_2SO_4$) and concentrated under reduced pressure to give a brown oil (20 g, 83%).

To a solution of the brown oil in benzene (150 mL) was added acetic acid (16 mL), which caused the formation of a colorless precipitate. Hydrazine hydrate was added (7.6 mL, 0.16 mol) and the reaction was heated to reflux, at which point the reaction became homogeneous. After 16 hours, an additional portion of hydrazine hydrate was added (5 mL, 0.10 mmol) and the mixture was heated for 24 more hours. The reaction was cooled and then extracted with 1 M HCl. The combined aqueous layers were adjusted to pH 8 with aqueous ammonium hydroxide (cooled in an ice bath) and then extracted with methylene chloride. The combined organic layers were dried ($Na_2SO_4$), concentrated under reduced pressure, and then chromatographed (10:1:0.1 ethyl acetate/diethylamine/methanol) to give the title compound (6 g, 29% from A) as a colorless solid: $^1$HNMR (CDCl$_3$) δ: 6.98 (s, 2H), 3.81 (s, 3H), 2.16 (s, 3H).

C. 3-(2,6-Dichloro-4-methoxy-phenyl)-2-methyl-4H-pyrazolo[1,5-a]pyrimidin-7-one

To a solution of 4-(2,6-dichloro-4-methoxy-phenyl)-5-methyl-2H-pyrazol-3-ylamine (10.1 g, 39 mmol) in acetic acid (17 mL) was added methyl acetoacetate. After the mixture was heated at reflux for 3 hours it was cooled and then diluted with diethyl ether (50 mL) to generate a colorless precipitate. The solid was collected by vacuum filtration and washed with additional ether to afford the title compound as a colorless solid (10.3 g, 77%): +APcI MS (M+1)$^+$338; $^1$H NMR (methanol-d$_4$) δ: 7.14 (s, 2H), 5.68 (s, 1H), 3.86 (s, 3H), 2.30 (s, 3H), 2.16 (s, 3H).

D. 7-Chloro-3-(2,6-dichloro-4-methoxy-phenyl)-2,5-dimethyl-pyrazolo[1,5-a]pyrimidine A suspension of 3-(2,6-dichloro-4-methoxy-phenyl)-2-methyl-4H-pyrazolo[1,5-a]pyrimidin-7-one (10.3 g, 31 mmol) in phosphorus oxychloride (60 mL) was stirred at reflux. After 2 hours the homogeneous red solution was concentrated under reduced pressure and then extracted from saturated sodium bicarbonate with chloroform. The combined organic layers were dried ($Na_2SO_4$) and then concentrated under reduced pressure to give the title compound (10.2 g, 94%) as a red solid: +APcI MS (M+1)$^+$356; $^1$H NMR (CDCl$_3$) δ: 7.05 (s, 2H), 6.84 (s, 1H), 3.886 (s, 3H), 2.59 (s, 3H), 2.42 (s, 3H).

E N-[3-(2,6-Dichloro-4-methoxy-phenyl)-2,5-dimethyl-pyrazolo[1,5-a]pyrimidin-7-yl]-ethane-1,2-diamine To a stirred solution of ethylene diamine (19 mL, 0.28 mol) in ethanol (40 mL) was added a solution of 7-chloro-3-(2,6-dichloro-4-methoxy-phenyl)-2,5-dimethyl-pyrazolo[1,5-a]pyrimidine (9.9 g, 28 mmol) in methylene chloride (30 mL), dropwise over 1 hour. After refluxing 2 hours the reaction was concentrated under reduced pressure, extracted from saturated aqueous sodium bicarbonate with chloroform, the combined extracts were dried ($Na_2SO_4$) and then concentrated under reduced pressure to give the title compound as a yellow solid (10.42 g, 98%): +APcI MS (M+1)$^+$380; $^1$H NMR (CDCl$_3$) δ: 6.97 (s, 2H), 5.81 (s, 1H), 3.80 (s, 3H), 3.45 (m, 2H), 3.07 (t, 2H), 2.44 (s, 3H), 2.26 (s, 3H).

F N-[3-(2,6-Dichloro-4-methoxy-phenyl)-2,5-dimethyl-pyrazolo[1,5-a]pyrimidin-7-yl]-N'-(tetrahydro-pyran-4-yl)-ethane-1,2-diamine hydrochloride salt To a stirred solution of N-[3-(2,6-dichloro-4-methoxy-phenyl)-2,5-dimethyl-pyrazolo[1,5-a]pyrimidin-7-yl]-ethane-1,2-diamine (3.32 g, 8.7 mmol) and tetrahydro-4H-pyran-4-one (1.8 g, 18 mmol) in methanol (60 mL)/acetic acid (1.6 g) was added sodium cyanoborohydride (1.1 g, 17 mmol), portionwise. After stirring 1 hour the reaction was concentrated under reduced pressure and then extracted from saturated aqueous sodium bicarbonate with ethyl acetate. The combined extracts were dried ($Na_2SO_4$), concentrated under reduced pressure to give the crude product as a colorless foam (4.1 g, quant). A solution of the product in ether (150 mL) was treated with 1 M ethereal HCl which generated a precipitate that was collected by vacuum filtration to give the title compound (4.1 g, 94%) as a pink solid: +APcI MS (M+1)$^+$464; $^1$H NMR (methanol-d$_4$) δ: 7.14 (s, 2H), 6.38 (s, 1H), 4.03 (dd, 2H), 3.94 (br t, 2H), 3.86 (s, 3H), 3.50–3.38 (m, 5H), 2.51 (s, 3H), 2.26 (s, 3H), 2.05 (m, 2H), 1.68 (qd, 2H).

Example 382

Preparation of N-[3-(2,6-dichloro-4-propoxy-phenyl)-2,5-dimethyl-pyrazolo[1,5-a]pyrimidin-7-yl]-N'-(tetrahydro-pyran-4-yl)-ethane-1,2-diamine hydrochloride salt.

(Formula I where X is CH, $R^1$ is CH$_3$, $R^2$ is H, A is CH$_2$, B is CH$_2$, $R^3$ is CH$_3$, $R^4$ is 2,6-dichloro-4-propoxyphenyl, $R^5$ is tetrahydropyranyl.)

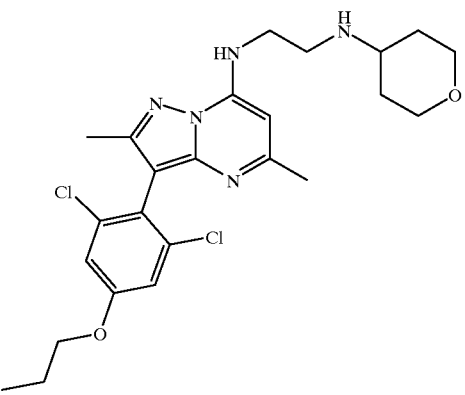

A. 3,5-Dichloro-4-{2,5-dimethyl-7-[2-(tetrahydro-pyran-4-ylamino)-ethylamino]-pyrazolo [1,5-a]pyrimidin-3-yl}-phenol hydrobromide salt A suspension of N-[3-(2,6-dichloro-4-methoxy-phenyl)-2,5-dimethyl-pyrazolo[1,5-a]pyrimidin-7-yl]-N'-(tetrahydro-pyran-4-yl)-ethane-1,2-diamine (4.1 g, 8.2 mmol), from Example 279, step F, in concentrated aqueous HBr (30 mL) was stirred at reflux. After 5 hours the reaction was concentrated under reduced pressure at 70° C. to give the hydrogen bromide salt as a brown oil (7.35 g). A small portion was triturated from ether to give the product as a brown solid: +APcI MS (M+1)$^+$450; $^1$H NMR (methanol-d$_4$) δ: 7.00 (s, 2H), 6.85 (s, 1H), 4.11 (t, 2H), 4.02 (dd, 2H), 3.60–3.40 (m, 5H), 2.61 (s, 3H), 2.29 (s, 3H), 2.095 (m, 2H), 1.74 (qd, 2H).

B. N-[3-(2,6-Dichloro-4-propoxy-phenyl)-2,5-dimethyl-pyrazolo[1,5-a]pyrimidin-7-yl]-N'-(tetrahydro-pyran-4-yl)-ethane-1,2-diamine hydrochloride salt A solution of crude 3,5-Dichloro-4-{2,5-dimethyl-7-[2-(tetrahydro-pyran-4-ylamino)-ethylamino]-pyrazolo[1,5-a]pyrimidin-3-yl}-phenol hydrobromide salt (8.7 mmol) from step A in isopropyl alcohol (50 mL) was adjusted to pH 12 with 6 M aqueous NaOH. Propyl iodide (1.3 mL, 14 mmol) was added and the reaction was heated at reflux for 4 hours. The reaction was cooled and then extracted from saturated aqueous sodium bicarbonate with methylene chloride, dried (Na$_2$SO$_4$), concentrated under reduced pressure, and then chromatographed (10:1:0.1 methylene chloride/methanol/ammonium hydroxide) to give the product (2.0 g, 47%). A solution of the product in ethanol was treated with 1 M ethereal HCl (1 eq., 4.1 mmol), the mixture was concentrated to give a solid which was repulped from 1:1 ethanol/ether. The solids were collected to give the title compound (700 mg) as a colorless solid. The mother liquor was concentrated and then repulped from ether to give the remainder of the product as an off-white solid (1.3 g): +APcI MS (M+1)$^+$492; $^1$H NMR (methanol-d$_4$) δ: 7.21 (s, 2H), 6.67 (s, 1H), 2.61 (s, 3H), 2.33 (s, 3H), 1.10 (t, 3H).

Example 522

[3-(2,6-Dichloro-4-methoxy-phenyl)-2,5-dimethyl-pyrazolo[1,5-a]pyrimidin-7-yl]-(6-methyl-piperidin-2-ylmethyl)-amine)

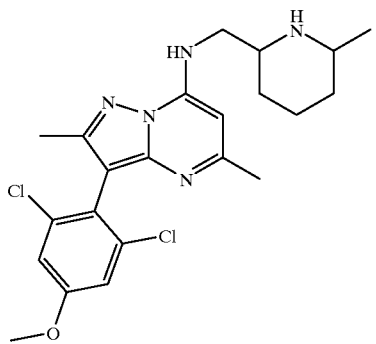

A. Preparation of methanesulfonic acid 6-methyl-pyridin-2-yl ester: Methanesulfonyl chloride (0.94 mL, 12.18 mmol) was added to a solution of 6-methyl-2-pyridinemethanol (1 g, 8.12 mmol) and triethylamine (1.7 mL, 12.18 mmol) in THF (20 mL) at 0 C. The reaction mixture was stirred for 40 min, then was quenched with sat'd aq NaHCO$_3$ and extracted with EtOAc. The combined organic extracts were washed with sat'd aq NaCl, dried and concentrated in vacuo. The crude residue was chromato graphed on SiO$_2$-gel using 50% EtOAc/hexane to give the product as an oil. $^1$H NMR (Unity-400, CDCl$_3$): δ 7.6 (t), 7.26 (d), 7.15 (d), 5.28 (s), 3.1 (s), 2.5 (s).

B. Preparation of 2-azidomethyl-6-methyl-pyridine: A mixture of the mesylate (1.0 g, 9.45 mmol) and sodium azide (610 mg, 9.45 mmol) in DMSO (40 mL) was stirred for 1 hr at room temperature. The reaction mixture was poured into EtOAc and was washed with sat'd aq NaCl, dried and concentrated in vacuo. The crude residue was purified using silica gel chromatography (25% EtOAc/hexanes) to give 936 mg of desired product. $^1$H NMR (Unity-400, CDCl$_3$): δ 7.6 (t), 7.1 (d), 7.08 (d), 4.43 (s), 2.54 (s).

C. Preparation of (6-methyl-piperidin-2-yl)-methylamine: A mixture of the product obtained in Step B (860 mg) and PtO$_2$ (86 mg) in acetic acid (20 mL) was hydrogenated in a Paar Shaker at 40 psi for 17 h. The reaction mixture was filtered and the filtrate was concentrated under vacuum to give 2 g of the desired product. $^1$H NMR (Unity-400, CD$_3$OD): δ 3.1, 1.93 (s), 1.88 (m), 1.55 (m), 1.28 (dd, 3 H).

D. Preparation of [3-(2,6-dichloro-4-methoxy-phenyl)-2,5-dimethyl-pyrazolo[1,5-a]pyrimidin-7-yl]-(6-methyl-piperidin-2-ylmethyl)-amine): A solution of 7-chloro-3-(2,6-dichloro-4-methoxy-phenyl)-2,5-dimethyl-pyrazolo[1,5-a]pyrimidine (50 mg, 0.11 mmol), triethylamine (1 mL) and the product from step C (42 mg, 0.22 mmol) in EtOH (3 mL) was heated under reflux for 17 h. The reaction was concentrated under vacuum. The residue was diluted with sat'd aq NaHCO$_3$ and the aqueous solution was extracted with EtOAc (3x), dried and concentrated in vacuo. The crude residue was purified on a prep TLC plate using 1.5% Et$_2$NH/EtOAc to give 36 mg of the desired product. $^1$H NMR (Unity-400, CDCl$_3$): δ 7.0 (s, 2H), 5.94 (s, 1H), 3.8 (s, 3H), 3.53 (m), 3.05 (m), 2.8 (m), 2.44 (s, 3H), 2.27 (s, 3H). 1.9 (m), 1.7 (m). MS 4.48 (M).

Table of Additional Examples

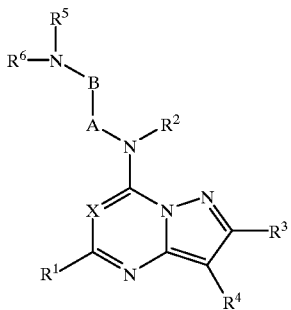

| EX | X | R$^1$ | R$^2$ | R$^3$ | R$^4$ | A-B-N[R$^6$]-R$^5$ | MW |
|---|---|---|---|---|---|---|---|
| 9. | N | Me | H | Me | 2-Br-4,5-diOMe-Ph | (CH2)2-NH-(CH2)2-(3-OMe-4-EtO-Ph) | 599.53 |
| 10. | CH | Me | H | Me | 2-Br-6-Cl-Ph | (CH2)2-NH-(tetrahydropyran-4-yl) | 478.8 |
| 11. | CH | Me | H | Me | 2-Cl-Ph | (CH2)2-NH-(CH2)2-(4-OMe-Ph) | 486.44 |
| 12. | CH | Me | H | Me | 2-OMe-4-OEt-6-F-Ph | (CH2)2-NH-(tetrahydropyran-4-yl) | 457.54 |
| 13. | CH | Me | H | Me | 2,4-diCl-6-(OSO2CF3)-Ph | (CH2)2-NH-(tetrahydropyran-4-yl) | 528.43 |
| 14. | CH | Me | H | Me | 2,4-diCl-6-OEt-Ph | (CH2)2-NH-(1-(pyrimidin-2-yl)-piperidin-4-yl) | 555.5 |
| 15. | CH | Me | H | Me | 2,4-diCl-6-OEt-Ph | (CH2)2-NH-(4-ethyleneketal-cHex) | 534.48 |
| 16. | CH | Me | H | Me | 2,4-diCl-6-OEt-Ph | (CH2)2-NH-(tetrahydropyran-4-yl) | 478.4 |

-continued

Table of Additional Examples

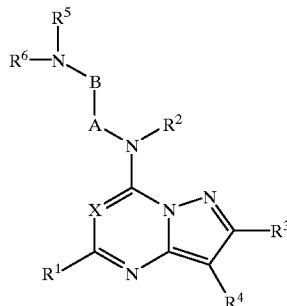

| EX | X | R¹ | R² | R³ | R⁴ | A-B-N[R⁶]-R⁵ | MW |
|---|---|---|---|---|---|---|---|
| 17. | CH | Me | H | Me | 2,4-diCl-6-OEt-Ph | (CH2)2-NH-(tetrahydropyran-4-yl) | 478.41 |
| 18. | CH | Me | H | Me | 2,4-diCl-6-OH-Ph | (CH2)2-NH-(tetrahydropyran-4-yl) | 450.4 |
| 19. | CH | Me | H | Me | 2,4-diCl-6-OMe-Ph | (CH2)2-NH-(1-Bn-piperidin-4-yl) | 553.5 |
| 20. | CH | Me | H | Me | 2,4-diCl-6-OMe-Ph | (CH2)2-NH-(4-ethoxyimino-cHex) | 519.5 |
| 21. | CH | Me | H | Me | 2,4-diCl-6-OMe-Ph | (CH2)2-NH-(4-ethyleneketal-cHex) | 520.5 |
| 22. | CH | Me | H | Me | 2,4-diCl-6-OMe-Ph | (CH2)2-NH-(4-isobutoxyimino-cHex) | 547.5 |
| 23. | CH | Me | H | Me | 2,4-diCl-6-OMe-Ph | (CH2)2-NH-(4-methoxyimino-cHex) | 505.5 |
| 24. | CH | Me | H | Me | 2,4-diCl-6-OMe-Ph | (CH2)2-NH-(4-OH-cHex) | 478.43 |
| 25. | CH | Me | H | Me | 2,4-diCl-6-OMe-Ph | (CH2)2-NH-(7-methoxyimino-azepan-3-yl) | 520.5 |
| 26. | CH | Me | H | Me | 2,4-diCl-6-OMe-Ph | (CH2)2-NH-(CH2)2-OH | 424.33 |
| 27. | CH | Me | H | Me | 2,4-diCl-6-OMe-Ph | (CH2)2-NH-(tetrahydropyran-4-yl) | 464.4 |
| 28. | CH | Me | H | Me | 2,4-diCl-6-OMe-Ph | (CH2)2-NH-cyclohexan-4-oxime | 491.42 |
| 29. | CH | iPr | H | Me | 2,4-diCl-Ph | (CH2)2-NH-(1-(pyrimidin-2-yl)-piperidin-4-yl) | 539.52 |
| 30. | N | Me | H | Me | 2,4-diCl-Ph | (CH2)2-NH-(1-(pyrimidin-2-yl)-piperidin-4-yl) | 512.44 |
| 31. | CH | Me | H | Me | 2,4-diCl-Ph | (CH2)2-NH-(1-Bn-piperidin-4-yl) | 523.51 |
| 32. | N | Me | H | Me | 2,4-diCl-Ph | (CH2)2-NH-(1-Bn-piperidin-4-yl) | 524.5 |
| 33. | CH | Me | H | CF3 | 2,4-diCl-Ph | (CH2)2-NH-(1-Bn-piperidin-4-yl) | 577.48 |
| 34. | CH | Me | H | Me | 2,4-diCl-Ph | (CH2)2-NH-(2-Cl-cHex) | 466.84 |
| 35. | CH | Me | H | Me | 2,4-diCl-Ph | (CH2)2-NH-(2-Cl-cPent) | 452.82 |
| 36. | CH | Me | H | Me | 2,4-diCl-Ph | (CH2)2-NH-(2-Me-cHex) | 446.42 |
| 37. | CH | Me | H | Me | 2,4-diCl-Ph | (CH2)2-NH-(2-OH-cHex) | 448.39 |
| 38. | CH | Me | H | Me | 2,4-diCl-Ph | (CH2)2-NH-(2-OMe-cHex) | 462.42 |
| 39. | N | Me | H | Me | 2,4-diCl-Ph | (CH2)2-NH-(2F-cPent) | 436.3 |
| 40. | CH | Me | H | Me | 2,4-diCl-Ph | (CH2)2-NH-(3-Me-cyclohex-2-enyl) | 444.41 |
| 41. | CH | iPr | H | Me | 2,4-diCl-Ph | (CH2)2-NH-(4-CF3-cHex) | 528.45 |
| 42. | N | Me | H | Me | 2,4-diCl-Ph | (CH2)2-NH-(4-methoximino-cHex) | 476.4 |
| 43. | CH | Me | H | Me | 2,4-diCl-Ph | (CH2)2-NH-(4,4-diMe-cyclohex-2-enyl) | 458.43 |
| 44. | CH | Me | H | Me | 2,4-diCl-Ph | (CH2)2-NH-(CH2)2-(2-OMe-Ph) | 484.42 |
| 45. | N | Me | H | Me | 2,4-diCl-Ph | (CH2)2-NH-(CH2)2-(3-OMe-4-EtO-Ph) | 529.47 |
| 46. | CH | Me | H | Me | 2,4-diCl-Ph | (CH2)2-NH-(CH2)2-(3-OMe-4-OEt-Ph) | 528.47 |
| 47. | CH | Me | H | Me | 2,4-diCl-Ph | (CH2)2-NH-(CH2)2-(4-OMe-Ph) | 484.42 |
| 48. | CH | iPr | H | Me | 2,4-diCl-Ph | (CH2)2-NH-(cis-4-CF3-cHex) | 528.45 |
| 49. | CH | iPr | H | Me | 2,4-diCl-Ph | (CH2)2-NH-(tetrahydropyran-4-yl) | 462.43 |
| 50. | CH | Me | H | Me | 2,4-diCl-Ph | (CH2)2-NH-(tetrahydropyran-4-yl) | 450.44 |
| 51. | CH | Me | H | Me | 2,4-diCl-Ph | (CH2)2-NH-(tetrahydropyran-4-yl) | 434.37 |
| 52. | N | Me | H | Me | 2,4-diCl-Ph | (CH2)2-NH-2-norbornyl | 445.4 |
| 53. | N | Me | H | Me | 2,4-diCl-Ph | (CH2)2-NH-CHMe-(CH2)2-NEt2 | 478.5 |
| 54. | N | Me | H | Me | 2,4-diCl-Ph | (CH2)2-NH-CHMe-CH2-NEt2 | 464.4 |
| 55. | CH | Me | H | Me | 2,4-diCl-Ph | (CH2)2-NH-cyclohex-2-enyl | 430.38 |
| 56. | CH | Me | H | Me | 2,4-diCl-Ph | (CH2)2-NH-piperidin-4-yl | 433.38 |
| 57. | CH | Me | H | Me | 2,4-diCl-Ph | CMe2-CH2-OH | 422.36 |
| 58. | CH | Me | H | Me | 2,4-diF-Ph | (CH2)2-NH-(CH2)2-(3-OMe-4-OEt-Ph) | 495.57 |
| 59. | CH | Et | H | Me | 2,4-diMe-Ph | (CH2)2-NH-(1-(pyrimidin-2-yl)-piperidin-4-yl) | 484.7 |
| 60. | CH | nPr | H | Me | 2,4-diMe-Ph | (CH2)2-NH-(1-(pyrimidin-2-yl)-piperidin-4-yl) | 498.7 |
| 61. | CH | Et | H | Me | 2,4-diMe-Ph | CH2-CHMe-NH-(1-(pyrimidin-2-yl)-piperidin-4-yl) | 498.7 |
| 62. | CH | nPr | H | Me | 2,4-diMe-Ph | CH2-CHMe-NH-(1-(pyrimidin-2-yl)-piperidin-4-yl) | 512.7 |
| 63. | CH | Me | H | Me | 2,4-diOMe-6-Cl-Ph | (CH2)2-NH-(1-(5-Et-pyrimidin-2-yl)-piperidin-4-yl) | 565.11 |
| 64. | CH | Me | H | Me | 2,4-diOMe-6-Cl-Ph | (CH2)2-NH-(1-(pyrimidin-2-yl)-piperidin-4-yl) | 537.1 |
| 65. | CH | Me | H | Me | 2,4-diOMe-6-Cl-Ph | (CH2)2-NH-(1-Ac-piperidin-4-yl) | 501.02 |
| 66. | CH | Me | H | Me | 2,4-diOMe-6-Cl-Ph | (CH2)2-NH-(1-COOEt-piperidin-4-yl) | 531.0 |
| 67. | CH | Me | H | Me | 2,4-diOMe-6-Cl-Ph | (CH2)2-NH-(1-SO2Me-piperidin-4-yl) | 537.08 |
| 68. | CH | Me | H | Me | 2,4-diOMe-6-Cl-Ph | (CH2)2-NH-(4-(NH-iBu)-cHex) | 529.12 |
| 69. | CH | Me | H | Me | 2,4-diOMe-6-F-Ph | (CH2)2-NH-(1-Ac-piperidin-4-yl) | 484.57 |
| 70. | CH | Me | H | Me | 2,4-diOMe-6-F-Ph | (CH2)2-NH-(1-Bn-piperidin-4-yl) | 532.65 |
| 71. | CH | Me | H | Me | 2,4-diOMe-6-F-Ph | (CH2)2-NH-(4-ethyleneketal-cHex) | 499.58 |
| 72. | CH | Me | H | Me | 2,4-diOMe-6-F-Ph | (CH2)2-NH-(4-oxo-cHex) | 455.23 |
| 73. | CH | Me | H | Me | 2,4-diOMe-6Cl-Ph | (CH2)2-NH-(1-Bn-piperidin-4-yl) | 549.1 |
| 74. | CH | Me | H | Me | 2,4-diOMe-6Cl-Ph | (CH2)2-NH-(1-tBoc-piperidin-4-yl) | 559.1 |
| 75. | CH | Me | H | Me | 2,4-diOMe-6Cl-Ph | (CH2)2-NH-(4-ethyleneketal-cHex) | 516 |

-continued

Table of Additional Examples

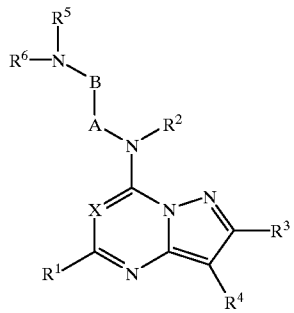

| EX | X | R¹ | R² | R³ | R⁴ | A-B-N[R⁶]-R⁵ | MW |
|---|---|---|---|---|---|---|---|
| 76. | CH | Me | H | Me | 2,4-diOMe-6Cl-Ph | (CH2)2-NH-(4-oxo-cHex) | 471.99 |
| 77. | CH | Me | H | Me | 2,4-diOMe-6Cl-Ph | (CH2)2-NH-(tetrahydropyran-4-yl) | 459.98 |
| 78. | CH | Me | H | Me | 2,4-diOMe-6Cl-Ph | (CH2)2-NH-piperidin-4-yl | 458.99 |
| 79. | CH | Me | H | Me | 2,4,6-triCl-Ph | (CH2)2-NH-(4-(1-morpholino)-cHex) | 533.51 |
| 80. | CH | Me | H | Me | 2,4,6-triCl-Ph | (CH2)2-NH-(4-ethyleneketal-cHex) | 524.9 |
| 81. | CH | Me | H | Me | 2,4,6-triCl-Ph | (CH2)2-NH-(4-NHMe-cHex) | 477.44 |
| 82. | CH | Me | H | Me | 2,4,6-triCl-Ph | (CH2)2-NH-(tetrahydropyran-4-yl) | 468.8 |
| 83. | CH | Me | H | Me | 2,4,6-triCl-Ph | CH2-CHMe-NH-(4-NHMe-cHex) | 491.47 |
| 84. | CH | Me | H | Me | 2,4,6-triMe-Ph | (CH2)2-3-pyridyl | 428.58 |
| 85. | CH | Et | H | Me | 2,4,6-triMe-Ph | (CH2)2-NH-(1-(pyrimidin-2-yl)-piperidin-4-yl) | 498.7 |
| 86. | CH | Et | H | Me | 2,4,6-triMe-Ph | (CH2)2-NH-(1-(pyrimidin-2-yl)-piperidin-4-yl) | 512.7 |
| 87. | CH | nPr | H | Me | 2,4,6-triMe-Ph | (CH2)2-NH-(1-(pyrimidin-2-yl)-piperidin-4-yl) | 512.7 |
| 88. | CH | Me | H | Me | 2,4,6-triMe-Ph | (CH2)2-NH-(1-(pyrimidin-2-yl)-piperidin-4-yl) | 484.7 |
| 89. | CH | Me | H | Me | 2,4,6-triMe-Ph | (CH2)2-NH-(1-(pyrimidin-2-yl)-piperidin-4-yl) | 484.64 |
| 90. | CH | Et | H | Me | 2,4,6-triMe-Ph | (CH2)2-NH-(1-Ac-piperidin-4-yl) | 462.6 |
| 91. | CH | Me | H | Me | 2,4,6-triMe-Ph | (CH2)2-NH-(1-COOEt-piperidin-4-yl) | 478.64 |
| 92. | CH | Et | H | Me | 2,4,6-triMe-Ph | (CH2)2-NH-(1,2,3,4-tetrahydro-naphthalen-2-yl) | 467.7 |
| 93. | CH | Me | H | Me | 2,4,6-triMe-Ph | (CH2)2-NH-(CH2)2-(1-Me-pyrrolidin-2-yl) | 434.63 |
| 94. | CH | Et | H | Me | 2,4,6-triMe-Ph | (CH2)2-NH-(CH2)2-(3-OMe-4-EtO-Ph) | 515.70 |
| 95. | CH | CH3 | H | Et | 2,4,6-triMe-Ph | (CH2)2-NH-(CH2)2-(3-OMe-4-EtO-Ph) | 515.70 |
| 96. | CH | iPr | H | Me | 2,4,6-triMe-Ph | (CH2)2-NH-(CH2)2-(3-OMe-4-EtO-Ph) | 529.73 |
| 97. | CH | nPr | H | Me | 2,4,6-triMe-Ph | (CH2)2-NH-(CH2)2-(3-OMe-4-EtO-Ph) | 529.73 |
| 98. | CH | Ph | H | Me | 2,4,6-triMe-Ph | (CH2)2-NH-(CH2)2-(3-OMe-4-EtO-Ph) | 563.74 |
| 99. | CH | Me | H | Me | 2,4,6-triMe-Ph | (CH2)2-NH-(trans-4-COOEt-cHex) | 477.64 |
| 100. | CH | Me | H | Me | 2,4,6-triMe-Ph | (CH2)2-NH-(trans-4-COOH-cHex) | 449.59 |
| 101. | CH | Et | H | Me | 2,4,6-triMe-Ph | (CH2)2-NH-CHMe-Ph | 441.6 |
| 102. | CH | Me | H | CH2-OMe | 2,4,6-triMe-Ph | (CH2)2-NH-cPent | 421.59 |
| 103. | CH | Me | H | Me | 2,4,6-triMe-Ph | (CH2)2-NH-cyclohex-3-enyl | 403.6 |
| 104. | CH | Me | H | Me | 2,4,6-triMe-Ph | (CH2)3-NH-CH2-(3,4-diOMe-Ph) | 487.64 |
| 105. | CH | Me | H | Me | 2,4,6-triMe-Ph | (CH2)3-NH-CH2-(4-OMe-Ph) | 457.61 |
| 106. | CH | nPr | H | Me | 2,4,6-triMe-Ph | CH2-CHMe-NH-(1-(pyrimidin-2-yl)-piperidin-4-yl) | 526.73 |
| 107. | CH | Et | H | Me | 2,4,6-triMe-Ph | CH2-CHMe-NH-(1-Ac-piperidin-4-yl) | 476.7 |
| 108. | CH | Et | H | Me | 2,4,6-triMe-Ph | CH2-CHMe-NH-(1,2,3,4-tetrahydro-naphthalen-2-yl) | 481.7 |
| 109. | CH | Et | H | Me | 2,4,6-triMe-Ph | CH2-CHMe-NH-CHMe-Ph | 455.65 |
| 110. | CH | Me | H | Me | 2,4,6-triMe-Ph | CHiBu-CH2-NH-(tetrahydropyran-4-yl) | 463.7 |
| 111. | CH | Me | H | Me | 2,6-diCl-4-(2-oxo-oxazolidin-3-yl)-Ph | (CH2)2-NH-(tetrahydropyran-4-yl) | 519.4 |
| 112. | CH | Me | H | Me | 2,6-diCl-4-(3,5-dimethyl-isoxazol-4-yl)-Ph | (CH2)2-NH-(tetrahydropyran-4-yl) | 529.47 |
| 113. | CH | Me | H | Me | 2,6-diCl-4-(4,5-dihydro-oxazol-2-yl)-Ph | (CH2)2-NH-(tetrahydropyran-4-yl) | 503.4 |
| 114. | CH | Me | H | Me | 2,6-diCl-4-(4H-[1,2,4]triazol-3-yl) | (CH2)2-NH-(tetrahydropyran-4-yl) | 502.41 |
| 115. | CH | Me | H | Me | 2,6-diCl-4-(C=O)-1'-pyrrolidine)-Ph | (CH2)2-NH-(tetrahydropyran-4-yl) | 531.49 |
| 116. | CH | Me | H | Me | 2,6-diCl-4-(C=O)—N-Et)-Ph | (CH2)2-NH-(tetrahydropyran-4-yl) | 505.45 |
| 117. | CH | Me | H | Me | 2,6-diCl-4-(CH(OH)Me2) | (CH2)2-NH-(tetrahydropyran-4-yl) | 492.45 |
| 118. | CH | Me | H | Me | 2,6-diCl-4-(CH2OH)-Ph | (CH2)2-NH-(tetrahydropyran-4-yl) | 464.40 |
| 119. | CH | Me | H | Me | 2,6-diCl-4-(CO2Me)-Ph | (CH2)2-NH-(tetrahydropyran-4-yl) | 492.41 |
| 120. | CH | Me | H | Me | 2,6-diCl-4-(COOEt)-Ph | (CH2)2-NH-(tetrahydropyran-4-yl) | 506.44 |
| 121. | CH | Me | H | Me | 2,6-diCl-4-(COOH)-Ph | (CH2)2-NH-(tetrahydropyran-4-yl) | 478.38 |
| 122. | CH | Me | H | Me | 2,6-diCl-4-(cPent-1-ene)-Ph | (CH2)2-NH-(tetrahydropyran-4-yl) | 500.48 |
| 123. | CH | Me | H | Me | 2,6-diCl-4-(isopropene)-Ph | (CH2)2-NH-(tetrahydropyran-4-yl) | 474.44 |
| 124. | CH | Me | H | Me | 2,6-diCl-4-(O(CH2)2-NMe2)-Ph | (CH2)2-NH-(tetrahydropyran-4-yl) | 521.5 |
| 125. | CH | Me | H | Me | 2,6-diCl-4-CH2OMe-Ph | (CH2)2-NH-(tetrahydropyran-4-yl) | 478.4 |
| 126. | CH | Me | H | Me | 2,6-diCl-4-CHO-Ph | (CH2)2-NH-(tetrahydropyran-4-yl) | 477.40 |
| 127. | CH | Me | H | Me | 2,6-diCl-4-CN-Ph | (CH2)2-NH-(1-(pyrimidin-2-yl)-piperidin-4-yl) | 536.5 |
| 128. | CH | Me | H | Me | 2,6-diCl-4-CN-Ph | (CH2)2-NH-(1-(SO2-N-(Me)2)-piperidin-4-yl) | 565.53 |
| 129. | CH | Me | H | Me | 2,6-diCl-4-Cn-Ph | (CH2)2-NH-(1-Bn-piperidin-4-yl) | 548.52 |
| 130. | CH | Me | H | Me | 2,6-diCl-4-CN-Ph | (CH2)2-NH-(1-propanoyl-piperidin-4-yl) | 514.46 |
| 131. | CH | Me | H | Me | 2,6-diCl-4-CN-Ph | (CH2)2-NH-(1-SO2Me-piperidin-4-yl) | 536.5 |
| 132. | CH | Me | H | Me | 2,6-diCl-4-CN-Ph | (CH2)2-NH-(tetrahydropyran-4-yl) | 459.38 |
| 133. | CH | Me | H | Me | 2,6-diCl-4-Et-Ph | (CH2)2-NH-(tetrahydropyran-4-yl) | 462.42 |
| 134. | CH | Me | H | Me | 2,6-diCl-4-ethynyl-Ph | (CH2)2-NH-(tetrahydropyran-4-yl) | 458.4 |

-continued

Table of Additional Examples

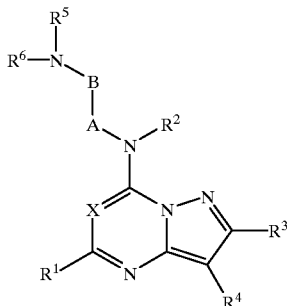

| EX | X | R¹ | R² | R³ | R⁴ | A-B-N[R⁶]-R⁵ | MW |
|---|---|---|---|---|---|---|---|
| 135. | CH | Me | H | Me | 2,6-diCl-4-ethynyl-Ph | CH2-CHMe-NH-(1-(pyrimidin-2-yl)-piperidin-4-yl) | 535.5 |
| 136. | CH | Me | H | Me | 2,6-diCl-4-OEt-Ph | (CH2)2-NH-(1-(pyrimidin-2-yl)-piperidin-4-yl) | 555.22 |
| 137. | N | Me | H | Me | 2,6-diCl-4-OEt-Ph | (CH2)2-NH-(1-(pyrimidin-2-yl)-piperidin-4-yl) | 556.5 |
| 138. | CH | Me | H | Me | 2,6-diCl-4-OEt-Ph | (CH2)2-NH-(1-Ac-piperidin-4-yl) | 519.5 |
| 139. | N | Me | H | Me | 2,6-diCl-4-OEt-Ph | (CH2)2-NH-(1-Ac-piperidin-4-yl) | 520.5 |
| 140. | CH | Me | H | Me | 2,6-diCl-4-OEt-Ph | (CH2)2-NH-(1-benzoyl-piperidin-4-yl) | 567.6 |
| 141. | N | Me | H | Me | 2,6-diCl-4-OEt-Ph | (CH2)2-NH-(1-COOEt-piperidin-4-yl) | 550.5 |
| 142. | CH | Me | H | Me | 2,6-diCl-4-OEt-Ph | (CH2)2-NH-(1-propanoyl-piperidin-4-yl) | 533.5 |
| 143. | CH | Me | H | Me | 2,6-diCl-4-OEt-Ph | (CH2)2-NH-(1-SO2Me-piperidin-4-yl) | 555.5 |
| 144. | N | Me | H | Me | 2,6-diCl-4-OEt-Ph | (CH2)2-NH-(1-SO2Me-piperidin-4-yl) | 556.5 |
| 145. | CH | Me | H | Me | 2,6-diCl-4-OEt-Ph | (CH2)2-NH-(1-SO2Me-piperidin-4-yl) | 555.52 |
| 146. | CH | Me | H | Me | 2,6-diCl-4-OEt-Ph | (CH2)2-NH-(1-SO2NMe2-piperidin-4-yl) | 584.6 |
| 147. | N | Me | H | Me | 2,6-diCl-4-OEt-Ph | (CH2)2-NH-(1-tBoc-piperidin-4-yl) | 578.53 |
| 148. | CH | Me | H | Me | 2,6-diCl-4-OEt-Ph | (CH2)2-NH-(2-Me-tetrahydro-furan-3-yl) | 478.43 |
| 149. | CH | Me | H | Me | 2,6-diCl-4-OEt-Ph | (CH2)2-NH-(2-OEt-cHex) | 520.51 |
| 150. | CH | Me | H | Me | 2,6-diCl-4-OEt-Ph | (CH2)2-NH-(2-OH-cHex) | 492.45 |
| 151. | CH | Me | H | Me | 2,6-diCl-4-OEt-Ph | (CH2)2-NH-(2-oxo-pyrrolidin-4-yl) | 447.4 |
| 152. | N | Me | H | Me | 2,6-diCl-4-OEt-Ph | (CH2)2-NH-(2F-cPent) | 481.40 |
| 153. | CH | Me | H | Me | 2,6-diCl-4-OEt-Ph | (CH2)2-NH-(4-COOEt-cHex) | 548.52 |
| 154. | CH | Me | H | Me | 2,6-diCl-4-OEt-Ph | (CH2)2-NH-(4-ethyleneketal-cHex) | 534.5 |
| 155. | N | Me | H | Me | 2,6-diCl-4-OEt-Ph | (CH2)2-NH-(4-ethyleneketal-cHex) | 535.47 |
| 156. | N | Me | H | Me | 2,6-diCl-4-OEt-Ph | (CH2)2-NH-(4-NHSO2Me-cHex) | 570.5 |
| 157. | CH | Me | H | Me | 2,6-diCl-4-OEt-Ph | (CH2)2-NH-(4-OH-cHex) | 492.5 |
| 158. | N | Me | H | Me | 2,6-diCl-4-OEt-Ph | (CH2)2-NH-(4-OH-cHex) | 493.43 |
| 159. | CH | Me | H | Me | 2,6-diCl-4-OEt-Ph | (CH2)2-NH-(4-oxo-cHex) | 490.5 |
| 160. | N | Me | H | Me | 2,6-diCl-4-OEt-Ph | (CH2)2-NH-(4-oxo-cHex) | 491.41 |
| 161. | CH | Me | H | Me | 2,6-diCl-4-OEt-Ph | (CH2)2-NH-(4,4-Me2-lacton-3-yl) | 506.4 |
| 162. | CH | Me | H | Me | 2,6-diCl-4-OEt-Ph | (CH2)2-NH-(6-azabicyclo[4.4.0]dec-3-yl) | 531.53 |
| 163. | CH | Me | H | Me | 2,6-diCl-4-OEt-Ph | (CH2)2-NH-(7-oxo-azepan-3-yl) | 505.45 |
| 164. | N | Me | H | Me | 2,6-diCl-4-OEt-Ph | (CH2)2-NH-(CH2)2-OH | 439.3 |
| 165. | N | Me | H | Me | 2,6-diCl-4-OEt-Ph | (CH2)2-NH-(CH2)3-OH | 453.4 |
| 166. | N | Me | H | Me | 2,6-diCl-4-OEt-Ph | (CH2)2-NH-(CH2)3-OMe | 467.4 |
| 167. | N | Me | H | Me | 2,6-diCl-4-OEt-Ph | (CH2)2-NH-(CH2)-(R)-CHMe-OH | 453.4 |
| 168. | N | Me | H | Me | 2,6-diCl-4-OEt-Ph | (CH2)2-NH-(S)-CHMe-CH2-OH | 453.4 |
| 169. | CH | Me | H | Me | 2,6-diCl-4-OEt-Ph | (CH2)2-NH-(tetrahydropyran-4-yl) | 478.4 |
| 170. | CH | Et | H | Me | 2,6-diCl-4-OEt-Ph | (CH2)2-NH-(tetrahydropyran-4-yl) | 492.5 |
| 171. | N | Me | H | Me | 2,6-diCl-4-OEt-Ph | (CH2)2-NH-(tetrahydropyran-4-yl) | 479.4 |
| 172. | N | Me | H | Me | 2,6-diCl-4-OEt-Ph | (CH2)2-NH-(trans-4-COOEt-cHex) | 549.49 |
| 173. | N | Me | H | Me | 2,6-diCl-4-OEt-Ph | (CH2)2-NH-(trans-4-OH-piperidin-4-yl) | 493.4 |
| 174. | CH | Me | H | Me | 2,6-diCl-4-OEt-Ph | (CH2)2-NH-CH2-(1-tBoc-piperidin-4-yl) | 591.59 |
| 175. | CH | Me | H | Me | 2,6-diCl-4-OEt-Ph | (CH2)2-NH-CH2-(piperidin-4-yl) | 491.47 |
| 176. | CH | Me | H | Me | 2,6-diCl-4-OEt-Ph | (CH2)2-NH-CH2-CF3 | 476.33 |
| 177. | CH | Me | H | Me | 2,6-diCl-4-OEt-Ph | (CH2)2-NH-CH2-CHOH-CH2OH | 468.39 |
| 178. | CH | Me | H | Me | 2,6-diCl-4-OEt-Ph | (CH2)2-NH-CHMe-(1-Ac-piperidin-4-yl) | 547.5 |
| 179. | CH | Me | H | Me | 2,6-diCl-4-OEt-Ph | (CH2)2-NH-CHMe-(1-tBoc-piperidin-4-yl) | 605.61 |
| 180. | CH | Me | H | Me | 2,6-diCl-4-OEt-Ph | (CH2)2-NH-CHMe-(piperidin-4-yl) | 505.49 |
| 181. | CH | Me | H | Me | 2,6-diCl-4-OEt-Ph | (CH2)2-NH-cyclohex-3-enyl | 475.4 |
| 182. | CH | Me | H | Me | 2,6-diCl-4-OEt-Ph | (CH2)2-NH-cyclohex-3-enyl | 474.4 |
| 183. | CH | Me | H | Me | 2,6-diCl-4-OEt-Ph | (CH2)2-NH-cyclohexan-4-oxime | 505.5 |
| 184. | N | Me | H | Me | 2,6-diCl-4-OEt-Ph | (CH2)2-NH-piperidin-4-yl | 480.43 |
| 185. | CH | Me | H | Me | 2,6-diCl-4-OEt-Ph | CH2-CHMe-NH-(1-(pyrimidin-2-yl)-piperidin-4-yl) | 569.54 |
| 186. | CH | Me | H | Me | 2,6-diCl-4-OEt-Ph | CH2-CHMe-NH-(4-ethyleneketal-cHex) | 548.52 |
| 187. | CH | Me | H | Me | 2,6-diCl-4-OEt-Ph | CH2-CHMe-NH-(4-OH-cHex) | 506.48 |
| 188. | CH | Me | H | Me | 2,6-diCl-4-OEt-Ph | CH2-CHMe-NH-(tetrahydropyran-4-yl) | 492.45 |
| 189. | CH | Me | H | Me | 2,6-diCl-4-OEt-Ph | CH2-CMe2-NH-(tetrahydropyran-4-yl) | 506.48 |
| 190. | CH | Me | H | Me | 2,6-diCl-4-OEt-Ph | CHMe-CH2-NH-(tetrahydropyran-4-yl) | 492.45 |
| 191. | CH | Me | H | Me | 2,6-diCl-4-OH-Ph | (CH2)2-NH-(1-Bn-piperidin-4-yl) | 539.51 |
| 192. | CH | Me | H | Me | 2,6-diCl-4-OH-Ph | (CH2)2-NH-(1-Ph-pyrrolidin-3-yl) | 511.46 |
| 193. | CH | Me | H | Me | 2,6-diCl-4-OH-Ph | (CH2)2-NH-(4-ethyleneketal-cHex) | 506.44 |

-continued

Table of Additional Examples

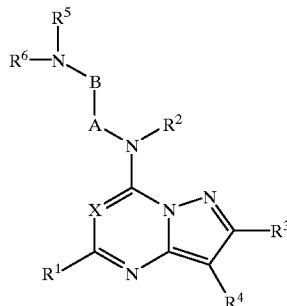

| EX | X | R¹ | R² | R³ | R⁴ | A-B-N[R⁶]-R⁵ | MW |
|---|---|---|---|---|---|---|---|
| 194. | CH | Me | H | Me | 2,6-diCl-4-OH-Ph | (CH2)2-NH-(4-oxo-cHex) | 462.38 |
| 195. | CH | Me | H | Me | 2,6-diCl-4-OH-Ph | (CH2)2-NH-(6-azabicyclo[4.4.0]dec-3-yl) | 503.48 |
| 196. | CH | Me | H | Me | 2,6-diCl-4-OH-Ph | (CH2)2-NH-(tetrahydropyran-4-yl) | 450.4 |
| 197. | CH | Et | H | Me | 2,6-diCl-4-OH-Ph | (CH2)2-NH-(tetrahydropyran-4-yl) | 464.4 |
| 198. | CH | Me | H | Me | 2,6-diCl-4-OH-Ph | (CH2)2-NH-CHMe-CH2-(3-OMe-4-OEt-Ph) | 530.46 |
| 199. | CH | Me | H | Me | 2,6-diCl-4-OH-Ph | (CH2)2-NH-CHMe-CH2-NMe2 | 451.4 |
| 200. | CH | Me | H | Me | 2,6-diCl-4-OH-Ph | CH2-CHMe-NH-(4-(1-morpholino)-cHex) | 547.53 |
| 201. | CH | Me | H | Me | 2,6-diCl-4-OH-Ph | CH2-CHMe-NH-(tetrahydropyran-4-yl) | 464.4 |
| 202. | CH | Me | H | Me | 2,6-diCl-4-OH-Ph | CHMe-CHMe-NH-(tetrahydropyran-4-yl) | 478.43 |
| 203. | CH | Me | H | Me | 2,6-diCl-4-OiPr-Ph | (CH2)2-NH-(tetrahydropyran-4-yl) | 492.45 |
| 204. | CH | Me | H | Me | 2,6-diCl-4-OMe-Ph | 2-(NH-(1-Bn-piperidin-4-yl))-cHex | 607.63 |
| 205. | CH | Me | H | Me | 2,6-diCl-4-OMe-Ph | 2-(NH-(1-Bn-piperidin-4-yl))-cHex | 607.63 |
| 206. | CH | Me | H | Me | 2,6-diCl-4-OMe-Ph | 2-(NH-(tetrahydropyran-4-yl))-cHex | 518.49 |
| 207. | CH | Me | H | Me | 2,6-diCl-4-OMe-Ph | 2-(NH-(tetrahydropyran-4-yl))-cHex | 518.49 |
| 208. | CH | Me | H | Me | 2,6-diCl-4-OMe-Ph | 3-(NH-(1-Bn-piperidin-4-yl))-cHex | 607.63 |
| 209. | CH | Me | H | Me | 2,6-diCl-4-OMe-Ph | 3-(NH-(tetrahydropyran-4-yl))-cHex | 518.49 |
| 210. | CH | Me | H | Me | 2,6-diCl-4-OMe-Ph | 4-(NH-(tetrahydropyran-4-yl))-cHex | 518.49 |
| 211. | CH | Me | H | Me | 2,6-diCl-4-OMe-Ph | (CH2)2-CHEt-NH-(1-Bn-piperidin-4-yl) | 595.62 |
| 212. | CH | Me | H | Me | 2,6-diCl-4-OMe-Ph | (CH2)2-CHEt-NH-(tetrahydropyran-4-yl) | 506.48 |
| 213. | CH | iPr | H | Me | 2,6-diCl-4-OMe-Ph | (CH2)2-CHEt-NH-(tetrahydropyran-4-yl) | 534.5 |
| 214. | CH | Me | H | Me | 2,6-diCl-4-OMe-Ph | (CH2)2-N((CH2)3-CF3)2 | 600.44 |
| 215. | CH | Me | H | Me | 2,6-diCl-4-OMe-Ph | (CH2)2-N(CH2-2-(CH2OH)-furan-5-yl)2 | 600.51 |
| 216. | CH | Me | H | Me | 2,6-diCl-4-OMe-Ph | (CH2)2-N[CH2-2-pyridyl]-(1-(CH2-2-pyridyl)-piperidin-4-yl) | 645.64 |
| 217. | CH | Me | H | Me | 2,6-diCl-4-OMe-Ph | (CH2)2-N[CH2-3-pyridyl]-(1-(CH2-3-pyridyl)-piperidin-4-yl) | 645.64 |
| 218. | CH | Me | H | Me | 2,6-diCl-4-OMe-Ph | (CH2)2-N(CH2-CHOH-CH2OH)2 | 528.44 |
| 219. | CH | Me | H | Me | 2,6-diCl-4-OMe-Ph | (CH2)2-N-propanoyl-(1-propanoyl-piperidin-4-yl) | 575.54 |
| 220. | CH | Me | H | Me | 2,6-diCl-4-OMe-Ph | (CH2)2-NEt-(tetrahydropyran-4-yl) | 492.45 |
| 221. | CH | Me | H | Me | 2,6-diCl-4-OMe-Ph | (CH2)2-NH-(1-(CH2-2-pyridyl)-piperidin-4-yl) | 554.53 |
| 222. | CH | Me | H | Me | 2,6-diCl-4-OMe-Ph | (CH2)2-NH-(1-(CH2-3-pyridyl)-piperidin-4-yl) | 554.53 |
| 223. | CH | Me | H | Me | 2,6-diCl-4-OMe-Ph | (CH2)2-NH-(1-(CH2-4-pyridyl)-piperidin-4-yl) | 554.53 |
| 224. | CH | Me | H | Me | 2,6-diCl-4-OMe-Ph | (CH2)2-NH-(1-(pyrimidin-2-yl)-piperidin-4-yl) | 541.5 |
| 225. | CH | Et | H | Me | 2,6-diCl-4-OMe-Ph | (CH2)2-NH-(1-(pyrimidin-2-yl)-piperidin-4-yl) | 555.52 |
| 226. | CH | Me | H | Me | 2,6-diCl-4-OMe-Ph | (CH2)2-NH-(1-Ac-piperidin-4-yl) | 504.46 |
| 227. | CH | Me | Me | Me | 2,6-diCl-4-OMe-Ph | (CH2)2-NH-(1-Ac-piperidin-4-yl) | 519.5 |
| 228. | CH | Me | H | Me | 2,6-diCl-4-OMe-Ph | (CH2)2-NH-(1-Bn-piperidin-4-yl) | 553.5 |
| 229. | CH | Me | H | Me | 2,6-diCl-4-OMe-Ph | (CH2)2-NH-(1-Et-piperidin-3-yl) | 491.5 |
| 230. | CH | Me | H | Me | 2,6-diCl-4-OMe-Ph | (CH2)2-NH-(1-Et-piperidin-4-yl) | 491.5 |
| 231. | CH | Me | H | Me | 2,6-diCl-4-OMe-Ph | (CH2)2-NH-(1-iPr-piperidin-4-yl) | 505.5 |
| 232. | CH | Me | H | Me | 2,6-diCl-4-OMe-Ph | (CH2)2-NH-(1-Me-piperidin-4-yl) | 477.44 |
| 233. | CH | Me | H | Me | 2,6-diCl-4-OMe-Ph | (CH2)2-NH-(1-Ph-pyrrolidin-3-yl) | 525.49 |
| 234. | CH | Me | H | Me | 2,6-diCl-4-OMe-Ph | (CH2)2-NH-((1-phenylethyl)-pyrrolidin-2-one-4-yl) | 567.52 |
| 235. | CH | Me | H | Me | 2,6-diCl-4-OMe-Ph | (CH2)2-NH-(1-phenylethyl-piperidin-4-yl) | 567.57 |
| 236. | CH | Me | H | Me | 2,6-diCl-4-OMe-Ph | (CH2)2-NH-(1-propanoyl-piperidin-4-yl) | 519.5 |
| 237. | CH | Me | H | Me | 2,6-diCl-4-OMe-Ph | (CH2)2-NH-(1-SO2Me-piperidin-4-yl) | 541.5 |
| 238. | CH | Me | H | Me | 2,6-diCl-4-OMe-Ph | (CH2)2-NH-(1-SO2NMe2-piperidin-4-yl) | 570.5 |
| 239. | CH | Et | H | Me | 2,6-diCl-4-OMe-Ph | (CH2)2-NH-(1,2,3,4-tetrahydro-naphthalen-2-yl) | 524.5 |
| 240. | CH | Me | H | Me | 2,6-diCl-4-OMe-Ph | (CH2)2-NH-(2-CF3-cHex) | 530.4 |
| 241. | CH | Me | H | Me | 2,6-diCl-4-OMe-Ph | (CH2)2-NH-(2-Me-tetrahydrofuran-3-yl) | 464.40 |
| 242. | CH | Me | H | Me | 2,6-diCl-4-OMe-Ph | (CH2)2-NH-(2-oxo-pyrrolidin-4-yl) | 463.37 |
| 243. | CH | Me | H | Me | 2,6-diCl-4-OMe-Ph | (CH2)2-NH-((2,2,6,6-tetramethyl)-piperidin-4-yl) | 519.5 |
| 244. | CH | Me | H | Me | 2,6-diCl-4-OMe-Ph | (CH2)2-NH-(2F-cHex) | 480.4 |
| 245. | CH | Me | H | Me | 2,6-diCl-4-OMe-Ph | (CH2)2-NH-(4-(1-azetidino)-cHex) | 517.51 |
| 246. | CH | Me | H | Me | 2,6-diCl-4-OMe-Ph | (CH2)2-NH-(4-(1-morpholino)-cHex) | 547.53 |
| 247. | CH | Me | H | Me | 2,6-diCl-4-OMe-Ph | (CH2)2-NH-(4-(1-piperidino)-cHex) | 545.56 |
| 248. | CH | Me | H | Me | 2,6-diCl-4-OMe-Ph | (CH2)2-NH-(4-(1-pyrrolidino)-cHex) | 531.53 |
| 249. | CH | Me | H | Me | 2,6-diCl-4-OMe-Ph | (CH2)2-NH-(4-(NH-CH2-2-pyridyl)-cHex) | 568.55 |
| 250. | CH | Me | H | Me | 2,6-diCl-4-OMe-Ph | (CH2)2-NH-(4-(NH-CH2-CH2-CH2OH)-cHex) | 521.49 |
| 251. | CH | Me | H | Me | 2,6-diCl-4-OMe-Ph | (CH2)2-NH-(4-(NH2)-cHex) | 477.44 |
| 252. | CH | Me | H | Me | 2,6-diCl-4-OMe-Ph | (CH2)2-NH-(4-(NHAc)-cHex) | 519.48 |

-continued

Table of Additional Examples

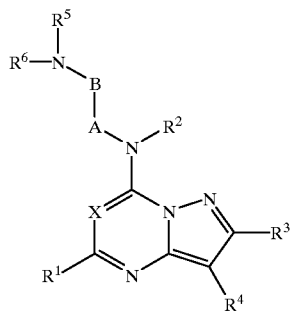

| EX | X | R¹ | R² | R³ | R⁴ | A-B-N[R⁶]-R⁵ | MW |
|---|---|---|---|---|---|---|---|
| 253. | CH | Me | H | Me | 2,6-diCl-4-OMe-Ph | (CH2)2-NH-(4-(NHSO2Me)-cHex) | 555.53 |
| 254. | CH | Me | H | Me | 2,6-diCl-4-OMe-Ph | (CH2)2-NH-(4-CF3-cHex) | 530.42 |
| 255. | CH | Me | H | Me | 2,6-diCl-4-OMe-Ph | (CH2)2-NH-(4-CF3-cHex) | 530.4 |
| 256. | CH | iPr | H | Me | 2,6-diCl-4-OMe-Ph | (CH2)2-NH-(4-CF3-cHex) | 558.5 |
| 257. | CH | Et | H | Me | 2,6-diCl-4-OMe-Ph | (CH2)2-NH-(4-CF3-cHex) | 544 5 |
| 258. | CH | Me | H | Me | 2,6-diCl-4-OMe-Ph | (CH2)2-NH-(4-ethyleneketal-cHex) | 520.5 |
| 259. | CH | Me | H | Me | 2,6-diCl-4-OMe-Ph | (CH2)2-NH-(4-hydroxyimino-cHex) | 491.42 |
| 260. | CH | Me | H | Me | 2,6-diCl-4-OMe-Ph | (CH2)2-NH-(4-NHCOOMe-cHex) | 535.5 |
| 261. | CH | Me | H | Me | 2,6-diCl-4-OMe-Ph | (CH2)2-NH-(4-NHEt-cHex) | 505.50 |
| 262. | CH | Me | H | Me | 2,6-diCl-4-OMe-Ph | (CH2)2-NH-(4-NHiBu-cHex) | 533.55 |
| 263. | CH | Me | H | Me | 2,6-diCl-4-OMe-Ph | (CH2)2-NH-(4-NHMe-cHex) | 491.47 |
| 264. | CH | Me | H | Me | 2,6-diCl-4-OMe-Ph | (CH2)2-NH-(4-NHpropanoyl-cHex) | 533.5 |
| 265. | CH | Me | H | Me | 2,6-diCl-4-OMe-Ph | (CH2)2-NH-(4-OH-cHex) | 478.43 |
| 266. | CH | Et | H | Me | 2,6-diCl-4-OMe-Ph | (CH2)2-NH-(4,4-Dimethyl-2-oxo-tetrahydro-furan-3-yl) | 506.44 |
| 267. | CH | Me | H | Me | 2,6-diCl-4-OMe-Ph | (CH2)2-NH-(5-Cl-indan-1-yl) | 530.89 |
| 268. | CH | Me | H | Me | 2,6-diCl-4-OMe-Ph | (CH2)2-NH-(5-fluorindolin-2-one-3-yl) | 529.41 |
| 269. | CH | Me | H | Me | 2,6-diCl-4-OMe-Ph | (CH2)2-NH-(6-azabicyclo[4.4.0]dec-3-yl) | 517.51 |
| 270. | CH | Me | H | Me | 2,6-diCl-4-OMe-Ph | (CH2)2-NH-(6-OMe-1,2,3,4-tetrahydro-naphthalen-1-yl) | 540.5 |
| 271. | CH | Me | H | Me | 2,6-diCl-4-OMe-Ph | (CH2)2-NH-(7-methoxyimino-azepan-3-yl | 520.47 |
| 272. | CH | Me | H | Me | 2,6-diCl-4-OMe-Ph | (CH2)2-NH-(CH2)2-CF3 | 476.3 |
| 273. | CH | Me | H | Me | 2,6-diCl-4-OMe-Ph | (CH2)2-NH-(CH2)2-OH | 424.33 |
| 274. | CH | Me | H | Me | 2,6-diCl-4-OMe-Ph | (CH2)2-NH-(CH2)3-CF3 | 490.336 |
| 275. | CH | Me | H | Me | 2,6-diCl-4-OMe-Ph | (CH2)2-NH-(cis-2F-cHex) | 480.4 |
| 276. | CH | Me | H | Me | 2,6-diCl-4-OMe-Ph | (CH2)2-NH-(cis-4-NHiBu-cHex) | 533.55 |
| 277. | CH | Me | H | Me | 2,6-diCl-4-OMe-Ph | (CH2)2-NH-(trans-4-OH-cHex)-#277a (CH2)2-NH-(cis-4OH-cHex)-#277b | 478.43 |
| 278. | CH | Me | H | Me | 2,6-diCl-4-OMe-Ph | (CH2)2-NH-(furan-2-one-4-yl) | 464.36 |
| 279. | CH | Me | H | Me | 2,6-diCl-4-OMe-Ph | (CH2)2-NH-(tetrahydropyran-4-yl) | 464.4 |
| 280. | CH | Et | H | Me | 2,6-diCl-4-OMe-Ph | (CH2)2-NH-(tetrahydropyran-4-yl) | 478.4 |
| 281. | CH | tBu | H | Me | 2,6-diCl-4-OMe-Ph | (CH2)2-NH-(tetrahydropyran-4-yl) | 506.5 |
| 282. | CH | nPr | H | Me | 2,6-diCl-4-OMe-Ph | (CH2)2-NH-(tetrahydropyran-4-yl) | 492.5 |
| 283. | CH | iPr | H | Me | 2,6-diCl-4-OMe-Ph | (CH2)2-NH-(tetrahydropyran-4-yl) | 492.5 |
| 284. | CH | CF3 | H | Me | 2,6-diCl-4-OMe-Ph | (CH2)2-NH-(tetrahydropyran-4-yl) | 518.4 |
| 285. | N | Me | H | Me | 2,6-diCl-4-OMe-Ph | (CH2)2-NH-(tetrahydropyran-4-yl) | 465.38 |
| 286. | CH | Me | H | Me | 2,6-diCl-4-OMe-Ph | (CH2)2-NH-(trans2F-cHex) | 480.4 |
| 287. | CH | Me | H | Me | 2,6-diCl-4-OMe-Ph | (CH2)2-NH-(trans-4-NHiBu-cHex) | 533.55 |
| 288. | CH | Me | H | Me | 2,6-diCl-4-OMe-Ph | (CH2)2-NH-(trans-4-OH-piperidin-4-yl) | 478.4 |
| 289. | CH | Me | H | Me | 2,6-diCl-4-OMe-Ph | (CH2)2-NH-Bn | 470.41 |
| 290. | CH | Me | H | Me | 2,6-diCl-4-OMe-Ph | (CH2)2-NH-CH-(CH2OH)2 | 454.36 |
| 291. | CH | Me | H | Me | 2,6-diCl-4-OMe-Ph | (CH2)2-NH-CH2-(1-tBoc-piperidin-4-yl) | 577.56 |
| 292. | CH | Me | H | Me | 2,6-diCl-4-OMe-Ph | (CH2)2-NH-CH2-(2-Me-oxetan-2-yl) | 464.4 |
| 293. | CH | Me | H | Me | 2,6-diCl-4-OMe-Ph | (CH2)2-NH-CH2-(piperidin-4-yl) | 477.44 |
| 294. | CH | Me | H | Me | 2,6-diCl-4-OMe-Ph | (CH2)2-NH-CH2-2-(CH2OH)-furan-5-yl | 490.39 |
| 295. | CH | Et | H | Me | 2,6-diCl-4-OMe-Ph | (CH2)2-NH-CH2-2-CF3-Ph | 552.43 |
| 296. | CH | Me | H | Me | 2,6-diCl-4-OMe-Ph | (CH2)2-NH-CH2-2-pyridyl | 471.39 |
| 297. | CH | Et | H | Me | 2,6-diCl-4-OMe-Ph | (CH2)2-NH-CH2-3-CF3-Ph | 552.43 |
| 298. | CH | Me | H | Me | 2,6-diCl-4-OMe-Ph | (CH2)2-NH-CH2-3-pyridyl | 471.39 |
| 299. | CH | Et | H | Me | 2,6-diCl-4-OMe-Ph | (CH2)2-NH-CH2-4-CF3-Ph | 552.43 |
| 300. | CH | Et | H | Me | 2,6-diCl-4-OMe-Ph | (CH2)2-NH-CH2-4-Cl-Ph | 518.88 |
| 301. | CH | Et | H | Me | 2,6-diCl-4-OMe-Ph | (CH2)2-NH-CH2-4-OCF3-Ph | 568.43 |
| 302. | CH | Et | H | Me | 2,6-diCl-4-OMe-Ph | (CH2)2-NH-CH2-4-OMe-Ph | 514.46 |
| 303. | CH | Me | H | Me | 2,6-diCl-4-OMe-Ph | (CH2)2-NH-CH2-4-pyridyl | 471.39 |
| 304. | CH | Me | H | Me | 2,6-diCl-4-OMe-Ph | (CH2)2-NH-CH2-CF3 | 462.31 |
| 305. | CH | Me | H | Me | 2,6-diCl-4-OMe-Ph | (CH2)2-NH-CH2-CHOH-CH2OH | 454.36 |
| 306. | CH | Me | H | Me | 2,6-diCl-4-OMe-Ph | (CH2)2-NH-CH2-CHOH-Me | 438.36 |
| 307. | CH | Me | H | Me | 2,6-diCl-4-OMe-Ph | (CH2)2-NH-CH2CHF2 | 444.3 |
| 308. | CH | Me | H | Me | 2,6-diCl-4-OMe-Ph | (CH2)2-NH-CH2CHFPh | 502.4 |
| 309. | CH | Me | H | Me | 2,6-diCl-4-OMe-Ph | (CH2)2-NH-CHEt-CH2OH | 452.39 |
| 310. | CH | Me | H | Me | 2,6-diCl-4-OMe-Ph | (CH2)2-NH-CHEt-Ph | 498.46 |

-continued

Table of Additional Examples

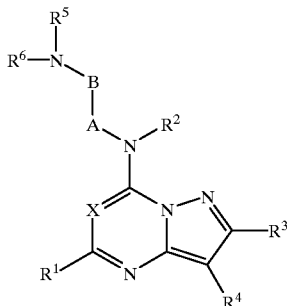

| EX | X | R¹ | R² | R³ | R⁴ | A-B-N[R⁶]-R⁵ | MW |
|---|---|---|---|---|---|---|---|
| 311. | CH | Et | H | Me | 2,6-diCl-4-OMe-Ph | (CH2)2-NH-CHEt-Ph | 512.49 |
| 312. | CH | nPr | H | Me | 2,6-diCl-4-OMe-Ph | (CH2)2-NH-CHEt-Ph | 526.51 |
| 313. | CH | Me | H | Me | 2,6-diCl-4-OMe-Ph | (CH2)2-NH-CHMe-(1-Et-piperidin-4-yl) | 533.51 |
| 314. | CH | Me | H | Me | 2,6-diCl-4-OMe-Ph | (CH2)2-NH-CHMe-(1-SO2Me-piperidin-4-yl) | 569.6 |
| 315. | CH | Me | H | Me | 2,6-diCl-4-OMe-Ph | (CH2)2-NH-CHMe-(1-tBoc-piperidin-4-yl) | 591.59 |
| 316. | CH | Me | H | Me | 2,6-diCl-4-OMe-Ph | (CH2)2-NH-CHMe-(CH2)3-NEt2 | 521.54 |
| 317. | CH | Me | H | Me | 2,6-diCl-4-OMe-Ph | (CH2)2-NH-CHMe-(piperidin-4-yl) | 491.47 |
| 318. | CH | Et | H | Me | 2,6-diCl-4-OMe-Ph | (CH2)2-NH-CHMe-4-Cl-Ph | 532.90 |
| 319. | CH | Et | H | Me | 2,6-diCl-4-OMe-Ph | (CH2)2-NH-CHMe-4-F-Ph | 516.45 |
| 320. | CH | Me | H | Me | 2,6-diCl-4-OMe-Ph | (CH2)2-NH-CHMe-CH2-F | 440.4 |
| 321. | CH | Me | H | Me | 2,6-diCl-4-OMe-Ph | (CH2)2-NH-CHMe-CH2-NEt2 | 493.48 |
| 322. | CH | Me | H | Me | 2,6-diCl-4-OMe-Ph | (CH2)2-NH-CHMe-CH2-NMe2 | 465.43 |
| 323. | CH | Me | H | Me | 2,6-diCl-4-OMe-Ph | (CH2)2-NH-CHMe-Ph | 484.43 |
| 324. | CH | Et | H | Me | 2,6-diCl-4-OMe-Ph | (CH2)2-NH-CHMe-Ph | 498.46 |
| 325. | CH | Me | H | Me | 2,6-diCl-4-OMe-Ph | (CH2)2-NH-CHMe-piperidin-4-yl | 477.44 |
| 326. | CH | Me | H | Me | 2,6-diCl-4-OMe-Ph | (CH2)2-NH-cyclohex-3-enyl | 460.4 |
| 327. | CH | nPr | H | Me | 2,6-diCl-4-OMe-Ph | (CH2)2-NH-cyclohex-3-enyl | 488.5 |
| 328. | CH | Et | H | Me | 2,6-diCl-4-OMe-Ph | (CH2)2-NH-cyclohex-3-enyl | 474.4 |
| 329. | CH | Me | Me | Me | 2,6-diCl-4-OMe-Ph | (CH2)2-NH-cyclohex-3-enyl | 474.4 |
| 330. | CH | Me | H | Me | 2,6-diCl-4-OMe-Ph | (CH2)2-NH-cyclopent-3-enyl | 446.38 |
| 331. | CH | Me | H | Me | 2,6-diCl-4-OMe-Ph | (CH2)2-NH-piperidin-4-yl | 463.41 |
| 332. | CH | Me | H | Me | 2,6-diCl-4-OMe-Ph | (CH2)2-NH-tropin-3-yl | 488.4 |
| 333. | CH | Me | Et | Me | 2,6-diCl-4-OMe-Ph | (CH2)2-NHEt | 436.39 |
| 334. | CH | Me | H | Me | 2,6-diCl-4-OMe-Ph | (CH2)2-NMe-(1-Ac-piperidin-4-yl) | 519.5 |
| 335. | CH | Me | Me | Me | 2,6-diCl-4-OMe-Ph | (CH2)2-NMe-(tetrahydropyran-4-yl) | 533.51 |
| 336. | CH | Me | H | Me | 2,6-diCl-4-OMe-Ph | (CH2)2-NMe-(tetrahydropyran-4-yl) | 478.4 |
| 337. | CH | Me | Me | Me | 2,6-diCl-4-OMe-Ph | (CH2)2-NMe-cyclohex-3-enyl | 488.5 |
| 338. | CH | Me | H | Me | 2,6-diCl-4-OMe-Ph | (CH2)2-NMe-cyclohex-3-enyl | 474.4 |
| 339. | CH | Me | H | Me | 2,6-diCl-4-OMe-Ph | (CH2)3-NH-(1-Bn-piperidin-4-yl) | 567.57 |
| 340. | CH | Me | H | Me | 2,6-diCl-4-OMe-Ph | (CH2)3-NH-tetrahydropyran-4-yl | 478.43 |
| 341. | CH | Me | H | Me | 2,6-diCl-4-OMe-Ph | (CH2)4-NH-(tetrahydropyran-4-yl) | 492.45 |
| 342. | CH | Me | H | Me | 2,6-diCl-4-OMe-Ph | CH2-(S)-pyrrolidin-2-yl | 420.34 |
| 343. | CH | Me | H | Me | 2,6-diCl-4-OMe-Ph | CH2-CH(CH2-imidazol-1-yl)-NH-(1-Bn-piperidin-4-yl) | 633.63 |
| 344. | CH | Me | H | Me | 2,6-diCl-4-OMe-Ph | CH2-CH(CH2-imidazol-1-yl)-NH-(tetrahydropyran-4-yl) | 544.49 |
| 345. | CH | Me | H | Me | 2,6-diCl-4-OMe-Ph | CH2-CHEt-NH-(1-Ac-piperidin-4-yl) | 533.5 |
| 346. | CH | Me | H | Me | 2,6-diCl-4-OMe-Ph | CH2-CHEt-NH-(tetrahydropyran-4-yl) | 492.5 |
| 347. | CH | Me | H | Me | 2,6-diCl-4-OMe-Ph | CH2-CHiBu-NH-(tetrahydropyran-4-yl) | 520.52 |
| 348. | CH | Me | H | Me | 2,6-diCl-4-OMe-Ph | CH2-CHiPr-NH-(tetrahydropyran-4-yl) | 506.5 |
| 349. | CH | iPr | H | Me | 2,6-diCl-4-OMe-Ph | CH2-CHMe-NH-(1-(pyrimidin-2-yl)-piperidin-4-yl) | 583.57 |
| 350. | CH | nPr | H | Me | 2,6-diCl-4-OMe-Ph | CH2-CHMe-NH-(1-(pyrimidin-2-yl)-piperidin-4-yl) | 583.57 |
| 351. | CH | Et | H | Me | 2,6-diCl-4-OMe-Ph | CH2-CHMe-NH-(1-(pyrimidin-2-yl)-piperidin-4-yl) | 569.54 |
| 352. | CH | Me | H | Me | 2,6-diCl-4-OMe-Ph | CH2-CHMe-NH-(4-(1-morpholino)-cHex) | 561.56 |
| 353. | CH | Me | H | Me | 2,6-diCl-4-OMe-Ph | CH2-CHMe-NH-(4-(1-morpholino)-cHex) | 575.59 |
| 354. | CH | Me | H | Me | 2,6-diCl-4-OMe-Ph | CH2-CHMe-NH-(4-ethyleneketal-cHex) | 534.49 |
| 355. | CH | Me | H | Me | 2,6-diCl-4-OMe-Ph | CH2-CHMe-NH-(4-NHMe-cHex) | 505.50 |
| 356. | CH | Me | H | Me | 2,6-diCl-4-OMe-Ph | CH2-CHMe-NH-(4-OH-cHex) | 492.45 |
| 357. | CH | Me | H | Me | 2,6-diCl-4-OMe-Ph | CH2-CHMe-NH-(4-oxo-cHex) | 490.44 |
| 358. | CH | Me | H | Me | 2,6-diCl-4-OMe-Ph | CH2-CHMe-NH-(tetrahydropyran-4-yl) | 478.4 |
| 359. | CH | Et | H | Me | 2,6-diCl-4-OMe-Ph | CH2-CHMe-NH-(tetrahydropyran-4-yl) | 492.5 |
| 360. | CH | iPr | H | Me | 2,6-diCl-4-OMe-Ph | CH2-CHMe-NH-(tetrahydropyran-4-yl) | 506.48 |
| 361. | CH | nPr | H | Me | 2,6-diCl-4-OMe-Ph | CH2-CHMe-NH-(tetrahydropyran-4-yl) | 506.5 |
| 362. | CH | Me | H | Me | 2,6-diCl-4-OMe-Ph | CH2-CHNH2-CH2-imidazol-1-yl | 460.37 |
| 363. | CH | Me | H | Me | 2,6-diCl-4-OMe-Ph | CH2-CHOH-CH2-NH-(1-Bn-piperidin-4-yl) | 583.57 |
| 364. | CH | Me | H | Me | 2,6-diCl-4-OMe-Ph | CH2-CHOH-CH2-NH-(tetrahydropyran-4-yl) | 494.43 |
| 365. | CH | Me | H | Me | 2,6-diCl-4-OMe-Ph | CH2-CHOH-CH2-NH2 | 410.31 |
| 366. | CH | Me | H | Me | 2,6-diCl-4-OMe-Ph | CH2-CMe2-CH2-NH-(1-Bn-piperidin-4-yl) | 595.62 |
| 367. | CH | Me | H | Me | 2,6-diCl-4-OMe-Ph | CH2-CMe2-CH2-NH-(tetrahydropyran-4-yl) | 506.48 |
| 368. | CH | Me | H | Me | 2,6-diCl-4-OMe-Ph | CH2-CMe2-NH-(1-Bn-piperidin-4-yl) | 581.59 |
| 369. | CH | Me | H | Me | 2,6-diCl-4-OMe-Ph | CH2-CMe2-NH-(tetrahydropyran-4-yl) | 492.45 |

-continued

Table of Additional Examples

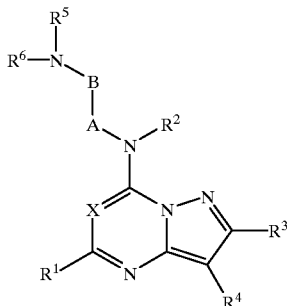

| EX | X | R¹ | R² | R³ | R⁴ | A-B-N[R⁶]-R⁵ | MW |
|---|---|---|---|---|---|---|---|
| 370. | CH | Me | Me | Me | 2,6-diCl-4-OMe-Ph | CH2-NH-(tetrahydropyran-4-yl) | 478.4 |
| 371. | CH | Me | H | Me | 2,6-diCl-4-OMe-Ph | CHEt-CH2-NH-(1-Ac-piperidin-4-yl) | 533.5 |
| 372. | CH | Me | H | Me | 2,6-diCl-4-OMe-Ph | CHEt-CH2-NH-(tetrahydropyran-4-yl) | 492.5 |
| 373. | CH | Me | H | Me | 2,6-diCl-4-OMe-Ph | CHiBu-CH2-NH-(tetrahydropyran-4-yl) | 520.52 |
| 374. | CH | Me | H | Me | 2,6-diCl-4-OMe-Ph | CHMe-CHMe-NH(1-COOEt-piperidin-4-yl) | 563.5 |
| 375. | CH | Me | H | Me | 2,6-diCl-4-OMe-Ph | CHMe-CHMe-NH-(tetrahydropyran-4-yl) | 492.45 |
| 376. | CH | Me | H | Me | 2,6-diCl-4-OMe-Ph | CHMe-CHMe-NH-(tetrahydropyran-4-yl) | 506.48 |
| 377. | CH | Et | H | Me | 2,6-diCl-4-OMe-Ph | CHMe-CHMe-NH-(tetrahydropyran-4-yl) | 506.5 |
| 378. | CH | Me | H | Me | 2,6-diCl-4-OMe-Ph | CMe2-CH2-NH-(1-(pyrimidin-2-yl)-piperidin-4-yl) | 569.5 |
| 379. | CH | Me | H | Me | 2,6-diCl-4-OMe-Ph | CMe2-CH2-NH-(tetrahydropyran-4-yl) | 492.5 |
| 380. | CH | Me | H | Me | 2,6-diCl-4-OMe-Ph | CMe2-CH2-NH-C(Me)2-CH2-OH | 480.4 |
| 381. | CH | Me | H | Me | 2,6-diCl-4-OMe-Ph | quinuclidin-3-yl | 446.38 |
| 382. | CH | Me | H | Me | 2,6-diCl-4-OPr-Ph | (CH2)2-NH-(tetrahydropyran-4-yl) | 492.45 |
| 383. | CH | Me | H | Me | 2,6-diCl-4-OSO2CF3-Ph | (CH2)2-NH-(tetrahydropyran-4-yl) | 582.43 |
| 384. | CH | Et | H | Me | 2,6-diCl-Ph | (CH2)2-NH-(1-(pyrimidin-2-yl)-piperidin-4-yl) | 525.5 |
| 385. | CH | iPr | H | Me | 2,6-diCl-Ph | (CH2)2-NH-(1-(pyrimidin-2-yl)-piperidin-4-yl) | 539.5 |
| 386. | CH | CF3 | H | Me | 2,6-diCl-Ph | (CH2)2-NH-(1-(pyrimidin-2-yl)-piperidin-4-yl) | 565.43 |
| 387. | CH | nPr | H | Me | 2,6-diCl-Ph | (CH2)2-NH-(1-(pyrimidin-2-yl)-piperidin-4-yl) | 539.5 |
| 388. | CH | Me | H | Me | 2,6-diCl-Ph | (CH2)2-NH-(1-benzoyl-piperidin-4-yl) | 646.88 |
| 389. | CH | Me | H | Me | 2,6-diCl-Ph | (CH2)2-NH-(1-Bn-piperidin-4-yl) | 523.51 |
| 390. | N | Me | H | Me | 2,6-diCl-Ph | (CH2)2-NH-(1-Bn-piperidin-4-yl) | 524.5 |
| 391. | CH | Me | H | Me | 2,6-diCl-Ph | (CH2)2-NH-(1-Bn-pyrrolidin-3-yl) | 509.49 |
| 392. | CH | Me | H | Me | 2,6-diCl-Ph | (CH2)2-NH-(1-Et-piperidin-3-yl) | 461.4 |
| 393. | CH | Me | H | Me | 2,6-diCl-Ph | (CH2)2-NH-(1-Et-piperidin-4-yl) | 534.36 |
| 394. | CH | Me | H | Me | 2,6-diCl-Ph | (CH2)2-NH-(1-Me-piperidin-4-yl) | 447.41 |
| 395. | CH | Me | H | Me | 2,6-diCl-Ph | (CH2)2-NH-(4-(1-azetidino)-cHex) | 487.5 |
| 396. | CH | Me | H | Me | 2,6-diCl-Ph | (CH2)2-NH-(4-(1-morpholino)-cHex) | 503.5 |
| 397. | CH | Me | H | Me | 2,6-diCl-Ph | (CH2)2-NH-(4-(1-piperidino)-cHex) | 515.5 |
| 398. | CH | Me | H | Me | 2,6-diCl-Ph | (CH2)2-NH-(4-(1-pyrrolidino)-cHex) | 647.35 |
| 399. | CH | Me | H | Me | 2,6-diCl-Ph | (CH2)2-NH-(4-(NH-(CH2)2-OH)-cHex) | 491.47 |
| 400. | CH | Me | H | Me | 2,6-diCl-Ph | (CH2)2-NH-(4-(NH-CH2-2-pyridyl)-cHex) | 538.53 |
| 401. | CH | Me | H | Me | 2,6-diCl-Ph | (CH2)2-NH-(4-(NH-iBu)-cHex) | 503.52 |
| 402. | CH | Me | H | Me | 2,6-diCl-Ph | (CH2)2-NH-(4-(NHEt)-cHex) | 460.4 |
| 403. | CH | Me | H | Me | 2,6-diCl-Ph | (CH2)2-NH--(4-(NHMe)-cHex) | 607.28 |
| 404. | CH | iPr | H | Me | 2,6-diCl-Ph | (CH2)2-NH-(4-CF3-cHex) | 528.5 |
| 405. | CH | Me | H | Me | 2,6-diCl-Ph | (CH2)2-NH-(4-ethyleneketal-cHex) | 490.44 |
| 406. | CH | Me | H | Me | 2,6-diCl-Ph | (CH2)2-NH-(4-OH-cHex) | 448.4 |
| 407. | CH | Me | H | Me | 2,6-diCl-Ph | (CH2)2-NH-(4-oxo-cHex) | 446.38 |
| 408. | N | Me | H | Me | 2,6-diCl-Ph | (CH2)2-NH-(4-trans-OH-cHex) | 449.4 |
| 409. | CH | Me | H | Me | 2,6-diCl-Ph | (CH2)2-NH-(6,7-diOMe-1,2,3,4-tetrahydronaphthalen-2-yl) | 540.5 |
| 410. | CH | Me | H | Me | 2,6-diCl-Ph | (CH2)2-NH-(8-aza-8-methylbicyclo[3.2.1]octan-3-yl) | 459.43 |
| 411. | CH | Me | H | Me | 2,6-diCl-Ph | (CH2)2-NH-(tetrahydropyran-4-yl) | 434.37 |
| 412. | CH | iPr | H | Me | 2,6-diCl-Ph | (CH2)2-NH-(tetrahydropyran-4-yl) | 462.4 |
| 413. | CH | CF3 | H | Me | 2,6-diCl-Ph | (CH2)2-NH-(tetrahydropyran-4-yl) | 488.34 |
| 414. | CH | CF3 | H | Me | 2,6-diCl-Ph | (CH2)2-NH-(trans-1-CF3-cyclohexan-4-yl) | 554.37 |
| 415. | CH | Me | H | Me | 2,6-diCl-Ph | (CH2)2-NH-2,2,6,6-tetramethylpiperidin-4-yl | 489.5 |
| 416. | CH | Me | H | Me | 2,6-diCl-Ph | (CH2)2-NH-CHMe-CH2-(3-OMe-4-(O-(CH2)2-NMe2)-Ph) | 585.6 |
| 417. | CH | Me | H | Me | 2,6-diCl-Ph | (CH2)2-NH-CHMe-CH2-(3-OMe-4-OH-Ph) | 514.46 |
| 418. | N | Me | H | Me | 2,6-diCl-Ph | (CH2)2-NH-cPent | 449.4 |
| 419. | CH | Me | H | Me | 2,6-diCl-Ph | (CH2)2-NH-piperidin-4-yl | 433.4 |
| 420. | CH | Me | H | Me | 2,6-diCl-Ph | (CH2)2-NH-quinolin-2-yl | 477.40 |
| 421. | CH | Me | H | Me | 2,6-diCl-Ph | (CH2)2-NH-quinuclidn-3-yl | 459.4 |
| 422. | CH | Me | H | Me | 2,6-diCl-Ph | CH2-CHEt-NH-(1-Ac-piperidin-4-yl) | 503.48 |
| 423. | CH | Me | H | Me | 2,6-diCl-Ph | CH2-CHEt-NH-(tetrahydropyran-4-yl) | 462.43 |
| 424. | CH | nPr | H | Me | 2,6-diCl-Ph | CH2-CHMe-NH-(1-(pyrimidin-2-yl)-piperidin-4-yl) | 553.5 |
| 425. | CH | Et | H | Me | 2,6-diCl-Ph | CH2-CHMe-NH-(1-(pyrimidin-2-yl)-piperidin-4-yl) | 539.5 |
| 426. | CH | Me | H | Me | 2,6-diCl-Ph | CH2-CHMe-NH-(1-Bn-piperidin-4-yl) | 537.53 |
| 427. | CH | Me | H | Me | 2,6-diCl-Ph | CH2-CHMe-NH-(tetrahydropyran-4-yl) | 448.4 |
| 428. | CH | Me | H | Me | 2,6-diCl-Ph | CHEt-CH2-NH-(tetrahydropyran-4-yl) | 462.4 |

-continued

Table of Additional Examples

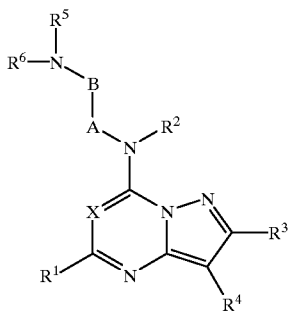

| EX | X | R¹ | R² | R³ | R⁴ | A-B-N[R⁶]-R⁵ | MW |
|---|---|---|---|---|---|---|---|
| 429. | CH | Me | H | Me | 2,6-diCl-Ph | CHEt-CH2-NH-(tetrahydropyran-4-yl) | 503.5 |
| 430. | CH | Me | H | Me | 2,6-diCl-Ph | CHMe-CHMe-NH-(1-Bn-piperidin-4-yl) | 551.57 |
| 431. | CH | Me | H | Me | 2,6-diCl-Ph | CHMe-CHMe-NH-(tetrahydropyran-4-yl) | 462.43 |
| 432. | CH | Me | H | Me | 2,6-diMe-3,5-diBr-4-OCF3-Ph | (CH2)2-NH-(tetrahydropyran-4-yl) | 634.6 |
| 433. | CH | Me | H | Me | 2,6-diMe-4-Cl-Ph | (CH2)2-NH-(1-(pyrimidin-2-yl)-piperidin-4-yl) | 505.06 |
| 434. | CH | Me | H | Me | 2,6-diMe-4-Cl-Ph | (CH2)2-NH-(1-Bn-piperidin-4-yl) | 517.12 |
| 435. | CH | Me | H | Me | 2,6-diMe-4-Cl-Ph | (CH2)2-NH-(1-COOEt-piperidin-4-yl) | 499.0 |
| 436. | CH | Me | H | Me | 2,6-diMe-4-Cl-Ph | (CH2)2-NH-(4-COOH-cHexl) | 470.01 |
| 437. | CH | Me | H | Me | 2,6-diMe-4-CN-Ph | (CH2)2-NH-(tetrahydropyran-4-yl) | 418.53 |
| 438. | CH | Me | H | Me | 2,6-diMe-4-OCF3-5-Br-Ph | (CH2)2-NH-(tetrahydropyran-4-yl) | 556.4 |
| 439. | CH | Me | H | Me | 2,6-diMe-4-OCF3-Ph | (CH2)2-NH-(1-(5-Et-pyrimidin-2-yl)-piperidin-4-yl) | 582.66 |
| 440. | CH | Me | H | Me | 2,6-diMe-4-OCF3-Ph | (CH2)2-NH-(1-(pyrimidin-2-yl)-piperidin-4-yl) | 554.61 |
| 441. | CH | Me | H | Me | 2,6-diMe-4-OCF3-Ph | (CH2)2-NH-(1-(pyrimidin-2-yl)-piperidin-4-yl) | 536.62 |
| 442. | CH | Me | H | Me | 2,6-diMe-4-OCF3-Ph | (CH2)2-NH-(2F-cPent) | 479.53 |
| 443. | CH | Me | H | Me | 2,6-diMe-4-OCF3-Ph | (CH2)2-NH-(tetrahydropyran-4-yl) | 477.52 |
| 444. | CH | Me | H | Me | 2,6-diMe-4-OCF3-Ph | (CH2)2-NH-(tetrahydropyran-4-yl) | 459.53 |
| 445. | CH | Me | H | Me | 2,6-diMe-4-OEt-Ph | (CH2)2-NH-(1-(2-Cl-pyrimidin-5-yl)-piperidin-4-yl) | 549.11 |
| 446. | CH | Me | H | Me | 2,6-diMe-4-OEt-Ph | (CH2)2-NH-(1-(2-F-pyridin-6-yl)-piperidin-4-yl) | 531.67 |
| 447. | CH | Me | H | Me | 2,6-diMe-4-OEt-Ph | (CH2)2-NH-(1-(2-OMe-pyridin-5-yl)-piperidin-4-yl) | 543.70 |
| 448. | CH | Me | H | Me | 2,6-diMe-4-OEt-Ph | (CH2)2-NH-(1-(3,6-diMe-pyrazin-2-yl)-piperidin-4-yl) | 542.72 |
| 449. | CH | Me | H | Me | 2,6-diMe-4-OEt-Ph | (CH2)2-NH-(1-(4-Me-pyridin-2-yl)-piperidin-4-yl) | 527.70 |
| 450. | CH | Me | H | Me | 2,6-diMe-4-OEt-Ph | (CH2)2-NH-(1-(4-OMe-pyrimidin-2-yl)-piperidin-4-yl) | 544.69 |
| 451. | CH | Me | H | Me | 2,6-diMe-4-OEt-Ph | (CH2)2-NH-(1-(5-CF3-pyridin-2-yl)-piperidin-4-yl) | 581.68 |
| 452. | CH | Me | H | Me | 2,6-diMe-4-OEt-Ph | (CH2)2-NH-(1-(5-F-pyrimidin-2-yl)-piperidin-4-yl) | 532.66 |
| 453. | CH | Me | H | Me | 2,6-diMe-4-OEt-Ph | (CH2)2-NH-(1-(6-Cl-pyridazin-3-yl)-piperidin-4-yl) | 549.11 |
| 454. | CH | Me | H | Me | 2,6-diMe-4-OEt-Ph | (CH2)2-NH-(1-(6-Me-pyridin-2-yl)-piperidin-4-yl) | 527.70 |
| 455. | CH | Me | H | Me | 2,6-diMe-4-OEt-Ph | (CH2)2-NH-(1-(6-OMe-pyridin-2-yl)-piperidin-4-yl) | 543.70 |
| 456. | CH | Me | H | Me | 2,6-diMe-4-OEt-Ph | (CH2)2-NH-(1-(pyridin-2-yl)-piperidin-4-yl) | 513.68 |
| 457. | CH | Me | H | Me | 2,6-diMe-4-OEt-Ph | (CH2)2-NH-(1-(pyrimidin-2-yl)-piperidin-4-yl) | 514.67 |
| 458. | CH | Me | H | Me | 2,6-diMe-4-OEt-Ph | (CH2)2-NH-(1-(pyrimidin-2-yl)-piperidin-4-yl) | 542.72 |
| 459. | CH | Me | H | Me | 2,6-diMe-4-OEt-Ph | (CH2)2-NH-(1-(pyrimidin-5-yl)-piperidin-4-yl) | 514.67 |
| 460. | CH | Me | H | Me | 2,6-diMe-4-OEt-Ph | (CH2)2-NH-(1-(thiazol-2-yl)-piperidin-4-yl) | 519.71 |
| 461. | CH | Me | H | Me | 2,6-diMe-4-OEt-Ph | (CH2)2-NH-(4-ethyleneketal-cHex) | 493.64 |
| 462. | CH | Me | H | Me | 2,6-diMe-4-OEt-Ph | (CH2)2-NH-(4-oxo-cHex) | 449.59 |
| 463. | CH | Me | H | Me | 2,6-diMe-4-OH-Ph | (CH2)2-NH-(1-(2-F-pyridin-6-yl)-piperidin-4-yl) | 503.61 |
| 464. | CH | Me | H | Me | 2,6-diMe-4-OMe-Ph | (CH2)2-NH-(1-(2-OMe-pyridin-6-yl)-piperidin-4-yl) | 529.68 |
| 465. | CH | Me | H | Me | 2,6-diMe-4-OMe-Ph | (CH2)2-NH-(1-(4-CF3-pyrimidin-2-yl)-piperidin-4-yl) | 568.64 |
| 466. | CH | Me | H | Me | 2,6-diMe-4-OMe-Ph | (CH2)2-NH-(1-(5-Et-pyrimidin-2-yl)-piperidin-4-yl) | 528.7 |
| 467. | CH | Me | H | Me | 2,6-diMe-4-OMe-Ph | (CH2)2-NH-(1-(5-F-pyrimidin-2-yl)-piperidin-4-yl) | 518.63 |
| 468. | CH | Me | H | Me | 2,6-diMe-4-OMe-Ph | (CH2)2-NH-(1-(6-F-2-pyridyl)-piperidin-4-yl) | 517.64 |
| 469. | CH | Me | H | Me | 2,6-diMe-4-OMe-Ph | (CH2)2-NH-(1-(pyrimidin-2-yl)-piperidin-4-yl) | 500.64 |
| 470. | CH | Me | H | Me | 2,6-diMe-4-OMe-Ph | (CH2)2-NH-(1-(pyrimidin-2-yl)-piperidin-4-yl) | 486.61 |
| 471. | N | Me | H | Me | 2,6-diMe-4-OMe-Ph | (CH2)2-NH-(1-(pyrimidin-2-yl)-piperidin-4-yl) | 501.63 |
| 472. | CH | Me | H | Me | 2,6-diMe-4-OMe-Ph | (CH2)2-NH-(1-(thiazol-2-yl)-piperidin-4-yl) | 505.68 |
| 473. | CH | Me | H | Me | 2,6-diMe-4-OMe-Ph | (CH2)2-NH-(1-Bn-piperidin-4-yl) | 512.7 |
| 474. | CH | Me | H | Me | 2,6-diMe-4-OMe-Ph | (CH2)2-NH-(1-COOEt-piperidin-4-yl) | 493.64 |
| 475. | CH | Me | H | Me | 2,6-diMe-4-OMe-Ph | (CH2)2-NH-(1-Et-piperidin-3-yl) | 450.62 |
| 476. | CH | Me | H | Me | 2,6-diMe-4-OMe-Ph | (CH2)2-NH-(1-Et-piperidin-4-yl) | 450.4 |
| 477. | CH | Me | H | Me | 2,6-diMe-4-OMe-Ph | (CH2)2-NH-(1-formyl-piperidin-4-yl) | 451.3 |
| 478. | CH | Me | H | Me | 2,6-diMe-4-OMe-Ph | (CH2)2-NH-(1-Me-piperidin-4-yl) | 436.4 |
| 479. | CH | Me | H | Me | 2,6-diMe-4-OMe-Ph | (CH2)2-NH-(1-SO2Me-piperidin-4-yl) | 500.66 |
| 480. | CH | Me | H | Me | 2,6-diMe-4-OMe-Ph | (CH2)2-NH-(2-Me-tetrahydrofuran-3-yl) | 423.55 |
| 481. | CH | Me | H | Me | 2,6-diMe-4-OMe-Ph | (CH2)2-NH-(2F-cPent) | 425.6 |
| 482. | CH | Me | H | Me | 2,6-diMe-4-OMe-Ph | (CH2)2-NH-(4-(1-morpholino)-cHex) | 520.71 |
| 483. | CH | Me | H | Me | 2,6-diMe-4-OMe-Ph | (CH2)2-NH-(4-(1-piperidino)-cHex) | 518.74 |
| 484. | CH | Me | H | Me | 2,6-diMe-4-OMe-Ph | (CH2)2-NH-(4-(1-pyrrolidino)-cHex) | 490.68 |
| 485. | CH | Me | H | Me | 2,6-diMe-4-OMe-Ph | (CH2)2-NH-(4-(1-pyrrolidino)-cHex) | 504.71 |
| 486. | CH | Me | H | Me | 2,6-diMe-4-OMe-Ph | (CH2)2-NH-(4-(NH-CH2-2-pyridyl)-cHex) | 541.73 |
| 487. | CH | Me | H | Me | 2,6-diMe-4-OMe-Ph | (CH2)2-NH-(4-(NH-CH2-4-pyridyl)-cHex) | 541.73 |

-continued

Table of Additional Examples

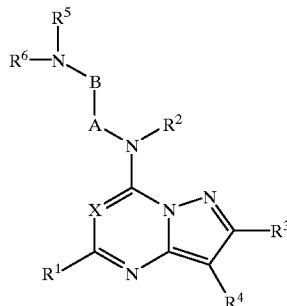

| EX | X | R¹ | R² | R³ | R⁴ | A-B-N[R⁶]-R⁵ | MW |
|---|---|---|---|---|---|---|---|
| 488. | CH | Me | H | Me | 2,6-diMe-4-OMe-Ph | (CH2)2-NH-(4-(NH-iBu)-cHex) | 492.70 |
| 489. | CH | Me | H | Me | 2,6-diMe-4-OMe-Ph | (CH2)2-NH-(4-(NiBu-NSO2-Me)-cHex) | 570.79 |
| 490. | CH | Me | H | Me | 2,6-diMe-4-OMe-Ph | (CH2)2-NH-(4-(NMe-NiBu)-cHex) | 506.73 |
| 491. | CH | Me | H | Me | 2,6-diMe-4-OMe-Ph | (CH2)2-NH-(4-ethyleneketal-cHex) | 479.61 |
| 492. | CH | Me | H | Me | 2,6-diMe-4-OMe-Ph | (CH2)2-NH-(4-NHiBu-cHex) | 506.73 |
| 493. | CH | Me | H | Me | 2,6-diMe-4-OMe-Ph | (CH2)2-NH-(4-NHSO2-Me-cHex) | 514.68 |
| 494. | CH | Me | H | Me | 2,6-diMe-4-OMe-Ph | (CH2)2-NH-(4-oxo-cHex) | 435.4 |
| 495. | CH | Me | H | Me | 2,6-diMe-4-OMe-Ph | (CH2)2-NH-(4,4-diMe-cHex) | 449.63 |
| 496. | CH | Me | H | Me | 2,6-diMe-4-OMe-Ph | (CH2)2-NH-(4,4-dioxo-tetrahydrothian-yl) | 471.62 |
| 497. | CH | Me | H | Me | 2,6-diMe-4-OMe-Ph | (CH2)2-NH-(tetrahydropyran-4-yl) | 439.63 |
| 498. | N | Me | H | Me | 2,6-diMe-4-OMe-Ph | (CH2)2-NH-(trans-4-COOEt-cHex) | 494.63 |
| 499. | CH | Me | H | Me | 2,6-diMe-4-OMe-Ph | (CH2)2-NH-(trans-4-COOEt-cHex) | 493.64 |
| 500. | CH | Me | H | Me | 2,6-diMe-4-OMe-Ph | (CH2)2-NH-(trans-4-COOH-cHex) | 465.59 |
| 501. | CH | Me | H | Me | 2,6-diMe-4-OMe-Ph | (CH2)2-NH-cyclohex-3-enyl | 419.57 |
| 502. | CH | Me | H | Me | 2,6-diMe-4-OMe-Ph | (CH2)2-NH-piperidin-4-yl | 422.5 |
| 503. | CH | Me | H | Me | 2,6-diMe-4-OMe-Ph | CH2-CHMe-NH-(1-(5-Et-pyrimidin-2-yl)-piperidin-4-yl) | 542.70 |
| 504. | CH | Me | H | Me | 2,6-diMe-4-OMe-Ph | CH2-CHMe-NH-(1-(pyrimidin-2-yl)-piperidin-4-yl) | 514.68 |
| 505. | CH | Me | H | Me | 2,6-diMe-4-OMe-Ph | CH2-CMe2-NH-(1-(5-Et-pyrimidin-2-yl)-piperidin-4-yl) | 556.7 |
| 506. | CH | Me | H | Me | 2,6-diMe-4-tBu-Ph | (CH2)2-NH-(tetrahydropyran-4-yl) | 449.64 |
| 507. | CH | Et | H | Me | 2,6-diMe-Ph | (CH2)2-NH-(1-(pyrimidin-2-yl)-piperidin-4-yl) | 484.65 |
| 508. | CH | Et | H | Me | 2,6-diMe-Ph | (CH2)2-NH-(1-(pyrimidin-2-yl)-piperidin-4-yl) | 484.65 |
| 509. | CH | nPr | H | Me | 2,6-diMe-Ph | (CH2)2-NH-(1-(pyrimidin-2-yl)-piperidin-4-yl) | 498.7 |
| 510. | CH | Me | H | Me | 2,6-diMe-Ph | (CH2)2-NH-(1-(pyrimidin-2-yl)-piperidin-4-yl) | 470.6 |
| 511. | CH | Et | H | Me | 2,6-diMe-Ph | (CH2)2-NH-(1-Ac-piperidin-4-yl) | 448.62 |
| 512. | CH | Et | H | Me | 2,6-diMe-Ph | (CH2)2-NH-(1,2,3,4-tetrahydro-naphthalen-2-yl) | 453.6 |
| 513. | CH | Et | H | Me | 2,6-diMe-Ph | CH2-CHMe-NH-(1-(pyrimidin-2-yl)-piperidin-4-yl) | 498.7 |
| 514. | CH | nPr | H | Me | 2,6-diMe-Ph | CH2-CHMe-NH-(1-(pyrimidin-2-yl)-piperidin-4-yl) | 512.7 |
| 515. | CH | Me | H | Me | 2,6-diMe-Ph | CH2-CHMe-NH-(1-(pyrimidin-2-yl)-piperidin-4-yl) | 484.7 |
| 516. | CH | Et | H | Me | 2,6-diMe-Ph | CH2-CHMe-NH-(1,2,3,4-tetrahydro-naphthalen-2-yl) | 467.7 |
| 517. | CH | Me | H | Me | 2,6-diOMe-Ph | (CH2)2-NH-(1-Et-piperidin-4-yl) | 452.4 |
| 518. | CH | Me | H | Me | 2,6-diOMe-Ph | (CH2)2-NH-(4-ethyleneketal-cHex) | 481.59 |
| 519. | CH | Me | H | Me | 2,6-diOMe-Ph | (CH2)2-NH-(4-oxo-cHex) | 437.3 |
| 520. | CH | Me | H | Me | 2,6-diOMe-Ph | (CH2)2-NH-(tetrahydropyran-4-yl) | 425.52 |

Example 521

{1-[3-( 2,6-Dichloro-4-methoxy-phenyl)-2,5-dimethyl-pyrazolo[1,5-a]pyrimidin-7-yl]-pyrrolidin-3-yl}-(1-pyrimidin-2-yl-piperidin-4-y;)-amine(MW 567.5)

The pharmaceutical utility of compounds of this invention are indicated by the following assays for human NPY-1 receptor activity.

Assay for Human NPY-1 Receptor Binding Activity

Compounds are assayed for activity using the following method: Baculovirus-infected Sf9 cells expressing recombinant human NPY-1 receptors are harvested at 42–48 hours at which time batches of 500 mL of cell suspension are pelleted by centrifugation. Each pellet is re-suspended in 30 mL of lysis buffer (10 mM HEPES, 250 mM sucrose, 0.5 µg/mL leupeptin, 2 µg/mL Aprotonin, 200 µM PMSF and 2.5 mM EDTA, pH 7.4) and gently homogenized by 50 strokes using a dounce homogenizer. The homogenate is centrifuged at 4° C. for 10 minutes at 536×g to pellet the nuclei. The supernatant is collected into a fresh tube and centrifuged twice in the same buffer at 48,000×g for 40 minutes. The final pellet was re-suspended in 10 mL of PBS containing 5 mM EDTA by dounce homogenization and stored in aliquots at −80° C.

Purified membranes are washed by PBS and re-suspended by gentle pipetting in binding buffer (50 mM Tris(HCl), 5 mM KCl, 120 mM NaCl, 2 mM CaCl2, 1 mM MgCl2, 0.1% bovine serum albumin (BSA), pH 7.4). Membranes (5 µg) are added to siliconized (Sigmacote, Sigma) polypropylene tubes in addition to 0.050 nM [125I]NPY(porcine) for competition analysis or 0.010–0.500 nM [125I]NPY (porcine) for saturation analysis. For evaluation of guanine nucleotide effects on receptor affinity, GTP is added at a final concentration of 100 µM. Cold displacers are added at concentrations ranging from 10−12 M to 10−6 M to yield a final volume of 0.250 mL. Nonspecific binding is determined in the presence of 1 µM NPY (human) and accounts for less than 10% of total binding. Following a 2 hour incubation at room temperature, the reaction is terminated by rapid vacuum filtration. Samples are filtered over presoaked GF/C Whatmnan filters (1.0% polyethyleneimine for 2 hours) and rinsed 2 times with 5 mL cold binding buffer lacking BSA. Remaining bound radioactivity is measured by gamma counting. To estimate the Bmax, Kd and Ki, the results of binding experiments are analyzed using SigmaPlot software (Jandel). The binding affinity for the compounds of the invention, expressed as a Ki value, ranges from about 0.1 nanomolar to about 10 micromolar. The most active compounds of the invention have a Ki of less than 100 nanomolar and a binding selectivity of >100-fold relative to other G-protein coupled receptors, including $NPY_5$ and $CRF_1$ receptors.

hNPY 1–36 Induced $GTP\gamma^{35}S$ Binding at Human NPY Y1 Receptors Co-Expressed With $G\alpha i2$, $G\beta 1$, and $G\gamma 2$ in Sf9 Cells.

Agonist induced $GTP\gamma^{35}S$ binding by G-protein coupled receptors (GPCR) provides a functional measure of G-protein activation. This assay has been widely used for many GPCR's and offers the possibility to distinguish agonists from antagonists and to determine potency and efficacy of agonists for a given GPCR [Thomas et al., 1995; O'Boyle and Lawler, 1995]. $GTP\gamma^{35}S$ binding activity was measured using a modification of a previously described method [Wieland and Jacobs, 1994]. Log-phase Sf9 cells were co-infected with separate baculoviral stocks encoding the hNPY Y1 receptor and the G-protein subunits $\alpha i2$, $\beta 1$, and $\gamma 2$ followed by culturing in Hink's TNM-FH insect medium supplemented Grace's with 4.1 mM L-Gln, 3.3 g/L LAH, 3.3 g/L ultrafiltered yeastolate and 10% heat-inactivated fetal bovine serum at 27° C. 72 hours post infection, a sample of cell suspension was analyzed for viability by trypan blue dye exclusion, and the remaining Sf9 cells were harvested via centrifugation (3000 rpm/10 min/4° C.). Each pellet was re-suspended in homogenization buffer (10 mM HEPES, 250 mM sucrose, 0.5 µg/ml leupeptin, 2 µg/ml Aprotonin, 200 µM PMSF and 2.5 mM EDTA, pH 7.4) and homogenized using a Polytron (setting 5 for 30 seconds). The homogenate was centrifuged at 4° C. for 10 minutes at 536×g to pellet the nuclei. The supernatant was collected into a fresh tube and centrifuged twice in the same buffer at 48,000×g for 40 minutes. The final pellet for each membrane preparation was re-suspended in DPBS containing 5 mM EDTA and stored in aliquots at −80° C. On the day of the assay, thawed membrane homogenates were re-suspended in assay buffer (50 mM Tris pH 7.0, 120 mM NaCl, 2 mM $MgCl_2$, 2 mM EGTA, 0.1% BSA, 0.1 mM bacitracin, 100 KIU/mL Aprotinin, 5 µM GDP) and added to reaction tubes at a concentration of 30 µg/reaction tube. After adding test compounds at concentrations ranging from $10^{-11}M$ to $10^{-5}M$, reactions were initiated by the addition of both 100 pM $GTP\gamma^{35}S$ and hNPY1-36 ranging in concentration from 0.001 nM to 1.0 µM (final volume of 0.250 ml). Following a 30 minute incubation at RT°, the reaction was terminated by vacuum filtration over GF/C filters ( Pre-soaked in wash buffer, 0.1% BSA) with ice-cold wash buffer (50 mM Tris pH 7.0, 120 mM NaCl). Bound $GTP\gamma^{35}S$ was determined by liquid scintillation spectrometry. Non-specific binding was defined by 10 µM $GTP_\gamma^{35}S$ and represented less than 5 percent of total binding. To estimate the $EC_{50}$, $IC_{50}$ and $K_i$, the results of $GTP\gamma^{35}S$ binding experiments were analyzed using SigmaPlot software (Jandel). The binding affinity for the compounds of the invention, expressed as a Ki value, ranges from about 0.1 nanomolar to about 10 micromolar. The most active compounds of the invention have a Ki of less than 100 nanomolar.

Food Deprivation Model

Subjects. Experimentally naive and experienced male Sprague-Dawley rats (Sasco, St. Louis, Mo.) weighing 210–300 g at the beginning of the experiment were used. Animals were triple-housed in stainless steel hanging cages in a temperature (22 C±2 ) and humidity (40–70% RH) controlled animal facility with a 12:12 hour light-dark cycle. Food (Standard Rat Chow, PMI Feeds Inc., #5012) and water were available ad libitum.

Apparatus. Consumption data was collected while the animals were housed in Nalgene Metabolic cages (Model #650-0100). Each cage was comprised of subassemblies made of clear polymethlypentene (PMP), polycarbonate (PC), or stainless steel (SS). All parts disassemble for quick and accurate data collection and for cleaning. The entire cylinder-shaped plastic and SS cage rests on a SS stand and houses one animal.

The animal is contained in the round Upper Chamber (PC) assembly (12 cm high and 20 cm in diameter) and rests on a SS floor. Two subassemblies are attached to the Upper Chamber. The first assembly consists of a SS feeding chamber (10 cm long, 5 cm high and 5 cm wide) with a PC feeding drawer attached to the bottom. The feeding drawer has two compartments: a food storage compartment with the capacity for approximately 50 g of pulverized rat chow, and a food spillage compartment. The animal is allowed access to the pulverized chow by an opening in the SS floor of the feeding chamber. The floor of the feeding chamber does not allow access to the food dropped into the spillage compartment. The second assembly includes a water bottle support, a PC water bottle (100 ml capacity) and a graduated water spillage collection tube. The water bottle support funnels any spilled water into the water spillage collection tube.

The lower chamber consists of a PMP separating cone, PMP collection funnel, PMP fluid (urine) collection tube, and a PMP solid (feces) collection tube. The separating cone is attached to the top of the collection funnel, which in turn is attached to the bottom of the Upper Chamber. The urine runs off the separating cone onto the walls of the collection funnel and into the urine collection tube. The separating cone also separates the feces and funnels it into the feces collection tube.

Food consumption, water consumption, and body weight were measured with an Ohaus Portable Advanced scale (±0.1 g accuracy).

Procedure. Prior to the day of testing, animals were habituated to the testing apparatus by placing each animal in a Metabolic cage for 1 hour. On the day of the experiment, animals that were food deprived the previous night were weighed and assigned to treatment groups. Assignments were made using a quasi-random method utilizing the body weights to assure that the treatment groups had similar average body weight. Animals were then administered either vehicle (0.5% methyl cellulose, MC) or drug. At that time, the feeding drawer filled with pulverized chow, the filled water bottle, and the empty urine and feces collection tubes were weighed. Two hours after drug treatment, each animal was weighed and placed in a Metabolic Cage. Following a one hour test session, animals were removed and body weight obtained. The food and water containers were then weighed and the data recorded.

Drugs. Drug (suspended in 0.5% MC) or 0.5% MC was administered orally (PO) using a gavage tube connected to a 3 or 5 ml syringe at a volume of 10 ml/kg. Drug was made into a homogenous suspension by stirring and ultrasonicating for at least 1 hour prior to dosing.

Statistical Analyses. The means and standard errors of the mean (SEM) for food consumption, water consumption, and body weight change are presented. One-way analysis of variance using Systat (5.2.1) was used to test for group differences. A significant effect is defined as having a p value of <0.05.

The following parameters are defined: Body weight change is the difference between the body weight of the animal immediately prior to placement in the metabolic cage and its body weight at the end of the one hour test session. Food consumption is the difference in the weight of the food drawer prior to testing and the weight following the 1 hour test session. Water consumption is the difference in the weight of the water bottle prior to testing and the weight following the 1 hour test session. The most potent compounds of the invention significantly reduce food intake and body weight gain.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula

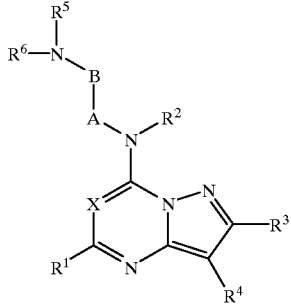

or a pharmaceutically acceptable salt, hydrate, or prodrug thereof, wherein:

X is N or $CR^{14}$;

$R^1$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, $C_1$–$C_6$ alkyl-$NR^8R^9$;

$R^2$ is H, $C_1$–$C_6$ alkyl which optionally forms a $C_3$–$C_6$ aminocarbocycle or a $C_2$–$C_5$ aminoheterocycle with A or B, each of which is optionally substituted with $R^7$, $C_3$–$C_{10}$ cycloalkyl, or ($C_3$–$C_{10}$ cycloalkyl) $C_1$–$C_6$ alkyl; or $R^2$ and $R^6$ jointly with the 2 nitrogen atoms to which they are bound, form a $C_2$–$C_5$ aminoheterocycle optionally substituted with $R^7$, or $R^2$ and A jointly form a $C_3$–$C_6$ aminocarbocycle or a $C_2$–$C_5$ aminoheterocycle optionally substituted with $R^7$;

A represents an alkyl chain of 1, 2, or 3 carbon atoms which is optionally mono- or di-substituted at each carbon with substituents independently selected from $C_1$–$C_6$ alkyl, $C_3$–$C_{10}$ cycloalkyl, ($C_3$–$C_{10}$ cycloalkyl) $C_1$–$C_6$ alkyl, $C_1$–$C_6$ alkenyl, $C_1$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, and $C_1$–$C_6$ alkyl-$NR^8R^9$; or A and B jointly form a $C_3$–$C_6$ carbocycle, optionally substituted at each atom with $R^7$;

B represents an alkyl chain of 1, 2 or 3 carbons atoms, which is optionally mono- or di-substituted at each carbon with substituents independently selected from $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, and $C_1$–$C_6$ alkyl-$NR^8R^9$; or B and $R^2$ jointly form a $C_3$–$C_6$ aminocarbocycle, which is optionally substituted at each atom with $R^7$; or B and $R^6$ jointly form a $C_3$–$C_6$ aminocarbocycle, which is optionally substituted at each atom with $R^7$;

$R^3$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$, $C_1$–$C_6$ cyanoalkyl, $NR^8R^9$, $C_1$–$C_6$ alkyl-$NR^8R^9$;

$R^4$ is selected from aryl or heteroaryl, each of which is substituted with 1 to 5 substituents independently selected from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, $C_1$–$C_6$ alkynyl, halogen, $C_1$–$C_6$ haloalkyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$ alkyl-$CONR^8R^9$, $COOR^7$, $C_1$–$C_6$ alkyl-$COOR^7$, CN, $C_1$–$C_6$ alkyl-CN, $SO_2NR^8R^9$, $SO_2R^7$, aryl, heteroaryl, heterocycloalkyl, 3-, 4-, or 5-(2-oxo-1,3-oxazolidinyl), wherein at least one of the positions ortho or para to the point of attachment of the aryl or heteroaryl ring to the pyrazole is substituted;

$R^5$ is selected from:

$C_1$–$C_6$ alkyl, ($C_3$–$C_{10}$ cycloalkyl) $C_1$–$C_6$ alkyl, $C_2$–$C_6$ alkenyl, $C_2$–$C_6$ alkynyl, each of which is substituted with 1 to 5 groups independently selected at each occurrence from halo, $C_1$–$C_2$ haloalkyl, oxo, $OR^7$, cyano, $NR^8R^9$, $CONR^8R^9$, $COOR^7$, $SO_2NR^8R^9$, $SO_2R^7$, $NR^{11}COR^{12}$, $NR^{11}SO_2R^7$; or Aryl($C_1$–$C_6$)alkyl, heteroaryl($C_1$–$C_6$)alkyl, aryl ($C_5$–$C_8$)cycloalkyl, or heteroaryl($C_5$–$C_8$)cycloalkyl, each of which is optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, $OR^7$, $NR^8R^9$, $C_1$–$C_6$ alkyl-$OR^7$, $C_1$–$C_6$ alky-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), wherein any 2 adjacent substituents may be take together to form a $C_3$–$C_{10}$ cycloalkyl ring, a $C_3$–$C_{10}$ cycloalkenyl ring or a heterocycloalkyl ring; or an unsubstituted $C_2$–$C_9$ heterocycloalkyl containing one, two or three O, S, or N atoms; or $C_3$–$C_{10}$ cycloalkyl or $C_2$–$C_9$ heterocycloalkyl containing one, two, or three O, S, or N atoms, each of which is substituted with 1 to 6 substituents independently selected from $C_1$–$C_6$ alkyl, $C_3$–$C_{10}$, cycloalkyl, $C_3$–$C_{10}$ cycloalkenyl, ($C_3$–$C_{10}$ cycloalkyl) $C_1$–$C_6$ alkyl, $C_1$–$C_6$ alkenyl, oxo, halogen, $C_1$–$C_6$ haloalkyl, $OR^7$, $NR^8R^9$, (with the proviso that when two $OR^7$ or $NR^8R^9$ substituents are geminally located on the same carbon $R^7$ is not H and the geminally located $OR^7$ or $NR^8R^9$ substituents can be taken together to form a $C_2$–$C_4$ ketal, oxazoline, oxazolidine, imidazoline, or imidazolidine heterocycle), $C_1$–$C_6$ alkyl-$OR^7$, $C_1$–$C_6$ alkyl-$NR^8R^9$, $CONR^8R^9$, $COOR^7$, CN, oxo, hydroximino, $C_1$–$C_6$ alkoximino, $SO_2NR^8R^9$, $SO_2R^7$, heterocycloalkyl, aryl, heteroaryl, where aryl or heteroaryl is optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, $OR^7$, $NR^8R^9$, $C_1$–$C_6$ alkyl-$OR^7$, $C_1$–$C_6$ alkyl-$NR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), with the proviso that 2 adjacent substituents can optionally form together a $C_3$–$C_{10}$ cycloalkyl ring, a $C_3$–$C_{10}$ cycloalkenyl ring or a heterocycloalkyl ring; or aryl or heteroaryl, optionally substituted with 1 to 5 substituents independently selected at each occurrence from halogen, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), wherein any 2 adjacent substituents may be taken together to form a $C_3$–$C_{10}$ cycloalkyl ring, a $C_3$–$C_{10}$ cycloalkenyl ring or a heterocycloalkyl ring; or 3- or 4-piperidinyl, 3-pyrrolidinyl, 3- or 4-tetrahydropyranyl, 3-tetrahydrofuranyl, 3- or 4-tetrahydropyranyl, 3-tetrahydrofuranyl, 3- or 4-tetrahydrothiopyranyl, 3- or 4-(1,1-dioxo)tetrahydrothiopyranyl, 1-azabicyclo[4.4.0]decyl, 8-azabicyclo[3.2.1]octanyl, norbornyl, quinuclidinyl, indolin-2-one-3-yl, 2-(methoximino)-perhydroazepin-6-yl, each optionally substituted with 1 to 5 substituents independently selected at each occurrence from $R^7$, $C_1$–$C_6$ alkyl-$OR^7$, $C_1$–$C_6$ alkyl-$NR^8R^9$, $CONR^8R^9$, CN, $COOR^7$ $SO_2NR^8R^9$, and $SO_2R^7$;

$R^6$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, aryl($C_1$–$C_6$)alkyl, heteroaryl($C_1$–$C_6$)alkyl each of which is optionally substituted with 1 to 5 substituents independently from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^7$, CN, $SO_2NR^8R^9$, and $SO_2R^7$;

$R^7$ is independently selected at each occurrence from H, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl each optionally substituted with 1 to 5 substituents independently selected from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^{13}$, CN, $SO_2NR^8R^9$, and $SO_2R^{13}$, with the proviso that when $R^7$ is $SO_2R^{13}$ cannot be H;

$R^8$ and $R^9$ are independently selected at each occurrence from H, $C_1$–$C_6$ alkyl, $C_3$–$C_{10}$ cycloalkyl, $C_2$–$C_6$ alkenyl, $C_3$–$C_{10}$ cycloalkenyl, $C_2$–$C_6$ alkynyl, heterocyclkyl $C_1$–$C_8$ alkanoyl, aryl, heteroaroyl, aryl, heteroaryl, $C_1$–$C_6$ arylalkyl or $C_1$–$C_6$ heteroarylalkyl, or $R^8$ and $R^9$, taken together, can form a $C_3$–$C_6$ aminocarbocycle or a $C_2$–$C_5$ aminoheterocycle each of which is optionally substituted with $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aryl, heteroaroyl, aroyl, heteroaryl, $C_1$–$C_6$ arylalkyl or $C_1$–$C_6$ heteroarylalkyl;

$R^{11}$ is selected from H, $C_1$–$C_6$ alkyl, $C_3$–$C_{10}$ cycloalkyl, ($C_3$–$C_{10}$ cycloalkyl) $C_1$–$C_6$ alkyl;

$R^{12}$ is selected from H, aryl, heteroaryl, $C_1$–$C_6$ alkyl, $C_3$–$C_{10}$ cycloalkyl, ($C_3$–$C_{10}$ cycloalkyl) $C_1$–$C_6$ alkyl, optionally substituted with $OR^7$, $NR^8R^9$, $C_3$–$C_6$ aminocarbocycle, or $C_2$–$C_5$ aminoheterocycle;

$R^{13}$ is independently selected at each occurrence from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, $C_1$–$C_6$ haloalkyl, with the proviso that when $R^7$ is $SO_2R^{13}$, $R^{13}$ cannot be H; and $R^{14}$ is H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, $C_2$–$C_4$ alkynyl, halo, or CN.

2. A compound according to claim 1, wherein $R^5$ is phenyl, naphthyl, 2-, 3-, or 4-pyridyl, 2-, 4- or 5-pyrimidinyl, triazinyl, 1-, 2- or 4-imidazolyl, 2-, 4-, or 5-oxazolyl, isoxazolyl, indolyl, pyrazolyl, quinolyl, isoquinolyl, 2-, 4-, or 5-thiazolyl, benzothiadiazolyl, 1-, 3- or 4-pyrazolyl, 1-, 3- or 4-triazolyl, 2-triazinyl, 2-pyrazinyl, 2-, or 3-furanyl, 2-, or 3-thienyl, 2-, or 3-benzothienyl, or 1-, 2- or 5-tetrazolyl each of which is optionally substituted with 1 to 5 substituents independently selected from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), wherein 2 adjacent substituents may be taken together to form a cycloalkyl ring, a $C_3$–$C_{10}$ cycloalkenyl ring or a heterocycloalkyl ring.

3. A compound according to claim 1, wherein

X is N $R^1$ is H, $C_1$–$C_6$ alkyl, $C_3$–$C_{10}$ cycloalkyl, or ($C_3$–$C_{10}$ cycloalkyl) $C_1$–$C_6$ alkyl; and $R^6$ is H, $C_1$–$C_6$ alkyl, $C_3$–$C_{10}$ cycloalkyl, or ($C_3$–$C_{10}$ cycloalkyl) $C_1$–$C_6$ alkyl.

4. A compound according to claim 1, wherein

X is N;

$R^1$ is $C_1$–$C_6$ alkyl;

$R^2$ is H or $C_1$–$C_6$ alkyl;

$R^3$ is $C_1$–$C_6$ alkyl, trifluoromethyl, or $C_1$–$C_6$alkyl-O $C_1$–$C_6$alkyl; and $R^6$ is H, $C_1$–$C_6$ alkyl, $C_3$–$C_{10}$ cycloalkyl, or ($C_3$–$C_{10}$ cycloalkyl) $C_1$–$C_6$ alkyl.

5. A compound according to claim 1, wherein

X is N;

$R^1$ is $C_1$–$C_6$ alkyl;

$R^2$ is H or $C_1$–$C_6$ alkyl;

$R^3$ is $C_1$–$C_6$ alkyl, trifluoromethyl, or $C_1$–$C_6$alkyl-O $C_1$–$C_6$alkyl;

$R^4$ is phenyl, mono, di, or trisubstituted with $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$alkyl-$CONR^8R^9$, $COOR^7$, $C_1$–$C_6$ alkyl-$COOR^7$, CN, $C_1$–$C_6$ alkyl-CN, $SO_2NR^8R^9$, $SO_2R^7$, aryl, heteroaryl, heterocycloalkyl, 3-, 4-, or 5-(2-oxo-1,3-oxazolidinyl), wherein at least one of the positions ortho or para to the point of attachment of the aryl or heteroaryl ring to the pyrazole is substituted;

$R^6$ is H, $C_1$–$C_6$ alkyl, $C_3$–$C_{10}$ cycloalkyl, or ($C_3$–$C_{10}$ cycloalkyl) $C_1$–$C_6$ alkyl; and $R^7$, $R^8$, and $R^9$ are as defined in claim 1.

6. A compound according to claim 1, wherein:

X is N;

$R^1$ is $C_1-C_6$ alkyl;

$R^2$ is H or $C_1-C_6$ alkyl;

$R^3$ is $C_1-C_6$ alkyl, trifluoromethyl, or $C_1-C_6$ alkyl-O $C_1-C_6$ alkyl;

$R^4$ is phenyl, mono, di, or trisubstituted with $C_1-C_6$ alkyl, $C_3-C_{10}$ cycloalkyl, $C_3-C_{10}$ cycloalkenyl, ($C_3-C_{10}$ cycloalkyl) $C_1-C_6$ alkyl, $C_1-C_6$ alkenyl, halogen, $C_1-C_6$ haloalkyl, $OR^7$, $C_1-C_6$ alkyl-$OR^7$, $NR^8R^9$, $C_1-C_6$ alkyl-$NR^8R^9$, $CONR^8R^9$, $C_1-C_6$ alkyl-$CONR^8R^9$, $COOR^7$, $C_1-C_6$ alkyl-$COOR^7$, CN, $C_1-C_6$ alkyl-CN, $SO_2NR^8R^9$, $SO_2R^7$, aryl, heteroaryl, heterocycloalkyl, 3-, 4-, or 5-(2-oxo-1,3-oxazolidinyl), wherein at least one of the positions ortho or para to the point of attachment of the aryl or heteroaryl ring to the pyrazole is substituted;

$R^5$ is $C_1-C_6$ alkyl, $C_3-C_{10}$ cycloalkyl, ($C_3-C_{10}$ cycloalkyl) $C_1-C_6$ alkyl, $C_2-C_6$ alkenyl, $C_2-C_6$ alkynyl, each of which is substituted with 1 to 5 groups independently selected at each occurrence from halo, $C_1-C_2$ haloalkyl, $OR^7$, cyano, $NR^8R^9$, $CONR^8R^9$, $COOR^7$, $SO_2NR^8R^9$, $SO_2R^7$, $NR^{11}COR^{12}$, $NR^{11}SO_2R^7$; or 3- or 4-piperidinyl, 3-pyrrolidinyl, 3- or 4-tetrahydropyranyl, 3-tetrahydrofuranyl, 3- or 4-tetrahydropyranyl, 3-tetrahydrofuranyl, 3- or 4-tetrahydrothiopyranyl, 3- or 4-(1,1-dioxo) tetrahydrothiopyranyl, 1-azabicyclo[4.4.0]decyl, 8-azabicyclo[3.2.1]octanyl, norbornyl, quinuclidinyl, indolin-2-one-3-yl, 2-(methoximino)-perhydroazepin-6-yl, each optionally substituted with 1 to 5 substituents independently selected at each occurrence from $R^7$, $C_1-C_6$ alkyl-$OR^7$, $C_1-C_6$ alkyl-$NR^8R^9$, $CONR^8R^9$, CN $COOR^7$, $SO_2NR^8R^9$ and $SO_2R^7$;

$R^6$ is H, $C_1-C_6$ alkyl, $C_3-C_{10}$ cycloalkyl, or ($C_3-C_{10}$ cycloalkyl) $C_1-C_6$ alkyl; and $R^7$, $R^8$, $R^9$, $R^{11}$, and $R^{12}$ are as defined in claim 1.

7. A compound according to claim 1, wherein;

X is CH, $R^1$ is H, $C_1-C_6$ alkyl, $C_3-C_{10}$ cycloalkyl, or ($C_3-C_{10}$ cycloalkyl) $C_1-C_6$ alkyl; and $R^6$ is H, $C_1-C_6$ alkyl, $C_3-C_{10}$ cycloalkyl, or ($C_3-C_{10}$ cycloalkyl) $C_1-C_6$ alkyl.

8. A compound according to claim 1, wherein:

X is CH;

$R^1$ is $C_1-C_6$ alkyl;

$R^2$ is H or $C_1-C_6$ alkyl;

$R^3$ is $C_1-C_6$ alkyl, trifluoromethyl, or $C_1-C_6$alkyl-O $C_1-C_6$alkyl; and $R^6$ is H, $C_1-C_6$ alkyl, $C_3-C_{10}$ cycloalkyl, or ($C_3-C_{10}$ cycloalkyl) $C_1-C_6$ alkyl.

9. A compound according to claim 1, wherein;

X is CH;

$R^1$ is $C_1-C_6$ alkyl;

$R^2$ is H or $C_1-C_6$ alkyl;

$R^3$ is $C_1-C_6$ alkyl, trifluoromethyl, or $C_1-C_6$ alkyl-O $C_1-C_6$ alkyl;

$R^4$ is phenyl, mono, di, or trisubstituted with $C_1-C_6$ alkyl, $C_3-C_{10}$ cycloalkyl, $C_3-C_{10}$ cycloalkenyl, ($C_3-C_{10}$ cycloalkyl) $C_1-C_6$ alkyl, $C_1-C_6$ alkenyl, halogen, $C_1-C_6$ haloalkyl, $OR^7$, $C_1-C_6$ alkyl-$OR^7$, $NR^8R^9$, $C_1-C_6$ alkyl-$NR^8R^9$, $CONR^8R^9$, $C_1-C_6$ alkyl-$CONR^8R^9$, $COOR^7$, $C_1-C_6$ alkyl-$COOR^7$, CN, $C_1-C_6$ alkyl-CN, $SO_2NR^8R^9$, $SO_2R^7$, aryl, heteroaryl, heterocycloalkyl, 3-, 4-, or 5-(2-oxo-1,3-oxazolidinyl), wherein at least one of the positions ortho or para to the point of attachment of the aryl or heteroaryl ring to the pyrazole is substituted;

$R^6$ is H, $C_1-C_6$ alkyl, $C_3-C_{10}$ cycloalkyl, or ($C_3-C_{10}$ cycloalkyl) $C_1-C_6$ alkyl; and $R^7$, $R^8$, and $R^9$ are as defined in claim 1.

10. A compound according to claim 1, wherein:

X is CH;

$R^1$ is $C_1-C_6$ alkyl;

$R^2$ is H or $C_1-C_6$ alkyl;

$R^3$ is $C_1-C_6$ alkyl, trifluoromethyl, or $C_1-C_6$ alkyl-O $C_1-C_6$ alkyl;

$R^4$ is phenyl, mono, di, or trisubstituted with $C_1-C_6$ alkyl, $C_3-C_{10}$ cycloalkyl, $C_3-C_{10}$ cycloalkenyl, ($C_3-C_{10}$ cycloalkyl) $C_1-C_6$ alkyl, $C_1-C_6$ alkenyl, halogen, $C_1-C_6$ haloalkyl, $OR^7$, $C_1-C_6$ alkyl-$OR^7$, $NR^8R^9$, $C_1-C_6$ alkyl-$NR^8R^9$, $CONR^8R^9$, $C_1-C_6$ alkyl-$CONR^8R^9$, $COOR^7$, $C_1-C_6$ alkyl-$COOR^7$, CN, $C_1-C_6$ alkyl-CN, $SO_2NR^8R^9$, $SO_2R^7$, aryl heteroaryl, heterocycloalkyl, 3-, 4-, or 5-(2-oxo-1,3-oxazolidinyl), wherein at least one of the positions ortho or para to the point of attachment of the aryl or heteroaryl ring to the pyrazole is substituted;

$R^5$ is $C_1-C_6$ alkyl, $C_3-C_{10}$ cycloalkyl, ($C_3-C_{10}$ cycloalkyl) $C_1-C_6$ alkyl, $C_2-C_6$ alkenyl, $C_2-C_6$ alkynyl, each of which is substituted with 1 to 5 groups independently selected at each occurrence from halo, $C_1-C_2$ haloalkyl, $OR^7$, cyano, $NR^8R^9$, $CONR^8R^9$, $COOR^7$, $SO_2NR^8R^9$, $SO_2R^7$, $NR^{11}COR^{12}$, $NR^{11}SO_2R^7$; or 3- or 4-piperidinyl, 3-pyrrolidinyl, 3- or 4-tetrahydropyranyl, 3-tetrahydrofuranyl, 3- or 4-tetrahydropyranyl, 3-tetrahydrofuranyl, 3- or 4-tetrahydrothiopyranyl, 3- or 4-(1,1-dioxo) tetrahydrothiopyranyl, 1-azabicyclo[4.4.0]decyl, 8-azabicyclo[3.2.1]octanyl, norbornyl, quinuclidinyl, indolin-2-one-3-yl, 2-(methoximino)-perhydroazepin-6-yl, each optionally substituted with 1 to 5 substituents independently selected at each occurrence from $R^7$, $C_1-C_6$ alkyl-$OR^7$, $C_1-C_6$ alkyl-$NR^8R^9$, $CONR^8R^9$, CN, $COOR^7$ $SO_2NR^8R^9$, and $SO_2R^7$;

$R^6$ is H, $C_1-C_6$ alkyl, $C_3-C_{10}$ cycloalkyl, or ($C_3-C_{10}$ cycloalkyl) $C_1-C_6$ alkyl; and $R^7$, $R^8$, $R^9$, $R^{11}$, and $R^{12}$ are as defined in claim 1.

11. A method for treating eating disorders and cardiovascular disorders comprising administering to a patient suffering from an eating disorder or cardiovascular disorder a compound according to claim 1.

12. A pharmaceutical composition comprising a compound according to claim 1 and a pharmaceutically acceptable carrier.

13. A packaged pharmaceutical composition comprising the pharmaceutical composition of claim 12 in a container and comprising instructions for using the composition to treat a patient suffering from an eating disorder or hypertension.

14. A method for localizing NPY receptors in tissue section samples comprising:

contacting with a sample of tissue a detectably-labeled compound of claim 1 which permits binding of the compound to the sample of tissue;

washing the tissue sample to remove unbound compound; and detecting the bound compound.

15. The method of claim 14, wherein the compound is radiolabeled.

16. A compound according to of claim 1 wherein in an assay of NPY binding the compound exhibits an $K_i$ of 1 micromolar or less.

17. A compound according to claim 1 wherein in an assay of NPY binding the compound exhibits an $K_i$ of 100 nanomolar or less.

18. A compound according to claim 1 wherein in an assay of NPY binding the compound exhibits an $K_i$ of 100 nanomolar 10 nanomolar or less.

19. A method for treating obesity or bulimia nervosa which comprises administering an effective amount of a compound according to claim 1 to a patient in need thereof.

20. A method for treating hypertension which comprises administering an effective amount of a compound according to claim 1 to a patient in need thereof.

21. A compound in accordance with formula I

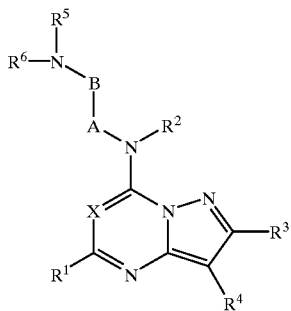

wherein:

X is N or $CR^{14}$;

$R^1$ is selected from H, $C_1$–$C_6$ alkyl, $C_3$–$C_6$ cycloalkyl, ($C_3$–$C_{10}$cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, $C_1$–$C_6$ alkyl-$NR^8R^9$;

$R^2$ is H, $C_1$–$C_6$ alkyl which optionally forms a $C_3$–$C_6$ aminocarbocycle or a $C_2$–$C_5$ aminoheterocycle with A or B, each of which is optionally substituted at each occurrence with $R^7$, $C_3$–$C_{10}$ cycloalkyl, or ($C_3$–$C_{10}$ cycloalkyl) $C_1$–$C_6$ alkyl; or $R^2$ and $R^6$ jointly form with the 2 nitrogen atoms to which they are bound, form a $C_2$–$C_5$ aminoheterocycle optionally substituted at each occurrence with $R^7$;

A is $(CH_2)_m$, where m is 1, 2 or 3 and is optionally mono- or di-substituted on each occurrence with $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, $C_1$–$C_6$ alkyl-$NR^8R^9$; or A and B jointly form a $C_3$–$C_6$ carbocycle, optionally substituted at each occurrence with $R^7$; or A and $R^2$ jointly form a $C_3$–$C_6$ aminocarbocycle or a $C_2$–$C_5$ aminoheterocycle optionally substituted at each occurrence with $R^7$;

B is $(CH_2)_n$, where n is 1, 2 or 3 and is optionally mono- or di-substituted on each occurrence with $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, and $C_1$–$C_6$ alkyl-$NR^8R^9$; or, as mentioned above, B and A jointly form a $C_3$–$C_6$ carbocycle, optionally substituted at each occurrence with $R^7$; as mentioned above, B and $R^2$ jointly form a $C_3$–$C_6$ aminocarbocycle or a $C_2$–$C_5$ aminoheterocycle optionally substituted at each occurrence with $R^7$;

$R^3$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ cyanoalkyl, $NR^8R^9$, $C_1$–$C_6$ alkyl-$NR^8R^9$;

$R^4$ is selected from aryl or heteroaryl, each of which is substituted with 1 to 5 substituents independently selected from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, $C_1$–$C_6$ alkynyl, halogen, $C_1$–$C_6$ haloalkyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$ alkyl-$CONR^8R^9$, $COOR^7$, $C_1$–$C_6$ alkyl-$COOR^7$, CN, $C_1$–$C_6$ alkyl-CN, $SO_2NR^8R^9$, $SO_2R^7$, aryl, heteroaryl, heterocycloalkyl, 3-, 4-, or 5-(2-oxo-1,3-oxazolidinyl), wherein at least one of the positions ortho or para to the point of attachment of the aryl or heteroaryl ring to the pyrazole is substituted;

$R^5$ is selected from:

$C_1$–$C_6$ alkyl, ($C_3$–$C_{10}$ cycloalkyl) $C_1$–$C_6$ alkyl, $C_2$–$C_6$ alkenyl, $C_2$–$C_6$ alkynyl, each of which is substituted with 1 to 5 groups independently selected at each occurrence from halo, $C_1$–$C_2$ haloalkyl, oxo, $OR^7$, cyano, $NR^8R^9$, $CONR^8R^9$, $COOR^7$, $SO_{12}NR^{11}R^9$, $SO_2R^7$, $NR^{11}COR^2$, $NR^8SO_2R^7$; or Aryl($C_1$–$C_6$)alkyl, heteroaryl($C_1$–$C_6$)alkyl, aryl ($C_5$–$C_8$)cycloalkyl, or heteroaryl($C_5$–$C_8$)cycloalkyl, where aryl is phenyl or naphthyl, and heteroaryl is 2-, 3- or 4-pyridyl, 2-, 4-, 5-pyrimidinyl, triazinyl, 1-, 2-, or 4-imidazolyl 2-, 4-, or 5-oxazolyl isoxazolylindolyl, pyrazolyl, quinolyl, isoquinolyl, 2-, 4-, or 5-thiazolyl, benzothiadiazolyl, 1-, 3- or 4-pyrazolyl, 1-, 3- or 4-triazolyl, 2-triazinyl, 2-pyrazinyl, 2-, or 3-furanyl, 2-, or 3-thienyl, 2-, or 3-benzothienyl, or 1-, 2- or 5 tetrazolyl, each of which is optionally substituted with 1 to 5 substituents independently selected at each occurrence from $C_1$–$C_6$ alkyl, $C_3$–$C_{10}$ cycloalkyl, $C_3$–$C_{10}$, cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), wherein any 2 adjacent substituents may be take together to form a $C_3$–$C_{10}$ cycloalkyl ring, a $C_3$–$C_{10}$ cycloalkenyl ring or a heterocycloalkyl ring; or $C_3$–$C_{10}$ cycloalkyl substituted with 1 to 6 substituents independently selected from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, oxo, halogen, $C_1$–$C_6$ haloalkyl, $OR^7$, $NR^8R^9$, (with the proviso that when two $OR^7$ or $NR^8R^9$ substituents are geminally located on the same carbon $R^7$ is not H and the geminally located $OR^7$ or $NR^8R^9$ substituents can be taken together to form a $C_2$–$C_4$ ketal, oxazoline, oxazolidine, imidazoline, or imidazolidine heterocycle), $C_1$–$C_6$ alkyl-$OR^7$, $C_1$–$C_6$ alkyl-$NR^8R^9$, $CONR^8R^9$, $COOR^7$, CN, oxo, hydroximino, $C_1$–$C_6$ alkoximino, $SO_2NR^8R^9$, $SO_2R^7$, heterocycloalkyl, aryl, heteroaryl, where aryl or heteroaryl is optionally substituted with 1 to 5 substituents independently selected at each occurrence from C$_1$–C$_6$ alkyl, C$_3$–C$_{10}$ cycloalkyl, C$_3$–C$_{10}$ cycloalkenyl, (C$_3$–C$_{10}$ cycloalkyl) C$_1$–C$_6$ alkyl, C$_1$–C$_6$ alkenyl, halogen, C$_1$–C$_6$ haloalkyl, OR$^7$, NR$^8$R$^9$, C$_1$–C$_6$ alkyl-OR$^7$, C$_1$–C$_6$ alkyl-NR$^8$R$^9$, CONR$^8$R$^9$, COOR$^7$, CN SO$_2$NR$^8$R$^9$, SO$_2$R$^7$, aryl, heteroaryl, heterocycloalkyl, 3-, 4-, or 5-(2-oxo-1,3-oxazolidinyl), with the proviso that 2 adjacent substituents can optionally form together a C$_3$–C$_{10}$ cycloalkyl ring, a C$_3$–C$_{10}$ cycloalkenyl ring or a heterocycloalkyl ring; or aryl or heteroaryl, optionally substituted with 1 to 5 substituents independently selected at each occurrence from halogen, C$_1$–C$_6$ alkyl, C$_3$–C$_{10}$ cycloalkyl, C$_3$–C$_{10}$ cycloalkenyl, (C$_3$–C$_{10}$ cycloalkyl) C$_1$–C$_6$ alkyl, C$_1$–C$_6$ alkenyl, halogen, C$_1$–C$_6$ haloalkyl, OR$^7$, NR$^8$R$^9$, C$_1$–C$_6$ alkyl-OR$^7$, C$_1$–C$_6$ alkyl-NR$^8$R$^9$, CONR$^8$R$^9$, COOR$^7$, CN, SO$_2$NR$^8$R$^9$, SO$_2$R$^7$, aryl, heteroaryl, heterocycloalkyl, 3-, 4-, or 5-(2-oxo-1,3-oxazolidinyl), wherein any 2 adjacent substituents may be taken together to form a C$_3$–C$_{10}$ cycloalkyl ring, a C$_3$–C$_{10}$ cycloalkenyl ring or a heterocycloalkyl ring; or 3- or 4-piperidinyl, 3-pyrrolidinyl, 3- or 4-tetrahydropyranyl, 3-tetrahydrofuranyl, 3- or 4-tetrahydropyranyl, 3-tetrahydrofuranyl, 3- or 4-tetrahydrothiopyranyl, 3- or 4-(1,1-dioxo)tetrahydrothiopyranyl, 1-azabicyclo[4.4.0]decyl, 8-azabicyclo[3.2.1]octanyl, norbornyl, quinuclidinyl, indolin-2-one-3-yl, 2-(methoximino)-perhydroazepin-6-yl, each optionally substituted with 1 to 5 substituents independently selected at each occurrence from R$^7$, C$_1$–C$_6$ alkyl-OR$^7$, C$_1$–C$_6$ alkyl-NR$^8$R$^9$, CONR$^8$R$^9$, CN, COOR$^7$ SO$_2$NR$^8$R$^9$, and SO$_2$R$^7$;

R$^6$ is selected from H, C$_1$–C$_6$ alkyl, C$_3$–C$_{10}$ cycloalkyl, (C$_3$–C$_{10}$ cycloalkyl) C$_1$–C$_6$ alkyl, C$_2$–C$_4$ alkenyl, aryl(C$_1$–C$_6$)alkyl, heteroaryl(C$_1$–C$_6$)alkyl each of which is optionally substituted with 1 to 5 substituents independently from halogen, C$_1$–C$_6$ haloalkyl, OR$^{13}$, NR$^8$R$^9$, C$_1$–C$_6$ alkyl-OR$^{13}$, C$_1$–C$_6$ alkyl-NR$^8$R$^9$, CONR$^8$R$^9$, COOR$^7$, CN, SO$_2$NR$^8$R$^9$, and SO$_2$R$^7$; or R$^6$ and R$^2$ jointly form with the two nitrogens to which they are bound a C$_2$–C$_5$ aminoheterocycle optionally substituted at each occurrence by R$^7$;

R$^7$ is independently selected at each occurrence from H, C$_1$–C$_6$ alkyl, C$_3$–C$_{10}$ cycloalkyl, C$_3$–C$_{10}$ cycloalkenyl, (C$_3$–C$_{10}$ cycloalkyl) C$_1$–C$_6$ alkyl, C$_1$–C$_3$ haloalkyl, or heterocycloalkyl, C$_1$–C$_8$ alkylsulfonyl, arylsulfonyl, heteroarylsulfonyl, C$_1$–C$_8$ alkanoyl, aroyl, heteroaroyl, aryl, heteroaryl, C$_1$–C$_6$ arylalkyl or C$_1$–C$_6$ heteroarylalkyl each optionally substituted with 1 to 5 substituents independently selected from halogen, C$_1$–C$_6$ haloalkyl, OR$^{13}$, NR$^8$R$^9$, C$_1$–C$_6$ alkyl-OR$^{13}$, C$_1$–C$_6$ alkyl-NR$^8$R$^9$, CONR$^8$R$^9$, COOR$^{13}$, CN, SO$_2$NR$^8$R$^9$, and SO$_2$R$^{13}$, with the proviso that when R$^7$ is SO$_2$R$^{13}$, R$^{13}$ cannot be H;

R$^8$ and R$^9$ are independently selected at each occurrence from H, C$_1$–C$_6$ alkyl, C$_3$–C$_{10}$ cycloalkyl, C$_2$–C$_6$ alkenyl, C$_3$–C$_{10}$ cycloalkenyl, C$_2$–C$_6$ alkynyl, heterocycloalkyl, C$_1$–C$_8$ alkanoyl, aroyl, heteroaroyl, aryl, heteroaryl, C$_1$–C$_6$ arylalkyl or C$_1$–C$_6$ heteroarylalkyl, or R$^8$ and R$^9$, taken together, can form a C$_3$–C$_6$ aminocarbocycle or a C$_2$–C$_5$ aminoheterocycle each of which is optionally substituted with C$_1$–C$_6$ alkyl, C$_3$–C$_{10}$ cycloalkyl, C$_3$–C$_{10}$ cycloalkenyl, (C$_3$–C$_{10}$ cycloalkyl) C$_1$–C$_6$ alkyl, C$_1$–C$_3$ haloalkyl, or heterocycloalkyl, C$_1$–C$_8$ alkylsulfonyl, arylsulfonyl, heteroarylsulfonyl, C$_1$–C$_8$ alkanoyl, aroyl, heteroaroyl, aryl, heteroaryl, C$_1$–C$_6$ arylalkyl or C$_1$–C$_6$ heteroarylalkyl;

R$^{11}$ is selected from H, C$_1$–C$_6$ alkyl, C$_3$–C$_{10}$ cycloalkyl, (C$_3$–C$_{10}$ cycloalkyl) C$_1$–C$_6$ alkyl;

R$^{12}$ is selected from H, aryl, heteroaryl, C$_1$–C$_6$ alkyl, C$_3$–C$_{10}$ cycloalkyl, (C$_3$–C$_{10}$ cycloalkyl) C$_1$–C$_6$ alkyl, optionally substituted with OR$^7$, NR$^8$R$^9$, C$_3$–C$_6$ aminocarbocycle, or C$_2$–C$_5$ aminoheterocycle;

R$^{13}$ is independently selected at each occurrence from H, C$_1$–C$_6$ alkyl, C$_3$–C$_{10}$ cycloalkyl, (C$_3$–C$_{10}$ cycloalkyl) C$_1$–C$_6$ alkyl, C$_2$–C$_6$ alkenyl, C$_2$–C$_6$ alkynyl, C$_1$–C$_6$ haloalkyl, with the proviso that when R$^7$ is SO$_2$R$^{13}$, R$^{13}$ cannot be H; and R$^{14}$ is H, C$_1$–C$_6$ alkyl, C$_3$–C$_{10}$ cycloalkyl, (C$_3$–C$_{10}$ cycloalkyl) C$_1$–C$_6$ alkyl, C$_2$–C$_4$ alkenyl, C$_2$–C$_4$ alkynyl, halo, or CN or a pharmaceutically acceptable salt, hydrate or prodrug thereof.

22. A compound in accordance with formula I

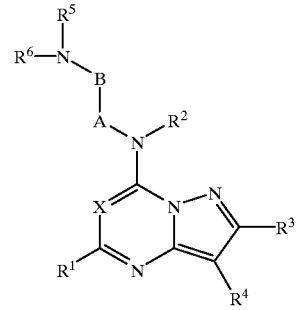

or a pharmaceutically acceptable salt, hydrate or prodrug thereof wherein:

X is N or CR$^{14}$;

R$^1$ is selected from H, C$_1$–C$_6$ alkyl, C$_3$–C$_6$ cycloalkyl, (C$_3$–C$_{10}$cycloalkyl) C$_1$–C$_6$ alkyl, C$_2$–C$_6$ alkenyl, C$_2$–C$_6$ alkynyl, cyano, halo, C$_1$–C$_6$ haloalkyl, OR$^7$, C$_1$–C$_6$ alkyl-OR$^7$; C$_1$–C$_6$ cyanoalkyl, NR$^8$R$^9$, C$_1$–C$_6$ alkyl-NR$^8$R$^9$;

R$^2$ is H, C$_1$–C$_6$ alkyl, C$_3$–C$_{10}$ cycloalkyl, or (C$_3$–C$_{10}$ cycloalkyl) C$_1$–C$_6$ alkyl, wherein each alkyl or cycloalkyl group may be optionally substituted with 1 to 3 R$^{7a}$ groups; or R$^2$ may optionally join with R$^5$ and the two and the 2 nitrogen atoms to which they are bound to form a 6 to 10 membered heterocyclic ring optionally substituted at each carbon with R$^{7a}$; or R$^2$ and A may optionally join to form a 3 to 8 membered heterocyclic ring optionally substituted at each carbon with R$^{7a}$; or R$^2$ and B optionally join to form a 4 to 10 membered heterocyclic ring optionally substituted at each carbon with R$^{7a}$;

A represents an alkyl chain of 1, 2 or 3 carbon atoms which is optionally mono- or di-substituted at each carbon with substituents independently selected from C$_1$–C$_6$ alkyl, C$_3$–C$_{10}$ cycloalkyl, (C$_3$–C$_{10}$ cycloalkyl) C$_1$–C$_6$ alkyl, C$_2$–C$_6$ alkenyl, C$_2$–C$_6$ alkynyl, cyano, halo, C$_1$–C$_6$ haloalkyl, OR$^7$, C$_1$–C$_6$ alkyl-OR$^7$; C$_1$–C$_6$ cyanoalkyl, NR$^8$R$^9$, C$_1$–C$_6$ alkyl-NR$^8$R$^9$; or A and B jointly form a C$_3$–C$_6$ carbocycle, optionally substituted at each occurrence with R$^{7a}$;

B represents an alkyl chain of 1, 2 or 3 carbon atoms, which is optionally mono- or di- substituted at each carbon with substituents independently selected from $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$; $C_1$–$C_6$ cyanoalkyl, $NR^8R^9$, and $C_1$–$C_6$ alkyl-$NR^8R^9$; or B and $R^5$ may jointly form a 4 to 7 membered heterocyclic ring, which is optionally substituted at each atom with $R^{7a}$;

$R^3$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, cyano, halo, $C_1$–$C_6$ haloalkyl, $OR^7$, $C_1$–$C_6$ alkyl-$OR^7$, $C_1$–$C_6$ cyanoalkyl, $NR^8R^9$, $C_1$–$C_6$ alkyl-$NR^8R^9$;

$R^4$ is selected from aryl or heteroaryl, each of which is substituted with 1 to 5 substituents independently selected from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, $C_1$–$C_6$ alkynyl, halogen, $C_1$–$C_6$ haloalkyl, $OR^7$, $C_1$–$C_6$ alkyl-$OR^7$, $NR^8R^9$, $C_1$–$C_6$ alkyl-$NR^8R^9$, $CONR^8R^9$, $C_1$–$C_6$ alkyl-$CONR^8R^9$, $COOR^7$, $C_1$–$C_6$ alyl-$COOR^7$, CN, $C_1$–$C_6$ alkyl-CN, $SO_2NR^8R^9$, $SO_2R^7$, aryl, heteroaryl, heterocycloalkyl, 3-, 4-, or 5-(2-oxo-1,3-oxazolidinyl), $C_2$–$C_4$ alkynyl wherein at least one of the positions ortho or para to the point of attachment of the aryl or heteroaryl ring to the pyrazole is substituted;

$R^5$ is selected from:
 $C_1$–$C_6$ alkyl, ($C_3$–$C_{10}$ cycloalkyl) $C_1$–$C_6$ alkyl, each of which is substituted with 1 to 5 groups independently selected at each occurrence from $C_1$–$C_6$ alkyl, $C_3$–$C_{10}$, cycloalkyl, $C_3$–$C_{10}$ cycloalkenyl, ($C_3$–$C_{10}$ cycloalkyl) $C_1$–$C_6$ alkyl, $C_2$–$C_6$, alkenyl halogen, $C_1$–$C_6$ haloalkyl, $OR^7$, $NR^8R^9$, (with the proviso that when two $OR^7$ or $NR^8R^9$ substituents are geminally located on the same carbon $R^7$ is not H and the geminally located $OR^7$ or $NR^8R^9$ substituents can be taken together to form a $C_2$–$C_4$ ketal, oxazoline, oxazolidine, imidazoline, or imidazolidine heterocycle), $C_1$–$C_6$ alkyl-$OR^7$, $C_1$–$C_6$ alkyl-$NR^8R^9$, $CONR^8R^9$, $COOR^7$, CN, oxo, hydroximino, $C_1$–$C_6$ alkoximino, $SO_2NR^8R^9$, $SO_2R^7$, heterocycloalkyl, aryl, heteroaryl, where aryl or heteroaryl is optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl), $C_1$–$C_6$ alkyl, $C_2$–$C_6$ alkenyl, halogen, $C_1$–$C_6$ haloalkyl, $OR^7$, $NR^8R^9$, $C_1$–$C_6$ alkyl-$OR[_7]^7$, $C_1$–$C_6$ alkyl $NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), with the proviso that 2 adjacent substituents can optionally form together a $C_3$–$C_{10}$, cycloalkyl ring, a $C_3$–$C_{10}$ cycloalkenyl ring or a heterocycloalkyl ring; with the proviso that $C_1$–$C_6$ alkyl group is substituted with a $C_1$–$C_6$ alkyl group to give a $C_7$–$C_{10}$ alkyl group; or
 Aryl($C_1$–$C_6$)alkyl, heteroaryl($C_1$–$C_6$)alkyl, aryl ($C_5$–$C_8$)cycloalkyl, or heteroaryl($C_5$–$C_8$)cycloalkyl, each of which is optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_6$ alkenyl, halogen, $C_1$–$C_6$ haloalkyl, $OR^7$, $NR^8R^9$, $C_1$–$C_6$ alkyl-$OR^7$, $C_7$–$C_6$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl), wherein any 2 adjacent substituents may be take together to form a $C_3$–$C_{10}$ cycloalkyl ring, a $C_3$–$C_{10}$ cycloalkenyl ring or a heterocycloalkyl ring; or $C_2$–$C_6$ alkenyl, $C_2$–$C_6$ alkynyl, $C_3$–$C_{10}$ cycloalkenyl, or a 3 to 10 membered mono- or bicyclic heterocycle containing 1–3 O, S or N atoms, each of which is substituted with 1 to 6 substituents independently selected from $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_2$–$C_6$ alkenyl, halogen, $C_1$–$C_6$ haloalkyl, $OR^7$, $NR^8R^9$, (with the proviso that when two $OR^7$ or $NR^8R^9$ substituents are geminally located on the same carbon $R^7$ is not H and the geminally located $OR^7$ or $NR^8R^9$ substituents can be taken together to form a $C_2$–$C_4$ ketal, oxazoline, oxazolidine, imidazoline, or imidazolidine heterocycle), $C_1$–$C_6$ alkyl-$OR^7$, $C_1$–$C_6$ alkyl-$NR^8R^9$, $CONR^8R^9$, $COOR^7$, CN, oxo hydroximino, $C_1$–$C_6$ alkoximino, $SO_2NR^8R^9$, $SO_2R^7$, $COR^7$, heterocycloalkyl, aryl, $C_1$–$C_6$ alkylaryl, heteroaryl, $C_1$–$C_6$ alkylheteroaryl where aryl or heteroaryl is optionally substituted with 1 to 5 substituents independently selected at each occurrence from $C_1$–$C_6$ alkyl, $C_3$–$C_{10}$ cycloalkyl, $C_3$–$C_{10}$ cycloalkenyl, ($C_3$–$C_1$-cycloalkyl) $C_1$–$C_6$ alkyl, $C_2$–$C_6$ alkenyl, halogen, $C_1$–$C_6$ haloalkyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN $SO_2NR^8R^9$, $SO_2R^7$, aryl, heteroaryl, heterocycloalkyl, 3-, 4-, or 5-(2-oxo-1,3-oxazolidinyl), with the proviso that 2 adjacent substituents can optionally form together a $C_3$–$C_{10}$ cycloalkyl ring, a $C_3$–$C_{10}$ cycloalkenyl ring or a heterocycloalkyl ring; or aryl or heteroaryl, optionally substituted with 1 to 5 substituents independently selected at each occurrence from halogen, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_2$–$C_6$ alkenyl, halogen, $C_1$–$C_6$ haloalkyl, $OR^7$, $NR^8R^9$, $C_1$–$C_6$ alkyl-$OR^7$, $C_1$–$C_6$ alkyl-$NR^8R^9$, $CONR^8R^9$, $COOR^7$, CN, $SO_2NR^8R^9$, $S[0]O[_2]2R^7$, aryl, heteroaryl, heterocycloalkyl, 3-, 4-, or 5-(2-oxo-1,3-oxazolidinyl), wherein any 2 adjacent substituents maybe taken together to form a $C_3$–$C_{10}$ cycloalkyl ring, a $C_3$–$C_{10}$ cycloalkenyl ring or a heterocycloalkyl ring;

$R^6$ is selected from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, aryl($C_1$–$C_6$)alkyl, heteroaryl($C_1$–$C_6$)alkyl each of which is optionally substituted with 1 to 5 substituents independently from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^7$, CN, $SO_2NR^8R^9$, and $SO_2R^7$;

$R^7$ is independently selected at each occurrence from H, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, aryl, heteroaryl, $C_1$–$C_6$ arylalkyl or $C_1$–$C_6$ heteroarylalkyl each optionally substituted with 1 to 5 substituents independently selected from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^{13}$, CN, $SO_2NR^8R^9$, and $SO_2R^{13}$;

$R^{7a}$ is independently selected at each occurrence from H, $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aryl, heteroaroyl, aryl, heteroaryl, $C_1$–$C_6$ arylalkyl or $C_1$–$C_6$ heteroarylalkyl each optionally substituted with 1 to 5 substituents independently selected from halogen, $C_1$–$C_6$ haloalkyl, $OR^{13}$, $NR^8R^9$, $C_1$–$C_6$ alkyl-$OR^{13}$, $C_1$–$C_6$ alkyl-$NR^8R^9$, $CONR^8R^9$, $COOR^{13}$, CN, $SO_2NR^8R^9$, and $SO_2R^{13}$, with the proviso that when $R^{7a}$ is $SO_2R^{13}$, $R^{13}$ cannot be H;

$R^8$ and $R^9$ are independently selected at each occurrence from H, $C_1$–$C_6$ alkyl, $C_3$–$C_{10}$ cycloalkyl, $C_2$–$C_6$ alkenyl, $C_3$–$C_{10}$ cycloalkenyl, $C_2$–$C_6$ alkynyl, heterocycloalkyl, $C_1$–$C_8$ alkanoyl, aroyl, heteroaroyl, aryl, heteroaryl, $C_1$–$C_6$ arylalkyl or $C_1$–$C_6$ heteroarylalkyl, or $R^8$ and $R^9$ taken together can form a $C_3$–$C_6$ aminocarbocycle or a $C_2$–$C_5$ aminoheterocycle each of which is optionally substituted with $C_1$–$C_6$ alkyl, $C_3$–$C_{10}$ cycloalkyl, $C_3$–$C_{10}$ cycloalkenyl, ($C_3$–$C_{10}$ cycloalkyl) $C_1$–$C_6$ alkyl, $C_1$–$C_3$ haloalkyl, or heterocycloalkyl, $C_1$–$C_8$ alkylsulfonyl, arylsulfonyl, heteroarylsulfonyl, $C_1$–$C_8$ alkanoyl, aroyl, heteroaroyl, aryl, heteroaryl, $C_1$–$C_6$ arylalkyl or $C_1$–$C_6$ heteroarylalkyl;

$R^{11}$ is selected from H, $C_1$–$C_6$ alkyl, $C_3$–$C_{10}$ cycloalkyl, ($C_3$–$C_{10}$ cycloalkyl) $C_1$–$C_6$ alkyl;

$R^{12}$ is selected from H, aryl, heteroaryl, $C_1$–$C_6$ alkyl, $C_3$–$C_{10}$ cycloalkyl, ($C_3$–$C_{10}$ cycloalkyl) $C_1$–$C_6$ alkyl, optionally substituted with $OR^7$, $NR^8R^9$, $C_3$–$C_6$ amninocarbocycle, or $C_2$–$C_5$ aminoheterocycle;

$R^{13}$ is independently selected at each occurrence from H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_6$ alkenyl, $C_2$–$C_6$ alkynyl, $C_1$–$C_6$ haloalkyl, with the proviso that when $R^7$ is $SO_2R^{13}$, $R^{13}$ cannot be H; and $R^{14}$ is H, $C_1$–$C_6$ alkyl, $C_3$–$C_{10}$ cycloalkyl, ($C_3$–$C_{10}$ cycloalkyl) $C_1$–$C_6$ alkyl, $C_2$–$C_4$ alkenyl, $C_2$–$C_4$ alkynyl, halo, or CN.

23. A compound according to claim 22, wherein $R^{14}$ is H, $C_1$–$C_4$ alkyl, F or Cl.

24. A compound according to claim 23, wherein
$R^1$ is H, $C_1$–$C_4$ alkyl, ($C_3$–$C_6$ cycloalkyl) $C_1$–$C_2$ alkyl, where the alkyl and cycloalkyl groups are optionally substituted with 1–3 fluorines;
$R^3$ is H, $C_1$–$C_4$ alkyl, ($C_3$–$C_6$ cycloalkyl) $C_1$–$C_2$ alkyl, where the alkyl and cycloalkyl groups are optionally substituted with 1–3 fluorines;
A is $CH_2$, optionally substituted with one or two of the following: F, $CF_3$, or $C_1$–$C_3$ alkyl;
B is a 1, 2 or 3 carbon chain, optionally substituted with one or two of the following: F, $CF_3$, or $C_1$–$C_3$ alkyl.

25. A Compound according to claim 24, wherein
$R^4$ is phenyl, substituted with 2 or 3 substituents independently selected from $C_1$–$C_3$ alkyl, $C_3$–$C_6$ cycloalkyl, $C_3$–$C_6$ cycloalkenyl, ($C_3$–$C_5$ cycloalkyl) $C_1$–$C_2$ alkyl, $C_2$–$C_6$ alkenyl, F, Cl, $C_{1-C2}$ fluorooalkyl, $OR^7$, $C_1$–$C_3$ alkyl-$OR^7$, $NR^8R^9$, $C_1$–$C_6$ alkyl-$NR^8R^9$, $CONR^8R^9$, $C_1$–$C_3$ alkyl-$CONR^8R^9$, $COOR^7$, $C_2$–$C_6$ alkynyl, wherein the phenyl ring is minimally 2,4 disubstituted.

26. A compound according to claim 25, wherein
A is $CH_2$;
B is $CH_2$; or
B and $R^5$ form a 5 to 7 member heterocyclic ring, substituted on carbon with $R^{7a}$;

$R^{7a}$ is independently selected at each occurrence from H, $C_1$–$C_3$ alkyl, $C_3$–$C_6$ cycloalkyl, $C_3$–$C_6$ cycoalklenyl, ($C_3$–$C_6$ cycloalkyl) $C_1$–$C_2$ alkyl, $C_1$–$C_2$ flouroalkyl, heterocycoalkyl, $C_1$–$C_4$ alkanoyl, aroyl, heteroaroyl, aryl, heteroaryl, $C_1$–$C_2$ arylalkyl or $C_1$–$C_2$ heteroarylalkyl each optional substituted with 1 to 3 substituents independently selected from F, Cl, $CF_3$, $OR^{13}$, $NR^8R^9$, $C_1$–$C_2$ alkyl-$OR^{13}$, $C_1$–$C_2$ alkyl-$NR^8R^9$, $CONR^8R^9$, $COOR^{13}$, and CN;

$R^8$ is H, $C_1$–$C_3$ alkyl, $CF_3$ or $CH_2CF_3$;

$R^9$ is H or $C_1$–$C_3$ alkyl;

$R^{13}$ is H, or $C_1$–$C_3$ alkyl, $CF_3$ or $CH_2CF_3$.

27. A compound according to claim 25, wherein
A is $CH_2$, optionally substituted with one or two of the following: F, $CF_3$, or methyl, ethyl, isopropyl;
B is $CH_2$, optionally substituted with one or two of the following: F, $CF_3$, methyl, ethyl, ethyl or isopropyl.

28. A Compound according to claim 27, wherein
$R^5$ is $C_1$–$C_7$, alkyl, $C_3$–$C_6$ cycloalkyl, or $C_3$–$C_6$ cycloalkyl $C_1$–$C_2$ alkyl, substituted with F, $CF_3$, $OR^7$ or $NR^8R^9$;
A is $CH_2$, optionally substituted with methyl;
B is $CH_2$, optionally substituted with methyl;
X is N or CH.

29. A compound according to claim 28, wherein
$R^7$ is H, $C_1$–$C_3$ alkyl, $CF_3$ or $CH_2CF_3$;
$R^8$ is H, $C_1$–$C_3$ alkyl, $CF_3$ or $CH_2CF_3$;
$R^9$ is H or $C_1$–$C_3$ alkyl or $NR^8R^9$ taken together to form a pyrrolidine, piperidine or morpholine ring.

30. A Compound according to claim 27, wherein
$R^5$ is 3- or 4-tetrahydropyranyl, 3-tetrahydrofuranyl, 3- or 4-tetrahydrothiopyranyl, 3- or 4-cyclohexenyl, or 3-cyclopentenyl, optionally substituted with 1 or 2 substituents selected from $C_1$–$C_3$ alkyl;
A is $CH_2$, optionally substituted with methyl;
B is $CH_2$ optionally substituted with methyl; and
X is N or CH.

31. A Compound according to claim 27, wherein
$R^5$ is 3- or 4-piperidinyl or 3-pyrrolidinyl, optionally substituted on 1 or 2 carbons with $C_1$–$C_3$ alkyl, and one substituent on nitrogen from H, $C_1$–$C_6$, alkyl, $C_{36}$ cycloalkyl, $C_3$–$C_6$ cycloalkenyl, ($C_3$–$C_6$ cycloalkyl) $C_1$–$C_2$ alkyl, $C_1$–$C_4$ alkenyl, $C_1$–$C_3$ fluoroalkyl, $C_2$–$C_4$ alkyl-$OR^7$, $C_2$–$C_4$ alkyl-$NR^8R^9$, heterocycloalkyl, CO—$C_1$–$C_4$ alkyl, aryl, $C_1$–$C_3$, alkylaryl, heteroaryl, $C_1$–$C_3$ alkylheteroaryl where aryl or heteroaryl is optionally substituted with 1 to 3 substituents independently selected at each occurrence from $C_1$–$C_3$ alkyl, F, Cl, $C_1$–$C_2$ fluoroalkyl, $OR^7$, $NR^8R^9$, $C_1$–$C_2$ alkyl-$OR^7$, $C_1$–$C_2$ alkyl-$NR^8R^9$, $CONR^8R^9$, $COOR^7$, CN, $SO_2NR^8R^9$, $SO_2R^7$, aryl, heteroaryl, heterocycloalkyl, 3-, 4-, or 5-(2-oxo-1,3-oxazolidinyl).

32. A compound according to claim 31, wherein
$R^5$ is 3- or 4-piperidinyl or 3-pyrrolidinyl, optionally substituted on nitrogen with H, $C_1$–$C_3$ alkyl, $CH_2CF_3$, acetyl, pyridyl, benzyl, methylenepyridyl, pyrimidinyl, or pyrazinyl, where the aryl or heteroaryl group is optionally substituted with 1 to 2 substituents independently selected at each occurrence from $C_1$–$C_3$, alkyl, F, Cl, $CF_3$, $OR^7$, $NR^8R^9$;
$R^7$ is H, $C_1$–$C_2$ alkyl, $CF_3$ or $CH_2CF_3$;
$R^8$ is H, $C_1$–$C_2$ alkyl, $CF_3$ or $CH_2CF_3$;
$R^9$ is H or $C_1$–$C_2$ alkyl;

A is CH₂, optionally substituted methyl;
B is CH₂, optionally substituted with methyl;
X is N or CH.

33. A compound according to claim 27, wherein
R⁵ is C₁–C₂ arylalkyl, C₁–C₂ heteroarylalkyl, C₃–C₄ arylcycloalkyl, or C₃–C₄ heteroarylcycloalkyl, where aryl is phenyl or naphthyl, and heteroaryl is 2-, 3-, or 4-pyridyl, 2-, 4- or 5 pyrimidinyl, triazinyl, 1-, 2- or 4-imidazolyl, 2-, 4-, or 5-oxazolyl, isoxazolyl, indolyl, pyrazolyl, quinolyl, isoquinolyl, 2-, 4-, or 5-thiazolyl, benzothiadiazolyl, 1-, 3- or 4 pyrazolyl, 1-, 3- or 4-triazolyl, 2-triazinyl, 2-pyr, zinyl, 2-, or 3-furanyl, 2-, or 3-thienyl, 2-, or 3-benzothienyl, or 1-, 2- or 5-tetrazolyl, each of which is optionally substituted with 1 to 3 substituents independently selected at each occurrence from C₁–C₃ alkyl, C₃–C₆ cycloalkyl, C₃–C₆ cycloalkenyl, (C₃–C₆ cycloalkyl) C₁–C₂ alkyl, C₁–C₆ alkenyl, F, Cl, C₁–C₂ fluoroalkyl, OR⁷, NR⁸R⁹, C₁–C₂ alkyl-OR⁷, C₁–C₂ alkyl-NR⁸R⁹ or CN.

34. A compound according to claim 33, wherein
R⁵ is phenethyl, pyridinylethyl, or 2-tetrahydonaphthylenyl, each of which is optionally substituted with 1 to 2 substituents independently selected at each occurrence from
C₁–C₂ alkyl, F, Cl, CF₃, OR⁷, NR⁸R⁹;
R⁷ is H, C₁–C₂ alkyl, CF₃ or CH₂CF₃;
R⁸ is H, C₁–C₂ alkyl, CF₃ or CH₂CF₃;
R⁹ is H or C₁–C₂ alkyl;
A is CH, optionally substituted with methyl;
B is CH₂, optionally substituted with methyl;
X is N or CH.

35. A compound according to claim 26, where the structure is [3-(2,6-dichloro-4-methoxy-phenyl)-2,5-dimethyl-pyrazolo [1,5-a]pyrimidin-7-yl]-(6-methyl-piperidin-2-ylmethyl)-amine.

36. A compound according to claim 29, where the compound is selected from the group consisting of:
2-{2-[3-(2,6-dichloro-4-methoxy-phenyl)-2,5-dimethyl-pyrazolo[1,5-a]pyrimidin-7-ylamino]-ethylamino}-butan-1-ol;
N-{2-[3-(2,6-dichloro-4-methoxy-phenyl)-2,5-dimethyl-pyrazolo[1,5-a]pyrimidin-7-ylamino]-ethyl}-N'-methyl-cyclohexane-1,4-diamine;
N-{2-[3-(2,6-dichloro-4-methoxy-phenyl)-2,5-dimethyl-pyrazolo[1,5-a]pyrimidin-7-ylamino]-ethyl}-N'-ethyl-cyclohexane-1,4-diamine;
N-[3-(2,6-dichloro-4-methoxy-phenyl)-2,5-dimethyl-pyrazolo[1,5-a]pyrimidin-7-yl]-N-(4-morpholin-4-yl-cyclohexyl)-ethane-1,2-diamine;
4-{2-[3-(2,6-dichloro-4-methoxy-phenyl)-2,5-dimethyl-pyrazolo[1,5-a]pyrimidin-7-ylamino]-ethylamino}-cyclohexanol;
3-{2-[3-(2,6-dichloro-4-methoxy-phenyl)-2,5-dimethyl-pyrazolo[1,5-a]pyrimidin-7-ylamino]-ethylamino}-propane-1,2-diol;
N-{2-[3(2,6-dichloro-4-methoxy-phenyl)-2,5-dimnethyl-pyrazolo[1,5-a]pyrimidin-7-ylamino]-ethyl}-N'-isobutyl-cyclohexane-1,4-diamine;
N-{2-[3-(2,6-dichloro-4-methoxy-phenyl)-2,5-dimethyl-pyrazolo[1,5-a]pyrimidin-7-ylamino]-ethyl}-N'-isobutyl-cyclohexane-1,4-diamine;
4-{2-[3-(2,6-dichloro-4-ethoxy-phenyl)-2,5-dimethyl-pyrazolo[1,5-a]pyrimidin-7-ylamino]-1-methyl-ethylamino}-cyclohexanol;
2-{2-[3-(2,6-dichloro-4-ethoxy-phenyl)-2,5-dimethyl-pyrazolo[1,5-a]pyrimidin-7-ylamino]-ethylamino}-cyclohexanol;
N-[3-(2,6-dichloro-4-methoxy-phenyl)-2,5-dimethyl-pyrazol to [1,5-a]pyrimidin-7-yl]-N'-(4,4,4-trifluoro-butyl)-ethane-1,2-diamine;
N-[3-(2,6-dichloro-4-ethoxy-phenyl)-2,5-dimethyl-pyrazolo[1,5-a]pyrimidin-7-yl]-N'-(2,2,2-trifluoro-ethyl)-ethane-1,2-diamine;
N-[3-(2,6-dichloro-4-methoxy-phenyl)-2,5-dimethyl-pyrazol[1,5-a]pyrimidin-7-yl]-N'-(2-trifluoromethyl-cyclohexyl)-ethane-1,2-diamine;
N-[3-(2,6-dichloro-4-methoxy-phenyl)-2,5-dimethyl-pyrazolo [1,5-a]pyrimidin-7-yl]-N'-(4-trifluoromethyl-cyclohexyl)-ethane 1,2-diamine;
N-[3-(2,6-dichloro-4-methoxy-phenyl)-2,5-dimethyl-pyrazolo[1,5-a]pyrimidin-7-yl]-N'-(2,2-difluoro-ethyl)-ethane-1,2-diamine;
N-[3-(2,6-dichloro-4-methoxy-phenyl)-2,5-dimethyl-pyrazolo [1,5-a]pyrimidin-7-yl]-N'-(2-fluoro-1-methyl-ethyl)-ethane-1,2-diamine;
N-[3-(2,6-dichloro-4-methoxy-phenyl)-2,5-dimethyl-pyrazolo 5-a]pyrimidin-7-yl]-N'-(2-fluoro-cyclohexyl)-ethane-1,2-diamine.

37. A compound of claim 30, where the compound is selected from the group consisting of
N-[3-(2,6-dichloro-phenyl)-2,5-dimethyl-pyrazolo[1,5-a]pyrimidin-7-yl]-N'-(tetrahydro-pyran-4-yl)-ethane-1,2-diamine; N-[3-(2,4-dichloro-6-methoxy-phenyl)-2,5-dimethyl-pyrazolo[1,5-a]pyrimidin-7-yl]-N'-(tetrahydro-pyran-4-yl)-ethane-1,2-diamine; N-[3-(2,6-dichlork)-4-methoxy-phenyl)-2,5-dimethyl-pyrazolo[1,5-a]pyrimidin-7-yl]-N'-(tetrahydro-pyran-4-yl)-ethane-1,2-diamine; N1-[3-(2,6-Dichloro-phenyl)-2,5-dimethyl-pyrazolo to [1,5-a]pyrimidin-7-yl]-N2&-(tetrahydro-pyran-4-yl)-propane-1,2-diamine; N-[3-(2,6-dichloro-4-methoxy-phenyl)-2,5-dimethyl-pyrazolo[1,5-a]pyrimidin-7-yl]-N'-(2-methyl-tetrahydro-furan-3-yl)-ethane-1,2-diamine; N-[3-(2,6-dichloro-4-ethoxy-phenyl)-2,5-dimethyl-pyrazolo[1,5-a]pyrimidin-7-yl]-N'-(tetrahydro-pyran-4-yl)-ethane-1,2-diamine; 3,5-dichloro-4-{2,5-dimethyl-7-[2-(tetrahydro-pyran-4-ylamino)-ethylamino]-pyrazolo[1,5-a]pyrimidin-3-yl}-benzonitrile; N-[3-(2,6-dichloro-4-propoxy-phenyl)-2,5-dimethyl-pyrazolo[1,5-a]pyrimidin-7-yl]-N'-(tetrahydro-pyran-4-yl)-ethane-1,2-diamine; 2-(3,5-dichloro-4-(2,5-dimethyl-7-[2-(tetrahydro-pyran-4-ylamino)-ethylamino]-pyrazolo[1,5-a]pyrimidin-3-yl}-phenyl)-propan-2-ol; N-[3-(2,6-dichloro-4-cyclopent-1-enyl-phenyl)-2,5-dimethyl-pyrazolo[1,5-a]pyrimidin-7-yl]-N'-(tetrahydro-pyran-4-yl)-ethane-1,2-diamine; N-[8-(2,6-dichloro-4-ethoxy-phenyl)-2,7-dimethyl-pyrazolo[1,5-a] [1,3,5]triazin-4-yl]-N'-(tetrahydro-pyran-4-yl)-ethane-1,2-diamine; (3.5-dichloro-4-(2,5-dimethyl-7-[2-(tetrahydro-pyran-4-ylamino)-ethylamino]-pyrazolo[1,5-a]pyrimidin-3-yl}-phenyl)-methanol; N-[3-(2,6-dichloro-4-ethoxy-phenyl)-2,5-dimethyl-pyrazolo[1,5-a]pyrimidin-7-yl]-N'-( 2-methyl-tetrahydro-faran-3-yl)-ethane-1,2-diamine; N-[5-tert-butyl-3-(2,6-dichloro-4-methoxy-phenyl)-2-methyl-pyrazolo [1,5-a]pyrimidin-7-yl]-N'-(tetrahydro-pyran-4-yl)-ethane-1,2-diamine; N-[3-(2,6-dichloro-4-ethoxy-phenyl)-5-ethyl-2-methyl-pyrazolo[1,5-a]pyrimidin-7-yl]-N'-(tetrahydro-pyran-4-yl)-ethane-1,2-diamine; N-cyclohex-3-enyl-N'-[3-(2,6-dichloro-4-methoxy-phenyl)-2,5-dimethyl-pyrazolo[1,5-a]pyrimidin-7-yl]-ethane-1,2-diamine; N-cyclohex-3-enyl-N'-[8-(2,6-dichloro-4-ethoxy-phenyl)-2,7-dimethyl-pyrazolo[1,5- a][1,3,5]triazin-4-yl]-ethane-1,2-diamine;
N-cyclopent-3-enyl-N'-[3-(2,6-dichloro-4-methoxy-phenyl)-2,5-dimethyl-pyrazolo[1,5-a]pyrimidin-7-yl]-ethane-1,2-diamine.

38. A compound of claim 32 where the structure is selected from the group consisting of N-[3-(2,6-dichloro-phenyl)-2,5-dimethyl pyrazolo[1,5-a]pyrimidin-7-yl]-N'-(1-ethyl-piperidin-5-a]pyrimidin-7-yl]-N'-(2,2, 6, 6-tetramethyl-piperidin-4-yl)-ethane-1,2diamine;

N-[3-(2,6-dichloro-phenyl)-2,5-dimethyl-pyrazolo [1,5-a]pyrimidin-7-yl]-N'-19 piperidin-4-yl-ethane-1,2-diamine;

N-[3-(2,6-dichloro-phenyl)-2,5-dimethyl-pyrazolo[1,5-a]pyrimidin-7-yl]-N'-(1-ethyl-piperidin-3-yl)-ethane-1,2-diamine;

N-(1benzyl-pyrrolidin-3-yl)-N'-[3-(2,6-dichloro-phenyl)-2,5-dimethyl-pyrazolo[1,5-a]pyrimidin-7-yl]-ethane-1,2-diamine;

N-[3-(2,6-dichloro-phenyl)-2,5-dimethyl-pyrazolo[1,5-a]pyrimidin-7-yl]-N'-pyrimidin-2-yl-ethane-1,2-diamine;

N-(1-benzylpiperidin-4-yl)-N'-[3-(2,4-dichloro-6-methoxy-phenyl)-2,5-diethyl-pyrazolo [1,5-a]pyrimidin-7-yl]-ethane-1,2-diamine;

N-(1-benzyl-piperidin-4-yl)-N'-[3-(2,6-dichloro-4-methoxy-phenyl)-2,5-dimethyl-pyrazolo[1,5-a]pyrimidin-7-yl]-ethane-1,2-diamine;

N-[3(2,6-dichloro-4-methoxy-phenyl)-2,5-dimethyl-pyrazolo[1,5-a]pyrimidin-7-yl]-N'-(1-methyl-piperidin-4-yl)-ethane-1,2-diamine;

N-[3-(2,6-dichloro-4-methoxy-phenyl)-2,5 dimethyl-pyrazolo [1,5-a]pyrimidin-7-yl]-N'-(1-ethyl-piperidin-4-yl)-ethane-1,2-di amine;

N-[3-(2,6-dichloro-4-methoxy-phenyl)-2,5-dimethyl-pyrazolo[1,5-a]pyrimidin-7-yl]-N'-(1-isopropyl-piperidin-4-yl)-ethane-1,2-diamine;

N-[3-(2,6-dichloro-4-methoxy-phenyl)2,5-dimethyl-pyrazolo [1,5-a]pyrimidin-7-yl]-N'-(2,2,6,6-tetramethyl-piperidin-4-yl)ethane-1,2-diamine;

N-[3-(2,6-dichloro-4-methoxy-phenyl)-2,5-dimethyl-pyrazolo[1,5-a]pyrimidin-7-yl]-N'-(1-ethyl-piperidin-3-yl)-ethane-1,2-diamine;

N-[3-(2,6-dichloro-4methoxy-phenyl)-2, 5-dimethyl-pyrazol to [1, 5-a] pyrimidin-7-yl]-N'-piperidin-4-yl-ethane 1,2-diamine;

N²-(1-Benzyl-piperidin-4-yl)-N'-[3-(2,6-dichloro-phenyl)-2,5-dimethyl-pyrazolo[1,5-ajpyrimidin-7-yl]-propane-1,2-diamine;

N-[3-(2,6-Dichloro-4-methoxy-phenyl)-2,5-dimethyl-pyrazolo[1,5-a]pyrimidin-7-yl]-N'-(1-pyridin-3-ylmethyl-piperidin-4-yl)-ethane-1,2-diamine;

N-[3-(2,6-Dichloro-4-methoxyphenyl)-2,5-dimethyl-pyrazolo [1,5-a]pyrimidin-7-yl]-N'-(1-pyridin-4-ylmethyl-piperidin4-yl)-ethane-1,2-diamine; 3,5-Dichloro-4-12,5-dimethyl-7-[2-(1-phenyl-pyrrolidin-3-ylamino)-ethylamino]-pyrazolo[1,5-a]pyrimidin-3-yl]-phenol;

N-[3-(2,6-dicloro-4-methoxy-phenyl)-2,5-dimethyl-purazolo[1,5-a]pyrimdin-7-yl]-N'-(1-pyridin-2-ylmethyl-piperidin-4-yl)-ethane-1,2-diamine;

3,5-dichloro-4-(2,5-dimethyl-7-[2-(1-pyrimidin-2-yl-piperidin-4-ylamino)-ethylamino]-pyrazolo[1,5-a]pyrimidin-3-yl}-benzonitrile;

N-[3-(2,6-dichloro-4-ethoxy-phenyl)-2,5-dimethyl-pyrazolo[1,5 a]pyrimidin-7-yl]-N'-(1-pyrimidin-2-yl-piperidin-4-yl)-ethane-1,2-diamine;

N-[3-(2,6dichloro-4-methoxy-phenyl)-2,5-dimethyl-pyrazolo[1,5-a]pyrimidin-7-yl]-N'-(1-pyrimidin-2-yl-piperidin-4-yl)-ethane-1,2-diamine;

N-(1-benzyl-piperidin-4-yl)-N'-[3(2,6-dichloro-4-ethoxy-phenyl)-2,5-dimethyl-pyrazolo[1,5-a]pyrimidin-7-yl]-ethane-1,2-diamine;

N-[3-(2,6-dichloro-phenyl)-5-ethyl-2-methyl-pyrazolo[1,5-a]pyrimidin-7-yl]-N'-(1-pyrimidin-2-yl-piperidin-4-yl)-ethane-1,2-diamine;

N-[3-(2,6-dichloro-phenyl)–5isopropyl-2-methyl-pyrazolo[1,5-a]pyrimidin-7-yl]-N'-(1-pyrimidin-2-yl-piperidin-4-yl)ethane-1,2-diamine;

N-[3-(2,4-dichloro-phenyl)–5-isopropyl-2-methyl-pyrazolo[1,5a]pyrimidin-7-yl]-N'-(1-pyrimidin-2-yl-piperidin-4-yl)-ethane-1,2-diamine;

N-[3-(2,6-dichloro-4-ethoxy-phenyl)-2,5-dimethyl-pyrazolo[1,5-a]pyrimidin-7-yl]-N²-(1-pyrimidin-2-yl-piperidin-4-yl)-propane-1,2-diamine;

N'-[3-(2,6-dichloro-4-methoxy-phenyl)-5isopropyl-2-methyl-pyrazolo[1,5-a]pyrimidin-7-yl]-N2-(1-pyrimidin-2-yl-piperidin-4-yl)propane-1,2-diamine;

N-[3-(2,6-dichloro-4-methoxy-phenyl)-5-ethyl-2-methylpyrazoto [1,5-a]pyrimidin-7-yl]-N'-(1-pyrimidin-2-yl-piperidin-4-yl)-ethane-1,2-diamine;

N'-[3-(2,6-dichloro-4-methoxy-phenyl)-2-methyl-5-propyl-pyrazolo[1,5-a]pyrimidin-7-yl]-N²-(1-pyrimidin-2-yl-piperidin-4-yl)-propane-1,2-diamine;

N'-[3-(2,6-dichloro-4methoxy-phenyl)5-ethyl-2-methyl-pyrazolo[1,5-a]pyrimidin-7-yl]-N²-(1-pyrimidin-2-ylpiperidin-4-yl)-propane-1,2-diamine;

N-[3-(2,6-dichloro-phenyl)-2-methyl-5-propylpyrazoto [1,5-a]pyrimidin-7-yl]-N'-(1-pyrimidin-2-yl-piperidin-4-yl)-ethane-1,2-diamine;

N'-[3-(2,6-dichloro-phenyl)-2-methyl-5-propyl-pyrazolo [1,5-a]pyrimidin-7-yl]-N2-(1-pyrimidin-2-yl-piperidin-4-yl)-propane-1,2-diamine;

N'-[3-(2,6-dichloro-phenyl)-5-ethyl-2-methyl-pyrazolo [1,5-a]pyrimidin-7-yl]-N²-(1-pyrimidin-2-yl-piperidin-4-yl)-propane1,2-diamine;

N-[5-ethyl-2-methyl-3-(2,4,6-trimethyl-phenyl)-pyrazolo[1,5-a]pyrimidin-7-yl]-N'-(1-pyrimidin-2-yl-piperidin-4-yl)-ethane-1,2-diamine;

N'-[5-ethyl-2-methyl-3-(2,4,6-trimethyl-phenyl)-pyrazolo[1,5-a]pyrimidin-7-yl]-N²-(1-pyrimidin-2-yl-piperidin-4-yl)-propane-1,2-diamine; N-[3-(2,6dichloro-4-ethynyl-phenyl)-2,5-dimethylpyrazolo[1,5-a]pyrimidin-7-yl]-N'-(1-pyrimidin-2-yl-piperidin-4-yl)-ethane-1,2-diamine;

N-[2-methyl-5-propyl-3-(2,4,6-trimethyl-phenyl)-pyrazol to [1,5-a]pyrimidin-7-yl]-N'-(1pyrimidin-2-yl-piperidin-4-yl)-ethane-1,2-diamine;

N-[2,5-dimethyl-3-(2,4,6-trimethylphenyl)-pyrazolo[1,5-a]pyrimidin-7-yl]-N'-(1-pyridin-2-yl-piperidin-4-yl)-ethane-1,2-diamine;

N'-[3-(2,6-Dimethyl-phenyl)-5-ethyl-2-methyl-pyrazolo [1,5-a]pyrimidin-7-yl]-N'-(1-pyrimidin-2-yl-piperidin-4-yl)-propane-1,2-diamine;

N-[3-(2,6-dimethyl-phenyl)-2-methyl-5-propyl-pyrazolo [1,5-a]pyrimidin-7-yl]-N'-(1-pyrimidin-2-yl-piperidin-4-yl)-ethane-1,2-diamine;

N'-[3-(2,6-Dimethyl-phenyl)-2-methyl-5-propyl-pyrazolo[1,5-a]pyrimidin-7-yl]-NZ-(1-pyrimidin-2-yl-piperidin-4-yl)-propane-1,2-diamine;

N'-[3-(2,6dimethyl-phenyl)-2,5-dimethyl-pyrazolo[1,5-a]pyrimidin-7-yl]-N²-(1-pyrimidin-2-ylpiperidin-4-yl)-propane-1,2-diamine;

N-[3-(2,4-dimethyl-phenyl)-5-ethyl-2-methyl-pyrazolo[1,5-a]pyrimidin-7-yl]-N'-(1-pyrimidin-2-yl-piperidin-4-yl)-ethane-1,2-diamine;

N-[3-(2,4-dimethyl-phenyl)-2-methyl-5-propyl-pyrazolo[1,5-a]pyrimidin-7-yl]-N'-(1-pyrimidin-2-yl-piperidin-4-yl)-ethane-1,2-diamine; and 1-[4-(1-{[3-(2,6-dichloro-4-methoxyphenyl)-2,5-dimethyl-pyrazolo[1,5-a]pyrimidin-7-ylamino]-methyl}-propylamino)piperidin-1-yl]-ethanone.

39. A compound of claim 35 where the structure is selected from the group consisting of N-[2,5-dimethyl-3-(2,4,6-trimethylphenyl)-pyrazolo[1,5-a]pyrimidin-7-yl]-N'-[2-(4-methoxy-phenyl)-ethyl]-ethane-1,2diamine;

N-[3-(2,6-dichloro-4-methoxy-phenyl)-2,5-dimethyl-pyrazolo1,5-a]pyrimidin-7-yl]-N'-[2-(4-methoxy-phenyl)-ethyl]-ethane-1,2-diamine;

N-[3-(2,6-dichloro-4-methoxy-phenyl)-2,5-dimethyl-pyrazolo[1,5-a]pyrimidin-7-yl]-N'-[2-(3-ethoxy-4-methoxy-phenyl)-ethyl]-ethane-1,2-diamine;

N-[3-(2,6-dichloro-4-methoxy-phenyl)-2,5-dimethyl-pyrazolo 1,5-a]pyrimidin-7-yl]-N'-[2-(4-ethoxy-3-methoxy-phenyl)-ethyl]-ethane-1,2-diamine;N-[3-(2,6-dichloro-4-methoxy-phenyl)-2,5-dimethyl-pyrazolo[1,a]pyrimid in-7-yl]-N'-(1,2,3,4-tetrahydro-naphthalen-2-yl)-ethane-1,2-diamine;

N-[3-(2,6-dichloro-4-methoxy-phenyl)-2,5-dimethyl-pyrazolo[1,5-a]pyrimidin-7-yl]-N'-(2-pyridin-2-yl-ethyl)-ethane-1,2-diamine;

N-[3-(2,6-dichloro-4-methoxy-phenyl)-2,5-dimethyl-pyrazolo[1,5-a]pyrimidin-7-yl]-N'-(2-pyridin-3-yl-ethyl)-ethane-1,2-diamine; and N-[3-(2,6-dichloro-4-methoxy-phenyl)-2,5-dimethyl-pyrazolo [1,5-a]pyrimidin-7-yl]-N'-(2-pyridin4-yl-ethyl)-ethane-1,2-diamine.

40. A method of treating obesity comprising administering to a mammal in need of such treatment a therapeutically effective amount of a compound of claim 21 or 22 or a prodrug thereof or a pharmaceutically acceptable salt of said compound or of said prodrug.

41. A method as recited in claim 40, wherein the amount of said compound administered is about 0.01 mg/kg/day to about 50 mg/kg/day.

42. A method as recited in claim 40 wherein the mammal is female or male human.

43. A pharmaceutical composition which comprises a therapeutically effective amount of compound of claim 22 or a prodrug thereof or a pharmaceutically acceptable salt of said compound or of said prodrug and a pharmaceutically acceptable carrier, vehicle or diluent.

44. A pharmaceutical composition for the treatment of obesity which comprises a therapeutically effective amount of compound of claim 22 or a prodrug thereof or a pharmaceutically acceptable salt of said compound or of said prodrug and a pharmaceutically acceptable carrier, vehicle or diluent.

45. A pharmaceutical combination composition comprising a therapeutically effective amount of a composition comprising: (a) first compound, said first compound being a compound of claim 22, a prodrug thereof, or a pharmaceutically acceptable salt of said compound or of said prodrug; and (b) a second compound, said second compound being a agonist, a thyromimetic, an eating behavior modifying agent or a NPY antagonist; and a pharmaceutical carrier, vehicle, diluent.

46. A method of treating obesity comprising administering to a mammal in need of such treatment: (a) first compound, said first compound being a compound of claim 22, a prodrug thereof, or a pharmaceutically acceptable salt of said compound or of said prodrug; and (b) a second compound, said second compound being a $\beta_3$ agonist, a thyromimetic, an eating behavior modifying agent or a NPY antagonist; and a pharmaceutical carrier, vehicle, diluent; (and (c) wherein the amounts of the first and second compounds result in a therapeutic effect.

47. A kit comprising: (a) first compound, said first compound being a compound of claim 22 or 23, a prodrug thereof, or a pharmaceutically acceptable salt of said compound or of said prodrug; (b) a second compound, said second compound being a $\beta_3$ agonist, a thyromimetic, an eating behavior modifying agent or a NPY antagonist; and a pharmaceutical carrier, vehicle, diluent; and (c) means for containing said first and second unit dosage forms wherein the amounts of the first and second compounds result in a therapeutic effect.

48. A pharmaceutical combination composition comprising a therapeutically effective amount of a composition comprising (a) first compound, said first compound being a compound of claim 21 or 22, a prodrug thereof, or a pharmaceutically acceptable salt of said compound or of said prodrug; (b) a second compound, said second compound being an aldose reductase inhibitor, a glycogen phosphorylase inhibitor, a sorbitol dehydrogenase inhibitor, insulin metformin, acarbose, a thiazolidinedione, a glitazone, rezulin, trogitalazone, a sulfonylurea, glipazide, glyburide, or chlorpropamide; (c) a pharmaceutical carrier, vehicle, or diluent.

49. A pharmaceutical composition according to claim 22 for the treatment of disorders or disease states caused by eating disorders, of obesity, bulimia nervosa, diabetes, dislipidemia, hypertension, memory loss, epileptic seizures, migraine, sleep disorders, pain, sexual/reproductive disorders, depression, anxiety, cerebral hemorrhage, shock, congestive heart failure, nasal congestion or diarrhea.

50. A Compound according to claim 24, wherein $R_2$ is H;

$R_6$ is H;

$R^4$ is phenyl, substituted with 2 or 3 substituents independently selected from $C_1$–$C_3$alkyl, $C_3$–$C_6$ cycloalkyl, $C_3$–$C_6$ cycloalkenyl, $C_2$–$C_4$ alkenyl, F, Cl, $CF_3$, $CHF_2$, $CH_2CF_3$, OMe, $OCF_3$, OEt, OPr, OiPr, $C_2$–$C_4$ alkyl OH, $C_2$–$C_6$ alkynyl, wherein the phenyl ring is minimally 2,4 di-substituted.

* * * * *

SEQUENCE LISTING

<160> NUMBER OF SEQ ID NOS: 1

<210> SEQ ID NO 1
<211> LENGTH: 1605
<212> TYPE: DNA
<213> ORGANISM: Homo sapiens

<400> SEQUENCE: 1

```
ccttctttaa tgaagcagga gcgaaaaaga caaattccaa agaggattgt tcagttcaag      60
ggaatgaaga attcagaata attttggtaa atggattcca atatggggaa taagaataag     120
ctgaacagtt gacctgcttt gaagaaacat actgtccatt tgtctaaaat aatctataac     180
aaccaaacca atcaaaatga attcaacatt attttcccag gttgaaaatc attcagtcca     240
ctctaatttc tcagagaaga atgcccagct tctggctttt gaaaatgatg attgtcatct     300
gcccttggcc atgatattta ccttagctct tgcttatgga gctgtgatca ttcttggtgt     360
ctctggaaac ctggccttga tcataatcat cttgaaacaa aaggagatga gaaatgttac     420
caacatcctg attgtgaacc tttccttctc agacttgctt gttgccatca tgtgtctccc     480
ctttacattt gtctacacat taatggacca ctgggtcttt ggtgaggcga tgtgtaagtt     540
gaatcctttt gtgcaatgtg tttcaatcac tgtgtccatt ttctctctgg ttctcattgc     600
tgtggaacga catcagctga taatcaaccc tcgagggtgg agaccaaata atagacatgc     660
ttatgtaggt attgctgtga tttgggtcct tgctgtggct tcttctttgc cttttcctgat    720 ctaccaagta atgactgatg agccgttcca aaatgtaaca cttgatgcgt acaaagacaa     780
atacgtgtgc tttgatcaat ttccatcgga ctctcatagg ttgtcttata ccactctcct     840
cttggtgctg cagtattttg gtccactttg ttttatattt atttgctact tcaagatata     900
tatacgccta aaaggagaa acaacatgat ggacaagatg agagacaata agtacaggtc      960
cagtgaaacc aaaagaatca atatcatgct gctctccatt gtggtagcat ttgcagtctg    1020
ctggctccct cttaccatct ttaacactgt gtttgattgg aatcatcaga tcattgctac    1080
ctgcaaccac aatctgttat tcctgctctg ccacctcaca gcaatgatat ccacttgtgt    1140
caaccccata ttttatgggt tcctgaacaa aaacttccag agagacttgc agttcttctt    1200 caactttgt gatttccggt ctcgggatga tgattatgaa acaatagcca tgtccacgat     1260
gcacacagat gtttccaaaa cttctttgaa gcaagcaagc ccagtcgcat ttaaaaaaat    1320
caacaacaat gatgataatg aaaaaatctg aaactactta tagcctatgg tcccggatga    1380
catctgttta aaaacaagca caacctgcaa catactttga ttacctgttc tcccaaggaa    1440
tggggttgaa atcatttgaa aatgactaag attttcttgt cttgcttttt actgcttttg    1500
```

```
ttgtagttgt cataattaca tttggaacaa aaggtgtggg ctttggggtc ttctggaaat    1560
agttttgacc agacatcttt gaagtgcttt ttgtgaattt accag                    1605
```